United States Patent
Alvarez et al.

(10) Patent No.: US 10,329,327 B2
(45) Date of Patent: Jun. 25, 2019

(54) TRICALCIUM PHOSPHATE BINDING PEPTIDES AND USES THEREOF

(75) Inventors: Luis Alvarez, Frederick, MD (US); Linda G. Griffith, Cambridge, MA (US); Yadir Guerrero, Cambridge, MA (US); Linda Stockdale, Providence, RI (US); Jaime Rivera, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/991,842

(22) PCT Filed: Dec. 6, 2011

(86) PCT No.: PCT/US2011/063592
§ 371 (c)(1),
(2), (4) Date: Jun. 5, 2013

(87) PCT Pub. No.: WO2012/078671
PCT Pub. Date: Jun. 14, 2012

(65) Prior Publication Data
US 2014/0037593 A1 Feb. 6, 2014

Related U.S. Application Data

(60) Provisional application No. 61/419,946, filed on Dec. 6, 2010.

(51) Int. Cl.
| | |
|---|---|
| *C07K 7/08* | (2006.01) |
| *A61K 38/10* | (2006.01) |
| *A61K 35/28* | (2015.01) |
| *A61K 38/18* | (2006.01) |
| *A61L 27/12* | (2006.01) |
| *A61L 27/38* | (2006.01) |
| *A61L 27/54* | (2006.01) |
| *A61L 27/56* | (2006.01) |
| *C07K 14/485* | (2006.01) |
| *C12N 5/0775* | (2010.01) |

(52) U.S. Cl.
CPC .............. *C07K 7/08* (2013.01); *A61K 35/28* (2013.01); *A61K 38/10* (2013.01); *A61K 38/1808* (2013.01); *A61L 27/12* (2013.01); *A61L 27/3834* (2013.01); *A61L 27/3847* (2013.01); *A61L 27/54* (2013.01); *A61L 27/56* (2013.01); *C07K 14/485* (2013.01); *C12N 5/0662* (2013.01); *A61L 2300/25* (2013.01); *A61L 2300/252* (2013.01); *A61L 2300/414* (2013.01); *A61L 2400/08* (2013.01); *A61L 2400/18* (2013.01); *A61L 2430/02* (2013.01)

(58) Field of Classification Search
CPC ........ C07K 7/08; C07K 14/485; A61K 35/28; A61K 38/10; A61K 38/1808; A61L 27/12; A61L 27/3834; A61L 27/3847; A61L 27/54; A61L 27/56; A61L 2300/25; A61L 2300/252; A61L 2300/414; A61L 2400/08; A61L 2400/18; A61L 2430/02; C12N 5/0662

See application file for complete search history.

(56) References Cited

U.S. PATENT DOCUMENTS

| | | | |
|---|---|---|---|
| 5,152,791 A | 10/1992 | Hakamatsuka et al. | |
| 5,491,082 A | 2/1996 | Suzuki et al. | |
| 5,820,632 A * | 10/1998 | Constantz | A61K 6/0675 |
| | | | 423/308 |
| 5,906,828 A | 5/1999 | Cima et al. | |
| 6,949,251 B2 * | 9/2005 | Dalal | A61L 27/12 |
| | | | 424/423 |
| 2004/0197892 A1 | 10/2004 | Moore et al. | |
| 2005/0084962 A1 | 4/2005 | Simon | |
| 2005/0085623 A1 * | 4/2005 | Balian | C07K 7/08 |
| | | | 530/326 |
| 2006/0292198 A1 | 12/2006 | Dalal et al. | |

FOREIGN PATENT DOCUMENTS

| | | | | |
|---|---|---|---|---|
| WO | WO 2003/026590 A2 | 4/2003 | | |
| WO | WO 2005/039616 A1 | 5/2005 | | |
| WO | WO2006/078464 | * 7/2006 | ............ | A61K 38/00 |
| WO | WO 2006/078464 A2 | 7/2006 | | |
| WO | WO 2009/020550 A2 | 2/2009 | | |
| WO | WO 2009/108934 A2 | 9/2009 | | |
| WO | WO 2009/126648 A1 | 10/2009 | | |
| WO | WO 2010/051032 | * 5/2010 | ............... | C12N 5/07 |
| WO | WO 2010/051032 A1 | 5/2010 | | |
| WO | WO 2010/052715 A2 | 5/2010 | | |
| WO | WO 2012/078671 A8 | 6/2012 | | |

OTHER PUBLICATIONS

Orii et al., Beta-Tricalcium Phosphate (beta-TCP) Graft Combined with Bone Marrow Stromal Cells (MSCs) for Posterolateral Spine Fusion, J Med Dent Sci 2005; 52:51-57.*
Ogose et al., Comparison of Hydroxyapatite and Beta Tricalcium Phosphate as Bone Substitutes After Excision of Bone Tumors, J. Biomed Mater Res Part B: Appl Biomater 72B:94-101, 2005.*
Stemcell Technologies product description for Human Bone Marrow Stromal Cells, Frozen, Cat No. 70022, 2014 (made of record).*
Cheng et al., A new protocol for high-yield purification of recombinant human CXCL8(3-72)K11R/G31P expressed in *Escherichia coli*, Prot Expression and Purif 61 (2008) 65-72.*
Handl et al., Hitting multiple targets with multimeric ligands, Expert Opin. Ther. Targets (2004) 8(6) 565-586.*
Cho et al., The Effects of Synthetic Peptide Derived from hBMP-2 on Bone Formation in Rabbit Calvarial Defect, Tiss Eng and Regen Med. vol. 5, No. 3, pp. 488-497, 2008.*

(Continued)

*Primary Examiner* — Karlheinz R. Skowronek
*Assistant Examiner* — Joseph Fischer
(74) *Attorney, Agent, or Firm* — Hamilton, Brook, Smith & Reynolds, P.C.

(57) ABSTRACT

The invention is directed to a composition comprising all or a portion of a beta-tricalcium phosphate (β-TCP) bound to all or a portion of a β-TCP binding peptide and methods of use thereof.

19 Claims, 40 Drawing Sheets

Specification includes a Sequence Listing.

(56) References Cited

OTHER PUBLICATIONS

Rieker and Hu, Molecular Applications of Fusions to Leucine Zippers, Meth. Enzym. vol. 328, pp. 282-296, 2000.*
Carrodeguas, R.G. and DeAza, S., α-Tricalcium Phosphate: Synthesis, properties and biomedical applications, Acta Biomaterialia, 7 (3536-3546). 2011.
Dudak, F. C. et al., Enhancing the Affinity of SEB-Binding Peptides by Repeating their Sequence, PeptideScience, 98:2 (145-154), www.wileyonlinelibrary.com, Dec. 9, 2011.
Glick, Gary D. et al., Ligand Recognition by Influenza Virus, The Journal of Biological Chemistry, 266:35 (23660-23669), Dec. 15, 1991.
Kitov, Pavel I. et al., Optimization of Tether Length in Nonglycosidically Linked Bivalent Ligands That Target Sites 2 and 1 of a Shiga-like Toxin, J. Am. Chem. Soc., 125 (3284-3294), 2003.
Krueger, Andrew T. et al., Tailoring Chimeric Ligands for Studying and Biasing ErbB Receptor Family Interactions, Angew. Chem. Int. Ed., vol. 53 (2662-2666), 2014.
Pickens, Jason C. et al., Nonspanning Bivalent Ligands as Improved Surface Receptor Binding Inhibitors of the Cholera Toxin B Pentamer, Chemistry & Biology, vol. 11 (1205-1215), Sep. 2004.
Seker, Urartu O.S. et al., Quantitative Affinity of Genetically Engineered Repeating Polypeptides to Inorganic Surfaces, Biomacromolecules, vol. 10 (250-257), 2009.
Yashima et al, "Crystal structure analysis of β-tricalcium phosphate $Ca_3(PO_4)_2$ by neutron powder diffraction," *Journal of Solid State Chemistry*, vol. 175, Issue 2, pp. 272-277 (2003).
Dickens et al, "Crystallographic Studies of the Role of Mg as a Stabilizing Impurity in $β-Ca_3(PO_4)_2$, I. The Crystal Structure of Pure $β-Ca_3(PO_4)_2$," *Journal of Solid State Chemistry*, vol. 10, Issue 3, pp. 232-248 (1974).
Dudak, et al., "Enhancing the Affinity of SEB-Binding Peptides by Repeating Their Sequence," Peptide Science, vol. 98, No. 2, pp. 145-154, Dec. 2011.
Seker, et al., "Quantitative Affinity of Genetically Engineered Repeating Polypeptides to Inorganic Surfaces," Biomacromolecules, vol. 10, No. 2, pp. 250-257, Dec. 2008.
Nuschke, et al., "Epidermal Growth Factor Tethered to β-Tricalcium Phosphate Bone Scaffolds via a High-Affinity Binding Peptide Enhances Survival of Human Mesenchymal Stem Cells/Multipotent Stromal Cells in an Immune-Competent Parafascial Implantation Assay in Mice," Stem Cells Translation Medicine, vol. 5, pp. 1-7, Jul. 2016.
Alvarez, L.M., et al., "Tethering of Epidermal Growth Factor (EGF) to Beta Tricalcium Phosphate (BetaTCP) via Fusion to a High Affinity, Multimeric BetaTCP-Binding Peptide: Effects on Human Multipotent Stromal Cells/Connective Tissue Progenitors," PLOS One, 10(6): e0129600, pp. 1-21 (Jun. 2015).
Bateman, J., et al., "Platelet-derived Growth Factor Enhancement of Two Alloplastic Bone Matrices", *J. Periodontol*, 76(11): 1833-1841 (2005).
Bradshaw, A.D., et al., "Sparc-Null Mice Exhibit Increased Adiposity Without Significant Differences in Overall Body Weight", *PNAS*, 100(10): 6045-6050 (2003).
Bublil, E.M. and Yarden, Y., "The EGF Receptor Family: Spearheading a Merger of Signaling and Therapeutics", *Current Opinion in Cell Biology*, 19: 124-134 (2007).
Chan, S.-Y., and Wing-Chuen, R, "Expression of Epidermal Growth Factor in Transgenic Mice Causes Growth Retardation", *Journal of Biological Chemistry*, 275(49): 38693-38698 (2000).
Citri, A. and Yarden, Y., "EGF-ERBB Signalling: Towards the Systems Level", *Molecular Cell Biology*, 7: 505-516 (2006).
Erbe, E.M., et al., "Potential of an Ultraporous β-Tricalcium Phosphate Synthetic Cancellous Bone Void Filler and Bone Marrow Aspirate Composite Graft", *Eur. Spine J.*, 10: S141-S146 (2001).
Fan, V. H., et al., "Tethered Epidermal Growth Factor Provides a Survival Advantage to Mesenchymal Stem Cells", *Stem Cells*, 25: 1241-1251 (2007).

Fleming, Jr., J.E., 0, "Intraoperative Harvest and Concentration of Human Bone Marrow Osteoprogenitors for Enhnacement of Spinal Fusion." In *Orthopedic Tissue Engineering Basic Science and Practice*, V.M. Goldberg and A.I Caplan eds. (NY: Marcel Dekker, Inc.), pp. 51-65 (2004).
Freeman, M., "Reiterative Use of the EGF Receptor Triggers Differentiation of All Cell Types in the *Drosophila* Eye", *Cell*, 87: 651-660 (1996).
Friedlaender, G.E., et al., "Osteogenic Protein-1 (Bone Morphogenetic Protein-7) in the Treatment of Tibial Nonunions", *J. Bone Joint Surg. Am.*, 83-A Suppl 1(Pt 2): S151-S158 (2001).
Gao, Y., et al., "Molecular Cloning, Structure, Expression, and Chomosomal Localization of the Human Osterix (SP7) Gene", *Gene*, 2341: 101-110 (2004).
Gibbs, S., et al., "Epidermal Growth Factor and Keratinocyte Growth Factor Differentially Regulate Epidermal Migration, Growth, and Differentiation", *Wound Repair and Regeneration*, 8(3): 192-203 (2000).
Griffith, L.G., "Emerging Design Principles in Biomaterials and Scaffolds for Tissue Engineering", *Ann. N.Y. Acad. Sci.*, 961: 83-95 (2002).
Gronthos, S. and Simmons, P.J., "The Growth Factor Requirements of STRO-1-Positive Human Bone Marrow Stromal Precursosrs Under Serum-Deprived Conditions In Vitro", *Blood*, 85(4): 929-940 (1995).
Hoang, Q.Q, et al., "Bone Recognition Mechanism of Porcine Osteocalcin From Crystal Structure", *Nature*, 425: 977-980 (2003).
Jay, S.M., et al., "Engineered Bivalent Ligands to Bias ErbB Receptor-Mediated Signaling and Phenotypes", *J. Biol. Chem.*, 286: 27729-27740 (2011).
Kenan, D.J., et al., "Peptide-PEG Amphiphiles as Brief Communication Cytophobic Coatings for Mammalian and Bacterial Cells", *Chemistry & Biology*, 13: 695-700 (2006).
Kimura, A., et al., "Effects of Platelet Derived Growth Factor, Epidermal Growth Factor and Transforming Growth Factor-β on the Growth of Human Bone Marrow Fibroblasts", *British Journal of Haematology*, 69(1): 9-12 (1988).
Kratchmarova, I., et al., "Mechanism of Divergent Growth Factor Effects in Mesenchymal Stem Cell Differentiation", *Science*, 308: 1472-1477 (2005).
Kuhl, P.R. and Griffith-Cima, L.G., "Tethered Epidermal Growth Factor as a Paradigm for Growth Factor-Induced Stimulation From the Solid Phase", *Nature Medicine*, 2(9): 1022-1027 (1996).
Kuznetsov, S.A., et al., "Factors Required for Bone Marrow Stromal Fibroblast Colony Formation In Vitro", *British Journal of Haematology*, 97: 561-570 (1997).
Maheshwari, G., et al., "Biophysical Integration of Effects of Epidermal Growth Factor and Fibronectin on Fibroblast Migration", *Biophysical Journal*, 76: 2814-2823 (1999).
Marcantonio, N.A., et al., "The Influence of Tethered Epidermal Growth Factor on connective Tissue Progenitor Colony Formation", *Biomaterials*, 30(27): 4629-4638 (2009).
Matsubara, T., et al., "BMP2 Regulates Osterix Through Msx2 and Runx2 During Osteoblast Differentiation", *J. Biol. Chem.*, 283: 29119-29125 (2008).
Mehta, G., et al., "Synergistic Effects of Tethered Growth Factors and Adhesion Ligands on DNA Synthesis and Function of Primary Hepatocytes Cultured on Soft Synthetic Hydrogels", *Biomaterials*, 31(17): 4657-4671 (2010).
Miettinen, P.J., et al., "Epidermal Growth Factor Receptor Function Is Necessary for Normal Craniofacial Development and Palate Closure", *Nature Genetics*, 22: 69-73 (1999).
Mikami, Y., et al., "Inductive Effects of Dexamethasone on the Mineralization and the Osteoblastic Gene Expressions in Mature Osteoblast-Like ROS17/2.8 Cells", *Biochem Biophys Res Comm*, 362(2): 368-372 (2007).
Moll, J.R., et al., "Designed Heterodimerizing Leucine Zippers With a Range of pIs and Stabilities Up to $10^{-15}$ M", *Protein Science*, 10: 649-655 (2001).
Muschler, G.F., et al., "Engineering Principles of Clinical Cell-Based Tissue Engineering", *J Bone Joint Surg.*, 86-A(7): 1541-1558 (2004).

(56) References Cited

OTHER PUBLICATIONS

Owen, M.E., et al., "Clonal Analysis In Vitro of Osteogenic Differentiation of Marrow DFU-F", *J Cell Science*, 87: 731-738 (1987).
Pinkas-Kramarski, R., et al., "Diversification of Neu Differentiation Factor and Epidermal Growth Factor Signaling by Combinatorial Receptor Interactions", *The EMBO Journal*, 15(10): 2452-2467 (1996).
Platt, M.O., et al., "Sustained Epidermal Growth Factor Receptor Levels and Activation by Tethered Ligand Binding Enhances Osteogenic Differentiation of Multi-Potent Marrow Stromal Cells", *J. Cell Physiol.*, 221(2): 306-317 (2009).
Qin, L., et al., "Amphiregulin Is a Novel Growth Factor Involved in Normal Bone Development and in the Cellular Response to Parathyroid Hormone Stimulation", *J Biol. Chem.*, 280: 3974-3981 (2005).
Sanghvi, A.B., et al., "Biomaterials Functionalization Using a Novel Peptide That Selectively Binds to a Conducting Polymer", *Nature Materials*, 4: 496-502 (2005).
Satomura, K., et al., "Receptor Tyrosine Kinase Expression in Human Bone Marrow Stromal Cells", *J. Cell. Physiol.*, 177(3): 426-438 (1998).
Segvich, S.J. (2009). Design of Peptides With Targeted Apatite and Human Bone Marrow Stromal Cell Adhesion for Bone Tissue Engineering. (Doctoral Dissertation), Proquest UMI Publication No. 3343205.
Shen, W., et al., "Tuning the Erosion Rate of Artificial Protein Hydrogels Through Control of Network Topology", *Nature Materials*, 5: 153-158 (2006).
Sibilia, M., et al., "Mice Humanized for the EGF Receptor Display Hypomorphic Phenotypes in Skin, Bone and Heart", *Development*, 130(19): 4515-4525 (2003).
Tamama, K., et al., "Epidermal Growth Factor as a Candidate for Ex Vivo Expansion of Bone Marrow-Derived Mesenchymal Stem Cells", *Stem Cells*, 24: 686-695 (2006).

Termine, J.D., et al., "Osteonetin, A Bone-Specific Protein Linking Mineral to Collagen", *Cell*, 26: 99-105 (1981).
Tokumaru, S., et al., "Ectodomain Shedding of Epidermal Growth FActor Receptor Ligands Is Required for Keratinocyte Migration in Cutaneous Wound Healing", *J Cell Biology*, 151(2): 209-219 (2000).
Traverse, S., et al., "EGF Triggers Neuronal Differentiation of PC12 Cells That Overexpress the EGF Receptor", *Curr Biol.*, 4(8): 694-701 (1994).
Tzahar, E., et al., "A Hierarchical Network of Interreceptor Interactions Determines Signal Transduction by Neu Differentiation Factor/Neuregulin and Epidermal Growth Factor", *Molecular and Cellular Biology*, 16(10): 5276-5287 (1996).
Wang, K., et al., "Epidermal Growth Factor Receptor-Deficient Mice Have Delayed Primary Encochondral Ossification Because of Defective Osteoclast Recruitment", *J Biol. Chem.*, 279(51): 53848-53856 (2004).
Whaley, S. R., et al., "Selection of Peptides With Semiconductor Binding Specificity for Directed Nanocrystal Assembly", *Nature*, 405: 665-668 (2000).
Zeltinger, J., et al., "Effect of Pore Size and Void Fraction on Cellular Adhesion, Proliferation, and Matrix Deposition", *Tissue Engineering*, 7(5):557-572 (2001).
Zhang, K., et al., "Artificial Polypeptide Scaffold for Protein Immobilization", *J Am Chem Soc.*, 127: 10136-10137 (2005).
Ziros, P.G., et al., "The Bone-Specific Transcriptional Regulator Cbfa1 Is a Target of Mechanical Signals in Osteoblastic Cells", *J Biol. Chem.*, 277(26): 23934-23941 (2002).
Notification of Transmittal of the International Search Report and the Written Opinion of the International Searching Authority for PCT/US2011/063592; "Tricalcium Phosphate Binding Peptides and Uses Thereof", dated Feb. 14, 2013.
Notification Concerning Transmittal of International Preliminary Report on Patentability for PCT/US2011/063592; "Tricalcium Phosphate Binding Peptides and Uses Thereof", dated Jun. 20, 2013.

\* cited by examiner

Bivalent ligand design
The formation of a bivalent structure is mediated by a tight binding coiled coil interaction. This permits the formation of various bivalent ligand compositions.

TheriForm 3DP Platform
The schematic shows a thin layer of biomaterial being spread (Stage 1) onto a build platform (Stage 2). Binder is deposited to the biomaterial in a programmed sequence in the shape of interest.

Photograph and scanning electron micrographs of a Therics Therilok β-TCP scaffold; High magnification shows the detailed pore structure of these scaffolds. (Scanning electron micrographs courtesy of L. Stockdale).

Figure 3

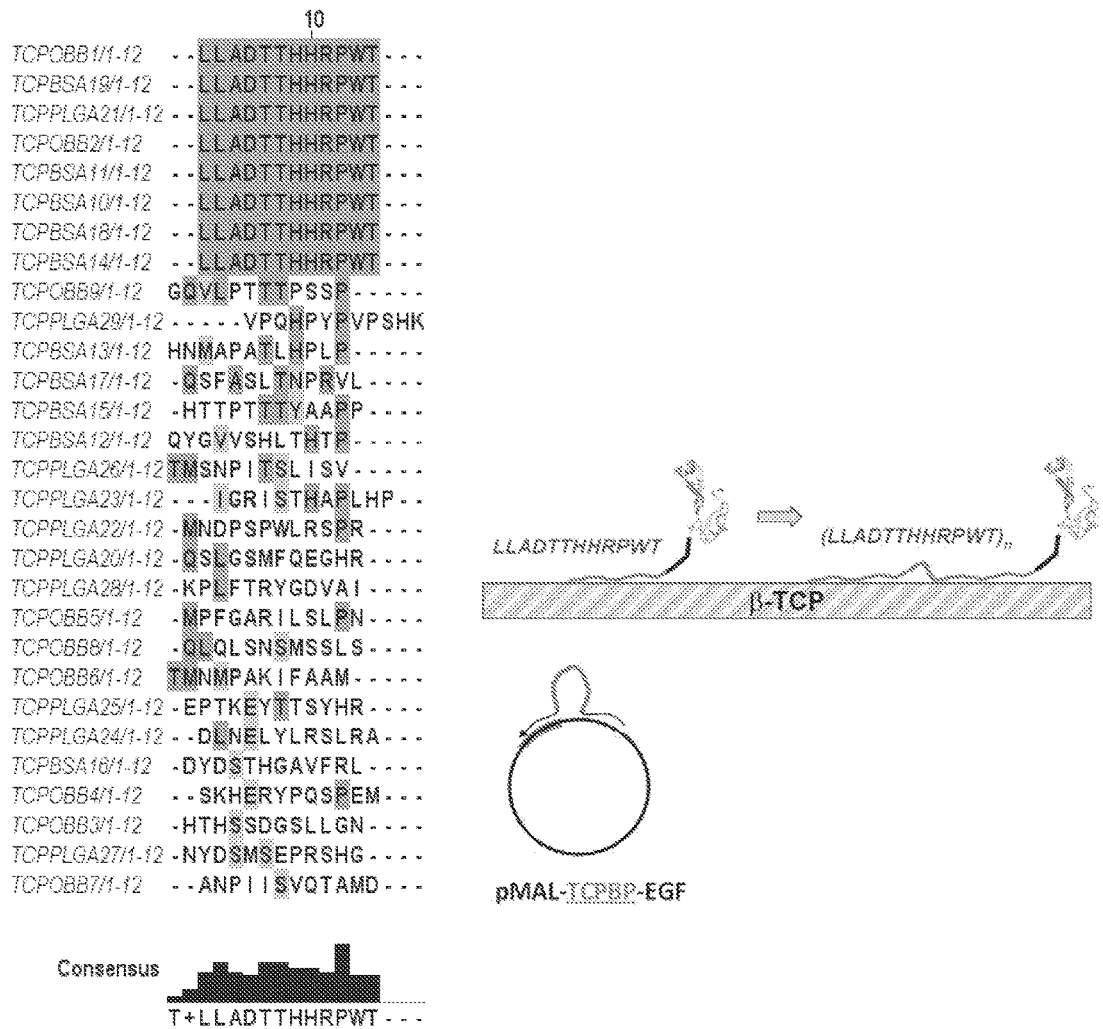

Multiple sequence alignment of phage clone sequences (left) and concatenated peptide cloning concept (right)

A strong consensus sequence is immediately evident from the alignment. Eight of 29 sequences are identical (28%). Shading is based on the BLOSUM62 score. Concatenation of multiple TCPBP regions results in increased affinity for bTCP. Generation of concatenated multimers with a primer which contains the TCPBP coding region wholly within the primer with no flanking sequences facilitates the creation of multiple insertion clones per PCR reaction.

TCPBP binding characterization
(left) Immunofluorscence micrograph of TCPBP-EGF binding to sieved TCP powder treated with (TCPBP)$_5$-EGF or a control protein lacking the TCPBP region. All images are 3 second exposures. Incubations performed at (i) 10 µM and (ii) 1 µM (TCPBP)5-EGF, and (iii) 10 µM control EGF.

Figures 5A – 5D

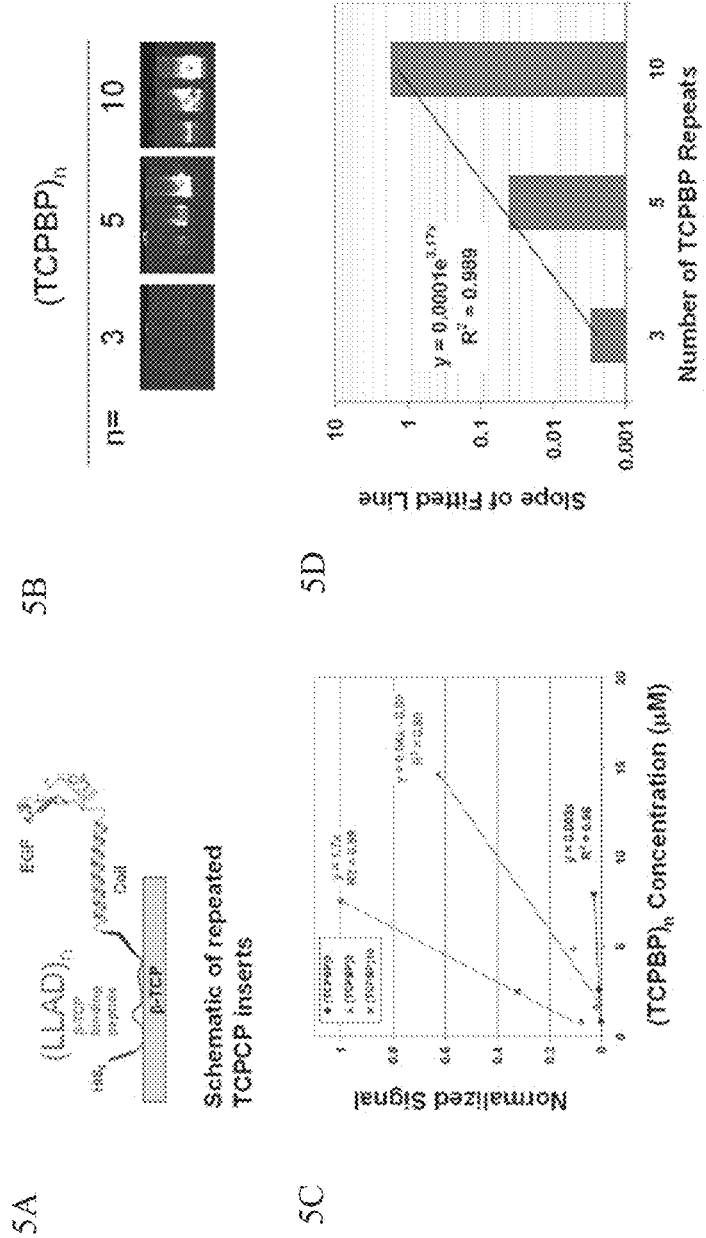

Affinity of TCPBP for BTCP with increasing number of TCPBP repeats
(A) Clones incorporating 3, 5, and 10 repeats of the TCPCP sequence were assayed for binding to TCP.
(B) Bound protein was eluted from scaffolds and assayed by SDS-PAGE & immunoblot.
(C) Desitometry of bands from immunoblots reveals increasing amounts of recovered protein for the same incubation concentration of TCPBP as the number of TCPBP repeats is increased.
(D) The slope of the fitted lines plotted versus number of repeats reveals a strong dependence on TCPBP repeat number.

Quantification of (TCPBP)10-EGF affinity for BTCP
(A) Two microliters of standard curve dilutions of (TCPBP)10-EGF and control EGF were spotted onto nitrocellulose membranes and probed with goat-a-EGF 1° and a-goat-IRDye800 2° antibodies.
(B) Spot intensity was correlated with the amount of protein spotted to find
(C) the linear range used for further quantification: 0 to 900 ng.

FIGS. 7A-7C

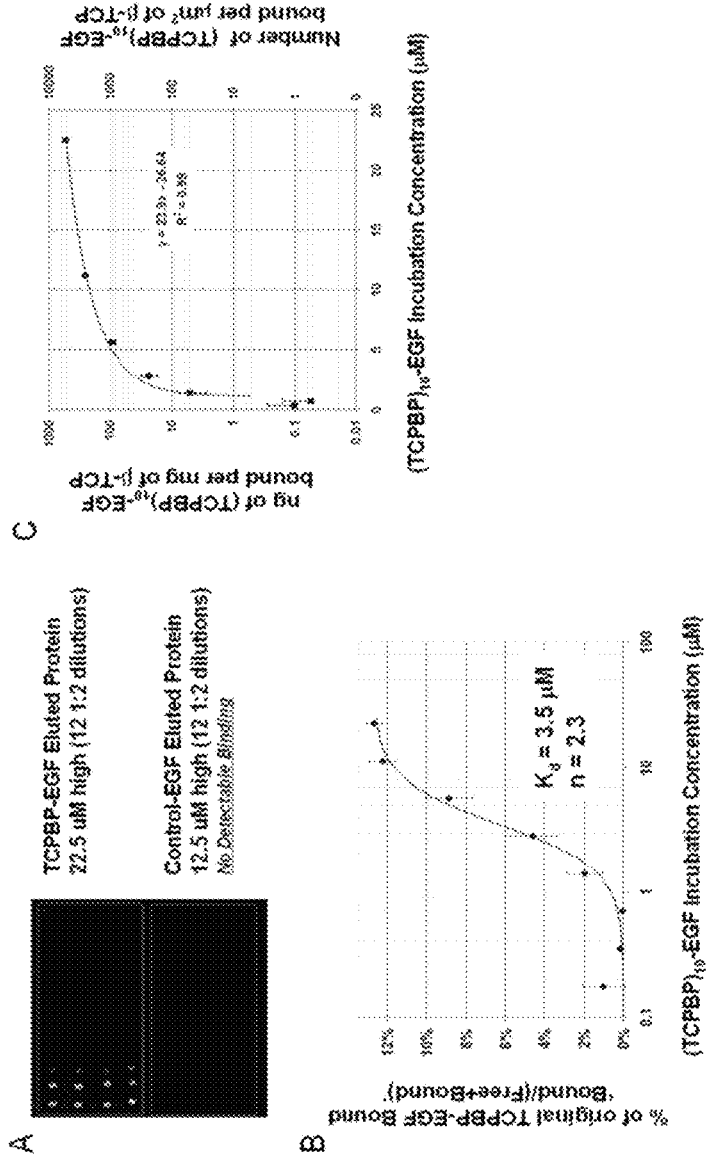

Quantification of (TCPBP)10-EGF affinity for BTCP
(A) Two microliters of eluted (TCPBP)10-EGF or eluted control EGF were spotted onto nitrocellulose membranes and probed with goat-a-EGF 1o and a-goat-IRDye800 2o antibodies. No eluted control protein was detected.
(B) Eluted protein fraction was quantified and plotted as a function of incubation concentration. A two parameter binding model was fit to the data: apparent $K_d$ = 3.5 μM, Hill coefficient = 2.3, indicative of avidity.
(C) Binding capacity of BTCP at various concentrations of (TCPBP)10-EGF. This curve can be used to tune the surface density of (TCPBP)10-EGF on BTCP by selecting the appropriate incubation concentration.

Standard curves for the Alamar Blue based cell proliferation assay Correlations between cell number and Alamar Blue fluorescence under each culture condition were used to calibrate results for 3D cultures at each day time point up to 7 days. Cell cultured in osteogenic medium exhibited smaller changes in slope over time.

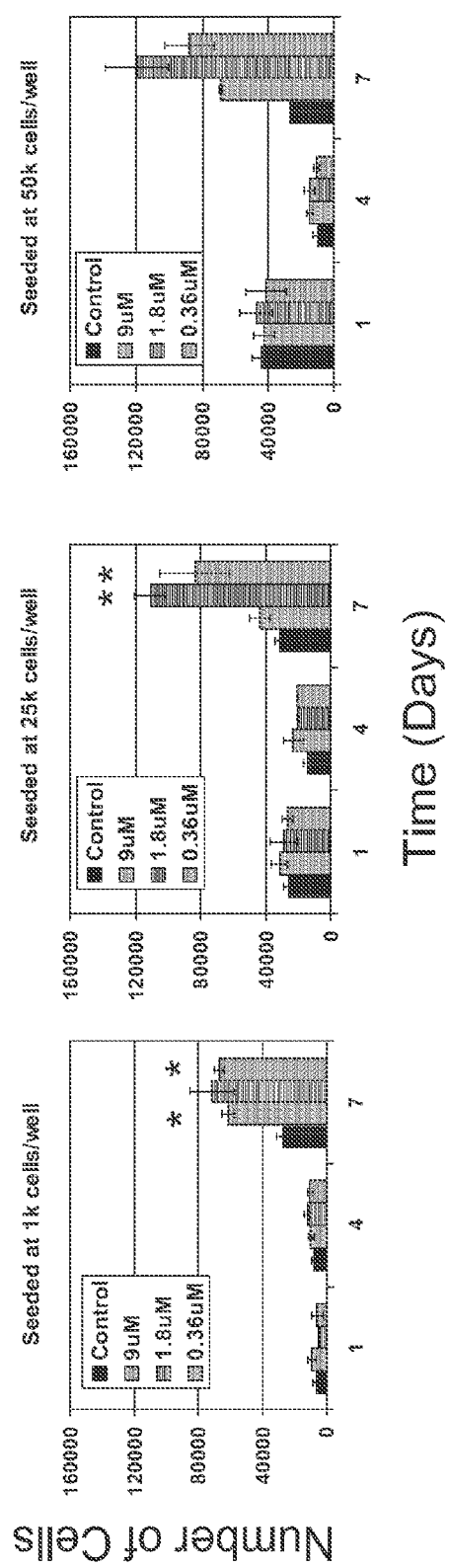

Figure 9

Proliferation of MSCs in expansion medium in 3D TCP scaffolds at various cell seeding densities and EGF(TCPBP)$_{10}$ tethering concentrations All scaffolds incubated in EX medium and assayed at terminal endpoints using the Alamar Blue based cell proliferation assay. Cell proliferation at high seeding densities (50K) exhibited a sharp minimum at day 4. This effect is attenuated as seeding density is reduced. Cell proliferation exhibited a biphasic relationship with respect to surface EGF(TCPBP)$_{10}$ tethering density at all seeding densities. The tethering concentrations studied correspond to surface densities of 2,000; 400; and 60 EGF molecules / µm$^2$; * p=0.05 vs same day control, n=6, +/- s.d.

Proliferation of MSCs on 3D TCP scaffolds
tEGF promotes MSC proliferation in both EX and OS medium. Under OS conditions increases of 62% and 25% at days 7 and 14, respectively, are observed for MSCs cultured on scaffolds treated with tEGF. n=6, +/- s.d. *p=0.05 vs respective control.

Figure 11

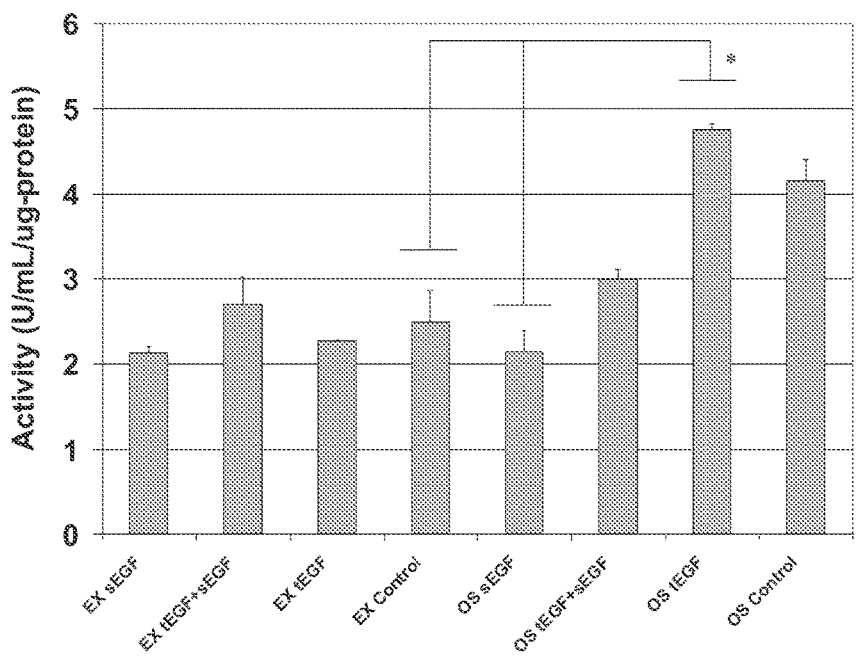

Alkaline phosphatase activity assay (Day 7)
Alkaline phosphatase activity of primary human MSCs cultured on 3D TCP scaffolds under the indicated conditions. Cells cultured in the tEGF OS condition exhibit ALP activity that is comparable to that of OS alone. Significantly, sEGF compromises this effect by lowering ALP activity. OS tEGF is significantly different that EX control or OS+sEGF at p=0.05. n=3, +/- s.d. (sEGF is soluble EGF at 1 ng/mL, tEGF is TCP treated with TCPBP as described previously.)

Figure 12

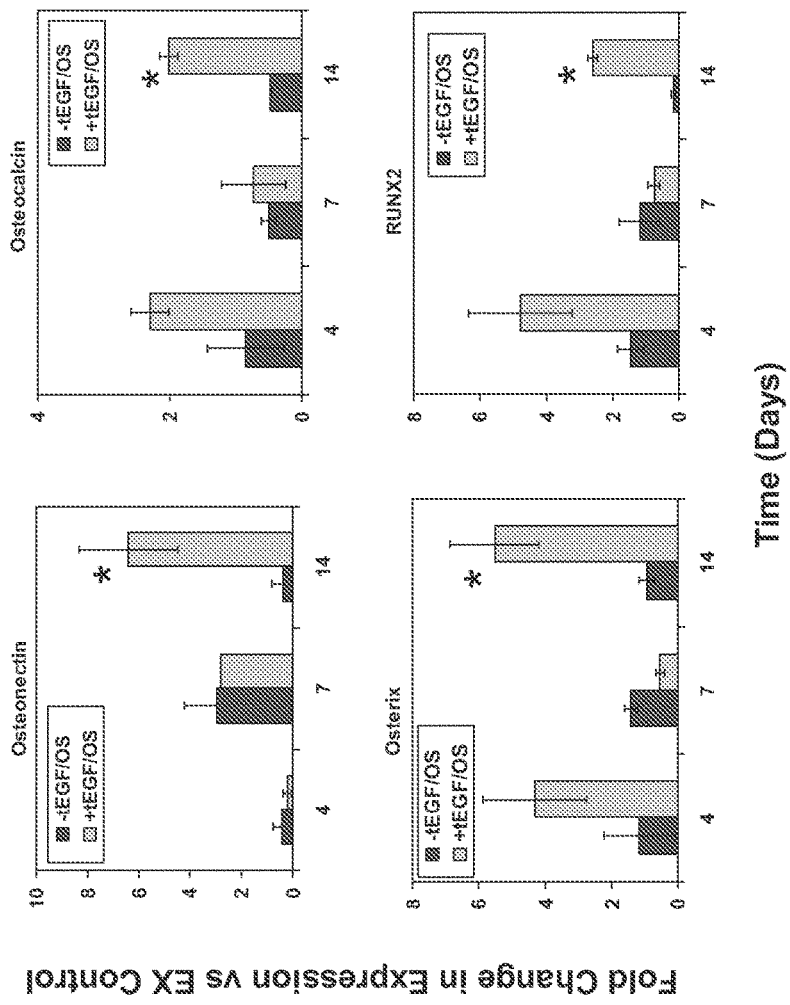

Timecourse of qRT-PCR of osteogenic markers
qRT-PCR data on a set of four osteogenic markers: osteonectin, osteocalcin, osterix, and RUNX2 at days 4, 7, and 14 illustrates the effect of tethered EGF on expression levels of early osteogenic differentiation markers. All four markers exhibit statistically significant upregulation at day 14 ($p<0.05$) vs EX control. n=3 biological and m=3 technical replicates, +/- s.d.

Figures 13A and 13B

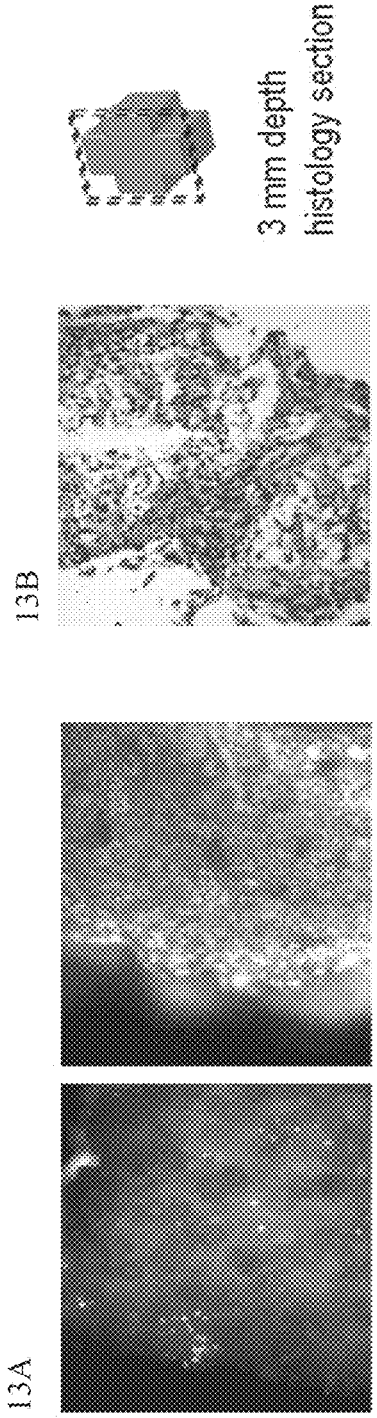

Long term survival of htMSCs under serum starvation and tEGF
(A) Surface treatment of BTCP with (TCPBP)5-EGF promotes the survival of htMSC cells cultured in serum free medium for 23 days as seen with Cytox-16 nuclear DNA stain. Untreated scaffolds exhibit evidence of cell debris and do not exhibit viable cell nuclei. (B) Hoechst and eosin stain of paraffin embedded histology sections of scaffolds treated with (TCPBP)5-EGF show deep penetration of cells into pore structure and morphology consistent with viable htMSCs. Histological analysis of untreated scaffolds did not reveal any cell in-growth.

Figure 14A

General Description

Protein Translation of pMAL-c2x-C1NC
Entire molecule length: 556 aa

Feature Map
    Cleavage Site (2 total)
        Factor Xa
            Start: 384   End: 387
        Thrombin
            Start: 410   End: 410
    Misc. Feature (3 total)
        HIS Tag
            Start: 397   End: 402
        Thrombin Recognition
            Start: 406   End: 411
        BAP
            Start: 414   End: 427
    EGF (1 total)
        EGF
            Start: 502   End: 556
    Coiled coil (1 total)
        Coil RR
            Start: 431   End: 477

Analysis
    Protein Properties

| Analysis | Entire Protein |
|---|---|
| Length | 556 aa |
| Molecular Weight | 61108.04 m.w. |
| 1 microgram = | 16.364 pMoles |
| Molar Extinction coefficient | 97160 |
| 1 A[280] corr. to | 0.63 mg/ml |
| A[280] of 1 mg/ml | 1.59 AU |
| Isoelectric Point | 5.81 |
| Charge at pH 7 | -9.08 |

Sequence
      1 mkieegklvi wingdkgyng laevgkkfek dtgikvtveh pdkleekfpq
     51 vaatgdgpdi ifwahdrfgg yaqsgllaei tpdkafqdkl ypftwdavry
   101 ngkliaypia vealsliynk dllpnppktw eeipaldkel kakgksalmf
   151 nlqepyftwp liaadggyaf kyengkydik dvgvdnagak agltflvdli
   201 knkhmmadtd ysiaeaafnk getamtingp wawsnidtsk vnygvtvlpt
   251 fkgqpskpfv gvlsaginaa spnkelakef lenylltdeg leavnkdkpl
   301 gavalksyee elakdpriaa tmenaqkgei mpnipqmsaf wyavrtavin
   351 aasgrqtvde alkdaqtnss snnnnnnnnn nlgiegrise fgsgsshhhh
   401 hhssglvprg shmglndife aqkiewhwts kgggleiraa flrrrntalr
   451 trvaelrqrv qrlrnivsqy etrygpltga sgaggseggg seggtsgatg
   501 ansdseepls hdgyclhdgv cmyiealdky acncvvgyig ercqyrdlkw
   551 welrle (SEQ ID NO: 24)

Translation of pMAL-c2x-C1NC
556 aa

Figure 14B

General Description
    Protein Translation of pMAL-c2x-C2NC
    Entire molecule length: 540 aa
Feature Map
    Cleavage Site (1 total)
        Xa
            Start: 384   End: 387
    Misc. Feature (1 total)
        Spacer
            Start: 449   End: 470
    EGF (1 total)
        EGF
            Start: 392   End: 446
    Coiled coil (1 total)
        Coil EE
            Start: 471   End: 517
Analysis
    Protein Properties

| Analysis | Entire Protein |
|---|---|
| Length | 540 aa |
| Molecular Weight | 59133.71 m.w. |
| 1 microgram = | 16.911 pMoles |
| Molar Extinction coefficient | 85780 |
| 1 A[280] corr. to | 0.69 mg/ml |
| A[280] of 1 mg/ml | 1.45 AU |
| Isoelectric Point | 4.76 |
| Charge at pH 7 | -25.75 |

Sequence
      1 mkieegklvi wingdkgyng laevgkkfek dtgikvtveh pdkleekfpq
     51 vaatgdgpdi ifwahdrfgg yaqsgllaei tpdkafqdkl ypftwdavry
    101 ngkliaypia vealsliynk dllpnppktw eeipaldkel kakgksalmf
    151 nlqepyftwp liaadggyaf kyengkydik dvgvdnagak agltflvdli
    201 knkhmnadtd ysiaeaafnk getamtingp wawsnidtsk vnygvtvlpt
    251 fkgqpskpfv gvlsaginaa spnkelakef lenylltdeg leavnkdkpl
    301 gavalksyee elakdpriaa tmenaqkgei mpnipqmsaf wyavrtavin
    351 aasgrqtvde alkdaqtnss smmnnnmmm nlgiegrise fgsnsdsecp
    401 lshdgyclhd gvcmyieald kyacncvvgy igercqyrdl kwwelrinas
    451 gaggsegggs eggtsgattg leieaafleq entaleteva eleqevqrle
    501 nivsqyetry gplgggklee qkliseedlk lgtgrrftts (SEQ ID NO: 25)

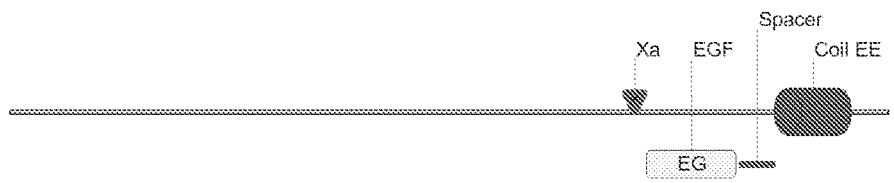

Translation of pMAL-c2x-C2NC
540 aa

Figure 14C

General Description
    Protein Translation of pMAL-c2x-EEsingleCONSTRUCT
    Entire molecule length: 248 aa Feature Map
    Site: Misc (1 total)
        R^G Thrombin Recognition    Start: 97    End: 102
    Misc. Feature (2 total)
        HIS    Start: 88    End: 93
        BAP    Start: 105    End: 118
    EGF (2 total)
        EGF    Start: 6    End: 58
        EGF    Start: 193    End: 247
    Coiled coil (1 total)
        Coil RR    Start: 122    End: 168

Analysis
    Protein Properties

| Analysis | Entire Protein |
| --- | --- |
| Length | 248 aa |
| Molecular Weight | 27038.54 m.w. |
| 1 microgram = | 36.984 pMoles |
| Molar Extinction coefficient | 50940 |
| 1 A[280] corr. to | 0.53 mg/ml |
| A[280] of 1 mg/ml | 1.88 AU |
| Isoelectric Point | 6.18 |
| Charge at pH 7 | -4.27 |

Sequence
    1 risefnsdse cplshdgycl hdgvemyiea ldkyacncvv gyigercqyr
    51 dlkwwelrin asgaggsegg gseggtsgat tggsgsshhh hhhssglvpr
    101 gshmglndif eaqkiewhwt skgggleira aflrrrntal rtrvaelrqr
    151 vqrlrnivsq yetrygpltg asgaggsegg gseggtsgat gansdsecpl
    201 shdgyclhdg vemyiealdk yacnevvgyi gercqyrdlk wwelrle* (SEQ ID NO: 26)

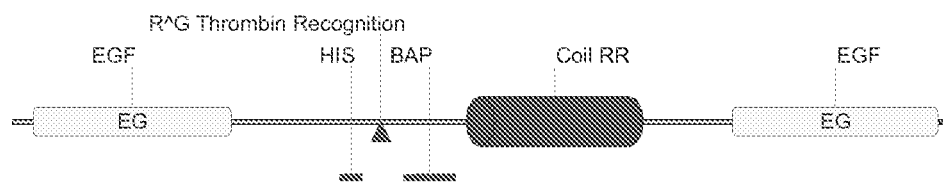

pMAL-c2x-EE EGF-EGF Single Construct
248 aa

Figure 14D

General Description
    Protein Translation of pMAL-EN EGF-NRG Single Construct
    Entire molecule length: 267 aa
Feature Map
    Cleavage Site (1 total)
        Thrombin
            Start: 116   End: 121
    Misc. Feature (2 total)
        HIS6
            Start: 107   End: 112
        BAP
            Start: 124   End: 137
    Domain: Misc (1 total)
        NRG1b
            Start: 6    End: 79
    EGF (1 total)
        EGF
            Start: 212   End: 264
    Coiled coil (1 total)
        Coil RR
            Start: 141   End: 187
Analysis
    Protein Properties

| Analysis | Entire Protein |
|---|---|
| Length | 267 aa |
| Molecular Weight | 29115.05 m.w. |
| 1 microgram = | 34.346 pMoles |
| Molar Extinction coefficient | 38280 |
| 1 A[280] corr. to | 0.76 mg/ml |
| A[280] of 1 mg/ml | 1.31 AU |
| Isoelectric Point | 6.67 |
| Charge at pH 7 | -1.26 |

Sequence
      1 risefgtshl vkcackcktf cvnggccfmv kdlsnpsryl ckcpncftgd
     51 rcqnyvmasf ykhlgiefme aeelyqkina sgaggseggg seggtsgatt
    101 ggsgsshhhh hhssglvprg shmglndife aqkiewhwts kggglciraa
    151 flrrmtalr trvaelrqrv qrlmivsqy etrygpltga sgaggseggg
    201 seggtsgatg ansdsecpls hdgyclhdgv cmyiealdky acncvvgyig
    251 ercqyrdlkw welrle* (SEQ ID NO: 27)

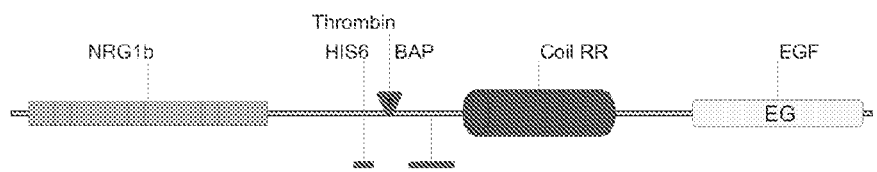

pMALc2X-EN EGF-NRG Single Construct
267 aa

Figure 14E

General Description
    Protein NRG-NRG-single constuct
    Entire molecule length: 286 aa Feature Map
    Cleavage Site (1 total)
        Thrombin
            Start: 116  End: 121
    Misc. Feature (2 total)
        HIS6
            Start: 107  End: 112
        BAP
            Start: 124  End: 137
    Domain: Misc (2 total)
        NRG1b
            Start: 6    End: 79
        NRG1b
            Start: 212  End: 285
    Coiled coil (1 total)
        Coil RR
            Start: 141  End: 187

Analysis
    Protein Properties

| Analysis | Entire Protein |
|---|---|
| Length | 286 aa |
| Molecular Weight | 31191.56 m.w. |
| 1 microgram = | 32.060 pMoles |
| Molar Extinction coefficient | 25620 |
| 1 A[280] corr. to | 1.22 mg/ml |
| A[280] of 1 mg/ml | 0.82 AU |
| Isoelectric Point | 7.67 |
| Charge at pH 7 | 1.74 |

Sequence
      1 risefgtshl vkcaekektf cvnggecfmv kdlsnpsryl ckcpneftgd
     51 rcqnyvmasf ykhlgiefme aeelyqkina sgaggseggg seggtsgatt
   101 ggsgsshhhh hhssglvprg shmglndife aqkiewhwts kgggleiraa
   151 flrrrntalr trvaclrqrv qrlrnivsqy ctrygpltga sgaggseggg
   201 seggtsgatg agtshlvkca ekektfcvng gecfmvkdls npsrylckcp
   251 neftgdrcqn yvmasfykhl giefmeaeel yqkle* (SEQ ID NO: 28)

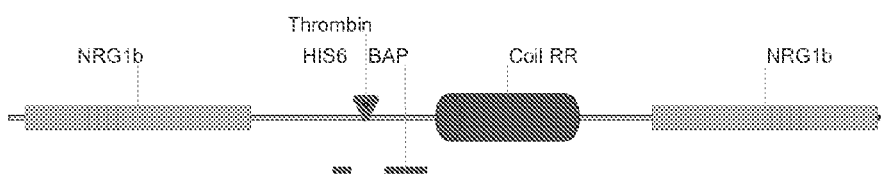

pMAL-c2x-NN NRG-NRG-single constuct

Figure 14F
General Description
    Protein Translation of pMALc2x-EGF-LLAD10
    Entire molecule length: 314 aa
Feature Map
    Cleavage Site (1 total)
        Thrombin
            Start: 30    End: 35
    Misc. Feature (3 total)
        HIS6
            Start: 2    End: 7
        S-tag
            Start: 12    End: 26
        BAP
            Start: 172    End: 185
    Binding Site: Misc (1 total)
        (TCPBP)10
            Start: 36    End: 155
    EGF (1 total)
        EGF
            Start: 260    End: 314
    Coiled coil (1 total)
        Coil RR
            Start: 189    End: 235
Analysis
    Protein Properties

| Analysis | Entire Protein |
|---|---|
| Length | 314 aa |
| Molecular Weight | 35884.04 m.w. |
| 1 microgram = | 27.868 pMoles |
| Molar Extinction coefficient | 89340 |
| 1 A[280] corr. to | 0.40 mg/ml |
| A[280] of 1 mg/ml | 2.49 AU |
| Isoelectric Point | 7.96 |
| Charge at pH 7 | 3.71 |

Sequence
      1 mhhhhhhssg mketaaakfe rqhmdspgsl vprgslladt thhrpwtlla
     51 dtthhrpwtl ladtthhrpw tlladtthhr pwtlladtth hrpwtlladt
    101 thhrpwtlla dtthhrpwtl ladtthhrpw tlladtthhr pwtlladtth
    151 hrpwtefhhh ssglvprgsh mglndifeaq kiewhwtskg ggleiraafl
    201 rrrntahtr vaelrqrvqr lrnivsqyet rygpltgasg aggsegggse
    251 sgtsgatgan sdsecplshd gyclhdgvcm yiealdkyac ncvvgyiger
    301 cqyrdlkwwe lrle (SEQ ID NO: 29)

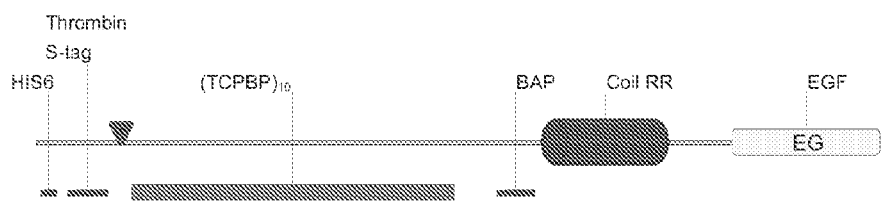

Translation of pMALc2x-EGF-LLAD10
314 aa

Figure 14G

General Description
    Protein Translation of pMALc5x-EGF- cRR-LLAD10-Ver2
    Entire molecule length: 281 aa Feature Map Binding Site: Misc (1 total)
        (TCPBP)10
            Start: 3    End: 122
    Flexible linker (2 total)
        Flexible linker
            Start: 123   End: 145
            Start: 204   End: 226
    Coiled coil (1 total)
        Coil RR
            Start: 156   End: 201
    EGF (1 total)
        EGF
            Start: 229   End: 281

Analysis
    Protein Properties

| Analysis | Entire Protein |
|---|---|
| Length | 281 aa |
| Molecular Weight | 30650.8 m.w. |
| Molar Extinction coefficient | 76805 |
| 1 A[280] corr. to | 0.40 mg/ml |
| A[280] of 1 mg/ml | 2.51 AU |
| Isoelectric Point | 7.48 |

Sequence:

1  GSLLADTTHH RPWTLLADTT HHRPWTLLAD TTHHRPWTLL ADTTHHRPWT
     51  LLADTTHHRP WTLLADTTHH RPWTLLADTT HHRPWTLLAD TTHHRPWTLL
    101  ADTTHHRPWT LLADTTHHRP WTASGAGGSE GGGSEGGTSG ATGAGTSTSG
    151  GGASTGGGLE IRAAFLRRRN TALRTRVAEL RQRVQRLRNI VSQYETRYGP
    201  LTGASGAGGS EGGGSEGGTS GATGAGTSNS DSECPLSHDG YCLHDGVCMY
    251  IEALDKYACN CVVGYIGERC QYRDLKWWEL R (SEQ ID NO: 30)

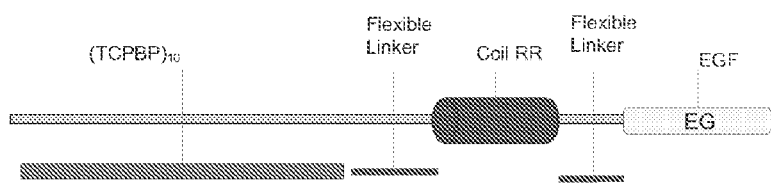

Translation of pMALc5x-EGF-cRR-LLAD10-Ver2
281 aa

Figure 14H

General Description
  Protein Translation of pMALc5x-EGF-cEE-LLAD10-Ver2
  Entire molecule length: 281 aa Feature Map Binding Site: Misc (1 total)
    (TCPBP)10
      Start: 3   End: 122
  Flexible linker (2 total)
    Flexible linker
      Start: 123   End: 145
      Start: 204   End: 226
  Coiled coil (1 total)
    Coil EE
      Start: 155   End: 201
  EGF (1 total)
    EGF
      Start: 229   End: 281

Analysis
  Protein Properties

| Analysis | Entire Protein |
|---|---|
| Length | 281 aa |
| Molecular Weight | 30463.2 m.w. |
| Molar Extinction coefficient | 76805 |
| 1 A[280] corr. to | 0.40 mg/ml |
| A[280] of 1 mg/ml | 2.52 AU |
| Isoelectric Point | 5.68 |

Sequence:

```
  1  GSLLADTTHH RPWTLLADTT HHRPWTLLAD TTHHRPWTLL ADTTHHRPWT
 51  LLADTTHHRP WTLLADTTHH RPWTLLADTT HHRPWTLLAD TTHHRPWTLL
101  ADTTHHRPWT LLADTTHHRP WTASGAGGSE GGGSEGGTSG ATGAGTSTSG
151  GGTSLEIEAA FLEQENTALE TEVAELEQEV QRLENIVSQY ETRYGPLGGG
201  KTGASGAGGS EGGGSEGGTS GATGAGTSNS DSECPLSHDG YCLHDGVCMY
251  IEALDKYACN CVVGYIGERC QYRDLKWWEL R (SEQ ID NO: 31)
```

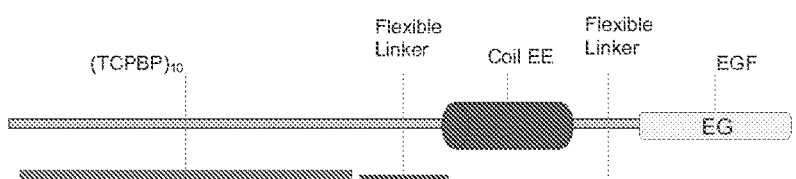

Translation of pMALc5x-EGF-cEE-LLAD10-Ver2
281 aa

Figure 17
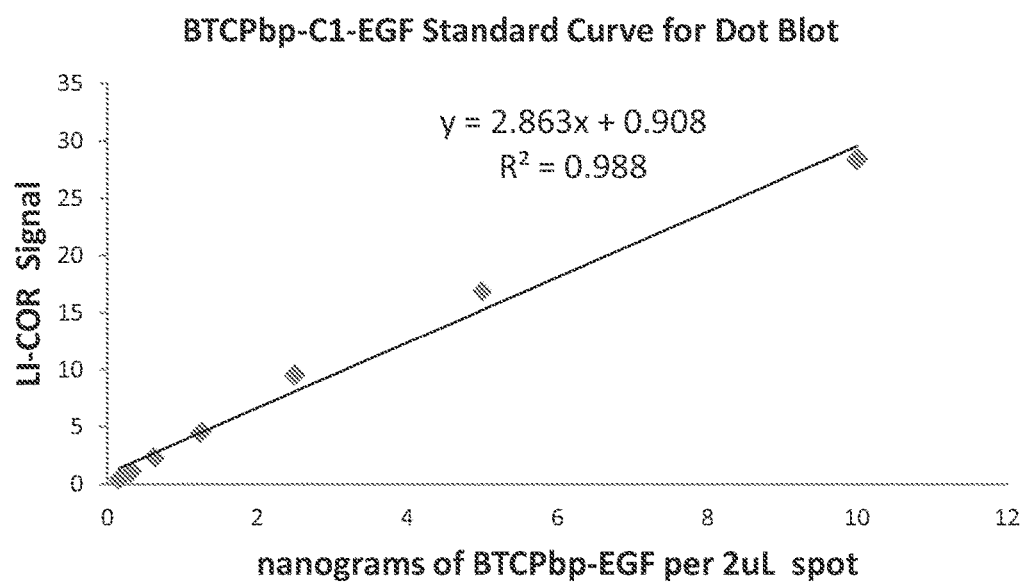
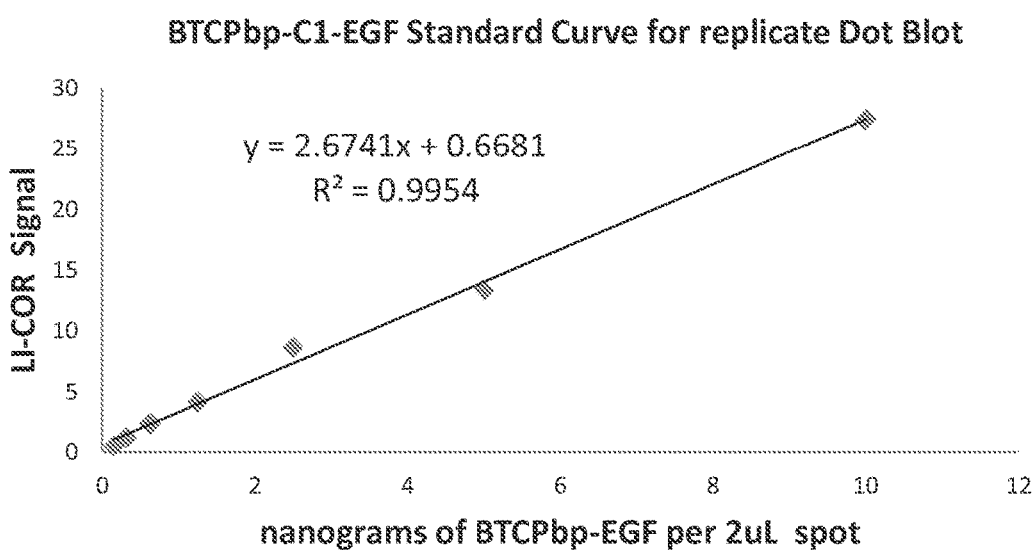

Figure 19
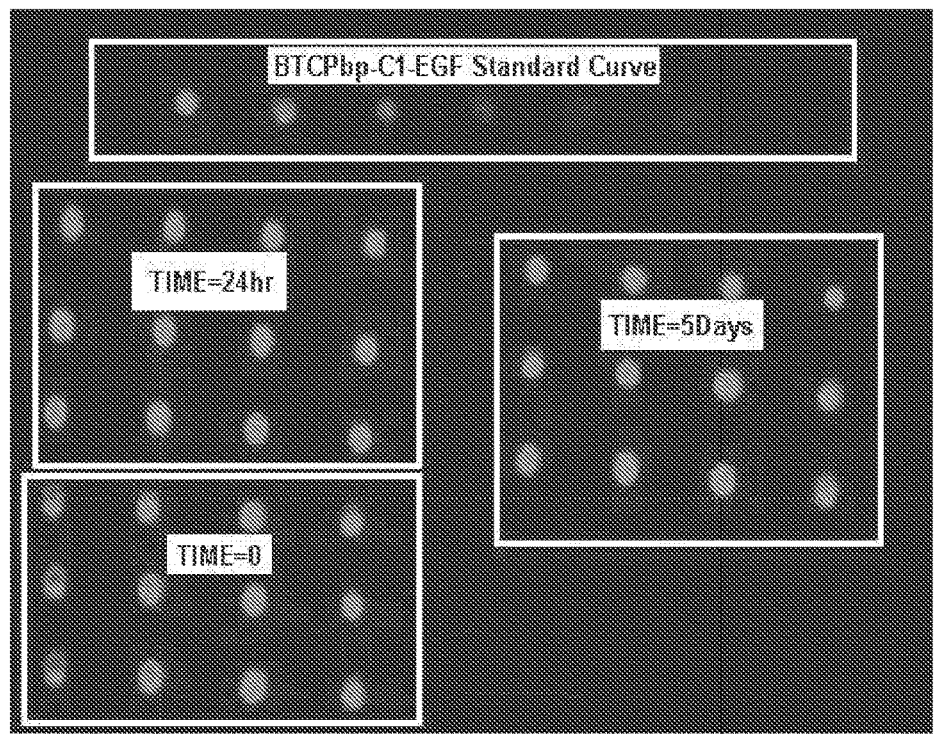
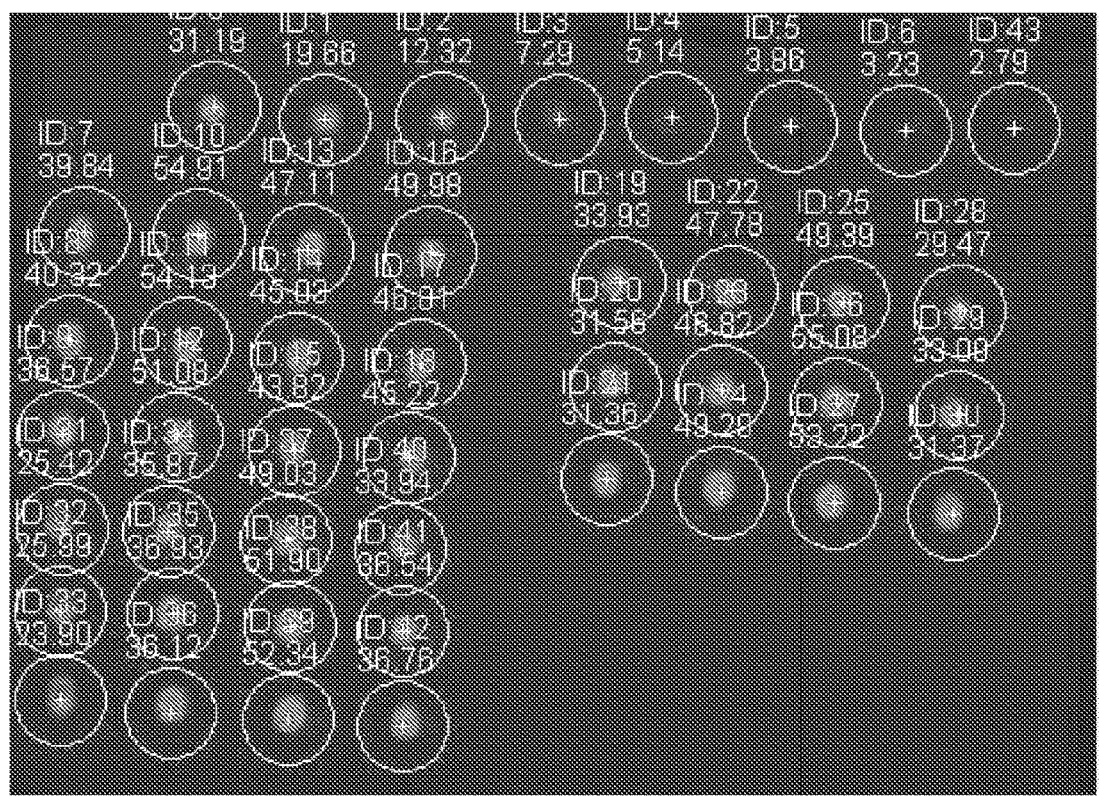

Figure 21
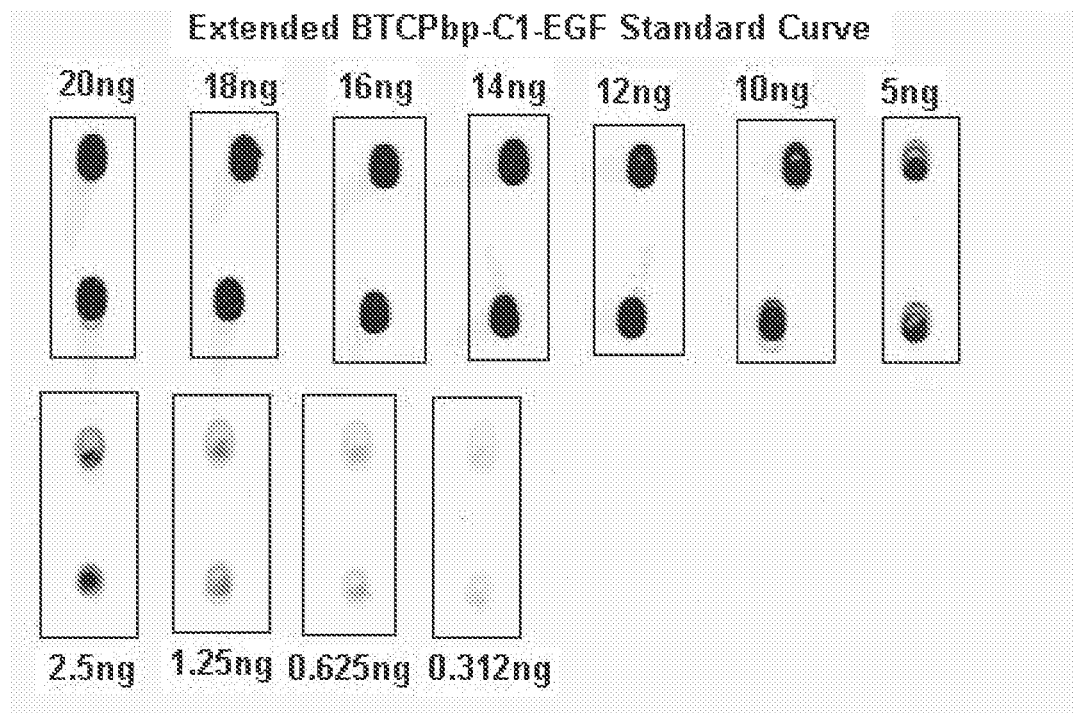
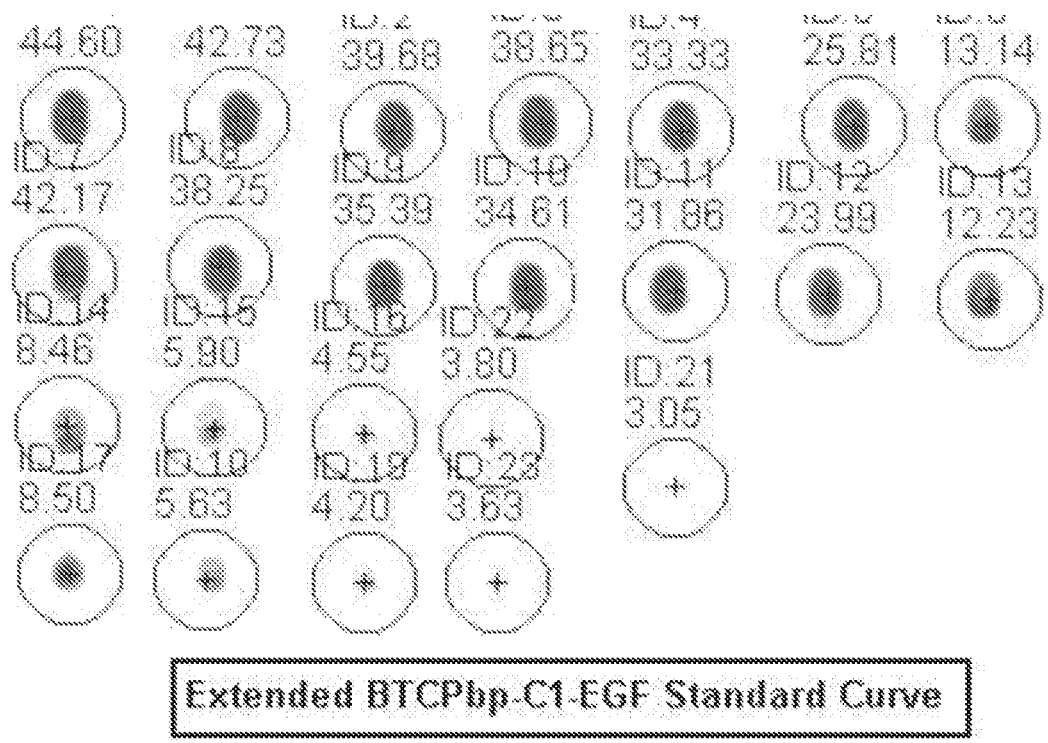

Figure 27

Homodimerization/multimerization of the C1/C2 coiled-coils could play a role on BTCPbp binding to BTCP through avidity C2-C2 coiled-coil Homodimer C1-C1 coiled-coil Homodimer $K_D = 44 \mu M$ $K_D = 250 nM$

44uM >> 2-4uM tethering concentrations >> 250nM

At 2-4 uM mostly monomeric protein; reduced affinity for BTCP substrate

At 2-4 uM mostly dimeric; increased affinity to BTCP through avidity

Top: First version of the BTCPbp-coil-EGF fusion. Middle: Clinically-relevant (CR) version of BTCPbp-EGF. CR version (2nd version) has all the foreign epitopes from 1st version removed.

Figure 29

Potentially immunogenic domains from 1st version are not present in the CR versions (2nd version)

Top: First version of the BTCPbp-coil-EGF fusion. Middle: Clinically-relevant (CR) version of BTCPbp-EGF. CR version (2nd version) has all the foreign epitopes from 1st version removed.

TRICALCIUM PHOSPHATE BINDING PEPTIDES AND USES THEREOF

RELATED APPLICATION(S)

This application is the U.S. National Stage of International Application No. PCT/US2011/063592, filed Dec. 6, 2011, which designates the U.S., published in English, and claims the benefit of U.S. Provisional Application No. 61/419,946, filed on Dec. 6, 2010.

The entire teachings of the above application are incorporated herein by reference.

GOVERNMENT SUPPORT

This invention was made with government support under Grant Nos. R10 EB003805 and RO1 DE019523 awarded by the National Institutes of Health (NIH) and under Contract No. W81XH-08-2-0034 awarded by the U.S. Army Medical Research and Material Command. The government has certain rights in the invention.

INCORPORATION BY REFERENCE OF MATERIAL IN ASCII TEXT FILE

This application incorporates by reference the Sequence Listings contained in the following ASCII text file:

a) File name 00502165002SUBSEQLIST.txt; created Sep. 19, 2013, 30 KB in size.

BACKGROUND OF THE INVENTION

Beta-tricalcium phosphate (β-TCP or BTCP) is a clinically important material with broad applications in bone repair. It is widely used in surgical procedures to fill bone voids and serves as an important material in a variety of orthopedic compositions such as putties and pastes that easily conform to wound geometries. Its continued evolution as a medical product is limited by its material properties which do not permit direct chemical surface modification and its physical properties which limit its handling.

Thus, compositions and methods for modifying the surface of BTCP to permit the design of molecular surface treatments which would extend its bio-functionality and improve clinical performance, are needed.

SUMMARY OF THE INVENTION

Described herein is the discovery of BTCP binding peptides (also referred to herein as βTCPbp or BTCPbp) and the subsequent engineering of such peptides that permits stable surface tethering of additional protein and/or peptides (e.g., epidermal growth factor) on BTCP.

The invention is exemplified herein using tethered EGF which results in increased proliferation without compromising the early differentiation of primary human MSCs cultured on 3D BTCP scaffolds. Also shown is that tethered EGF confers a strong survival advantage to MSCs cultured under serum starved conditions for prolonged periods. The compositions and methods described herein simulate the harsh conditions which can exist in a wound following surgery. As will be appreciate by those of skill in the art, the approach described here can be adapted to modify the surface of BTCP with a variety of proteins or peptides to achieve desired phenotypes.

Accordingly, in one aspect the invention is directed to a composition comprising all or a portion of a beta-tricalcium phosphate (β-TCP) bound to all or a portion of a β-TCP binding peptide. The invention is also directed to pharmaceutical compositions comprising all or a portion of a beta-tricalcium phosphate (β-TCP) bound to all or a portion of a β-TCP binding peptide.

In another aspect, the invention is directed to a method of delivering a protein and/or peptide tethered to β-TCP to an individual in need thereof comprising administering to the individual a composition comprising a β-TCP bound to a β-TCP binding peptides, wherein the β-TCP binding peptide is fused to an additional protein and/or peptide. In a particular aspect, the invention is directed to a method of delivering EGF to an individual in need thereof, comprising administering to the individual a composition comprising a β-TCP bound to a β-TCP binding peptides, wherein the β-TCP binding peptide is fused to an EGF.

In another aspect, the invention is directed to a method of repairing bone in an individual in need thereof, comprising administering to the individual a composition comprising a beta-tricalcium phosphate (β-TCP) scaffold bound to one or more β-TCP binding peptides, wherein the one or more β-TCP binding peptides are fused to EGF.

In yet another aspect, the invention is directed to a method of increasing MSC proliferation in an individual in need thereof, comprising administering to the individual MSCs and a composition comprising a β-TCP bound to one or more β-TCP binding peptides, wherein the one or more β-TCP binding peptides are fused to EGF.

In another aspect, the invention is directed to a method of culturing mesenchymal stem cells (MSCs), comprising contacting the MSCs with a composition comprising a β-TCP scaffold bound to one or more β-TCP binding peptides, wherein the one or more β-TCP binding peptides are fused to EGF, thereby producing a cell culture. The cell culture is maintained under conditions in which the MSCs proliferate, thereby culturing the MSCs. In a particular aspect the MSCs undergo differentiation. Thus, the method can further comprise assaying for differentiation of the MSCs.

BRIEF DESCRIPTION OF THE DRAWINGS

FIG. 3 shows multiple sequence alignment (SEQ ID NOs: 1-23) of phage clone sequences (left) and the concatenated peptide cloning aspect (right). A strong consensus sequence was immediately evident from the alignment. Eight of 29 sequences were identical (28%). Shading is based on the BLOSUM62 score. Concatenation of multiple TCPBP regions resulted in increased affinity for β-TCP. Generation of concatenated multimers with a primer which contains the TCPBP coding region wholly within the primer with no flanking sequences facilitated the creation of multiple insertion clones per PCR reaction.

FIGS. 5A-5D show the affinity of TCPBP for BTCP with increasing number of TCPBP repeats. FIG. 5A shows clones incorporating 3, 5, and 10 repeats of the TCPCP sequence were assayed for binding to TCP. FIG. 5B shows bound protein was eluted from scaffolds and assayed by SDS-PAGE and immunoblot. FIG. 5C shows densitometry of bands from immunoblots revealed increasing amounts of recovered protein for the same incubation concentration of TCPBP as the number of TCPBP repeats was increased. FIG. 5D shows the slope of the fitted lines plotted versus number of repeats reveals a strong dependence on TCPBP repeat number.

FIG. 6A show two microliters of standard curve dilutions of (TCPBP)10-EGF and control EGF were spotted onto nitrocellulose membranes and probed with goat-a-EGF 1° and a-goat-IRDye800 2° antibodies. FIG. 6B shows spot intensity was correlated with the amount of protein spotted to find (FIG. 6C) the linear range used for further quantification: 0 to 900 ng.

FIGS. 7A-7C shows quantification of (TCPBP)10-EGF affinity for BTCP. FIG. 7A shows two microliters of eluted (TCPBP)10-EGF or eluted control EGF were spotted onto nitrocellulose membranes and probed with goat-a-EGF 1° and a-goat-IRDye800 2° antibodies. No eluted control protein was detected. FIG. 7B shows eluted protein fraction was quantified and plotted as a function of incubation concentration. A two parameter binding model was fit to the data: apparent Kd=3.5 μM, Hill coefficient=2.3, indicative of avidity. FIG. 7C shows binding capacity of BTCP at various concentrations of (TCPBP)10-EGF. This curve can be used to tune the surface density of (TCPBP)10-EGF on BTCP by selecting the appropriate incubation concentration.

FIG. 9 shows proliferation of MSCs in expansion medium in 3D TCP scaffolds at various cell seeding densities and EGF(TCPBP)$_{10}$ tethering concentrations. All scaffolds were incubated in EX medium and assayed at terminal endpoints using the AlamarBlue® based cell proliferation assay. Cell proliferation at high seeding densities (50K) exhibited a sharp minimum at day 4. This effect was attenuated as seeding density was reduced. Cell proliferation exhibited a biphasic relationship with respect to surface EGF(TCPBP) 10 tethering density at all seeding densities. The tethering concentrations studied correspond to surface densities of 2,000; 400; and 60 EGF molecules/μm$^2$; *p=0.05 vs same day control, n=6, +/−s.d.

FIG. 11 shows alkaline phosphatase activity assay (Day 7). Alkaline phosphatase activity of primary human MSCs cultured on 3D TCP scaffolds under the indicated conditions was measured. Cells cultured in the tEGF OS condition exhibited ALP activity that was comparable to that of OS alone. Significantly, sEGF compromised this effect by lowering ALP activity. OS tEGF was significantly different than EX control or OS+sEGF at p=0.05. n=3, +/−s.d. (sEGF is soluble EGF at 1 ng/mL, tEGF is TCP treated with TCPBP as described previously.)

FIG. 12 shows a timecourse of qRT-PCR of osteogenic markers qRT-PCR data on a set of four osteogenic markers: osteonectin, osteocalcin, osterix, and RUNX2 at days 4, 7, and 14 illustrated the effect of tethered EGF on expression levels of early osteogenic differentiation markers. All four markers exhibit statistically significant upregulation at day 14 (p<0.05) vs EX control. n=3 biological and m=3 technical replicates, +/−s.d.

FIGS. 13A-13B shows long term survival of htMSCs under serum starvation and tEGF. FIG. 13A shows surface treatment of BTCP with (TCPBP)5-EGF promoted the survival of htMSC cells cultured in serum free medium for 23 days as seen with Cytox-16 nuclear DNA stain. Untreated scaffolds exhibited evidence of cell debris and did not exhibit viable cell nuclei. FIG. 13B shows Hoechst and eosin stain of paraffin embedded histology sections of scaffolds treated with (TCPBP)5-EGF showed deep penetration of cells into pore structure and morphology consistent with viable htMSCs. Histological analysis of untreated scaffolds did not reveal any cell in-growth.

FIGS. 14A-14H provides detailed design features of the polypeptides described herein.

FIG. 17 shows standard curves for the BTCPbp-C1-EGF Dot Blots. Specific amounts of BTCPbp-C1-EGF ranging from 0.156 ng to 10 ng were spotted on a nitrocellulose membrane and a standard curve was constructed for analysis of the BTCPbp-C1-EGF tethered onto 3-mm BTCP scaffolds.

FIG. 19 shows Dot Blots for the first experiment to quantify tethered BTCPbp-C1-EGF at different time points. The top image shows the dot blot without the infrared LI-COR intensity values for each spot and the bottom image is the same as the top image but with the infrared LI-COR intensity values shown for each spot. The background intensity is taken from a region without any spots and the intensity value for this blot was 2.79.

FIG. 21 shows Dot Blots corresponding to the extended BTCPbp-C1-EGF dot blot standard curve shown in FIG. 18. The top image shows the dot blot without the infrared LI-COR intensity values for each spot and the bottom image is the same as the top image but with the infrared LI-COR intensity values shown for each spot. The background intensity is taken from a region without any spots and the intensity value for this blot was 3.05. Each spot in this blot was done in duplicate.

FIG. 27 is a schematic of homodimerization/multimerization of the C1/C2 coiled-coils that play a role in BTCPbp binding to BTCP through avidity.

FIG. 29 is a graphic showing potential immunogenic domains removed from the clinically-relevant versions.

DETAILED DESCRIPTION OF THE INVENTION

Figure 1A:
FIGS. 1A-1B illustrate the ligand tethering concept using a BTXII binding peptide (TCPBP). Either single (FIG. 1A) or bivalent ligand (FIG. 1B) tethering is possible by retaining the coil region from construct C1. Construct C1 comprises human sequence of EGF domains fused to protease resistant hydrophilic spacer arms fused to coiled coil domains followed by biotinylation sequences and epitope tags. EGF can be replaced with any peptide or protein. A coiled coil domain allows for cognate coil containing ligands to form a bivalent structure. The coil sequences are selected from previously published work and have been reported by several investigators to exhibit $K_d$ as low as $10^{-15}$ M (Moll, J. R., et al., *Protein Science*, 10:649 (2001); Zhang, K., et al. *J. Am. Chem. Soc.*, 127:10136-10137 (2005); Shen, W., et al., *Nat. Mater.*, 5:153-158 (2006). The formation of a bivalent structure is mediated by a tight binding coiled coil interaction. This permits the formation of various multivalent ligand compositions.
Figure 1B:
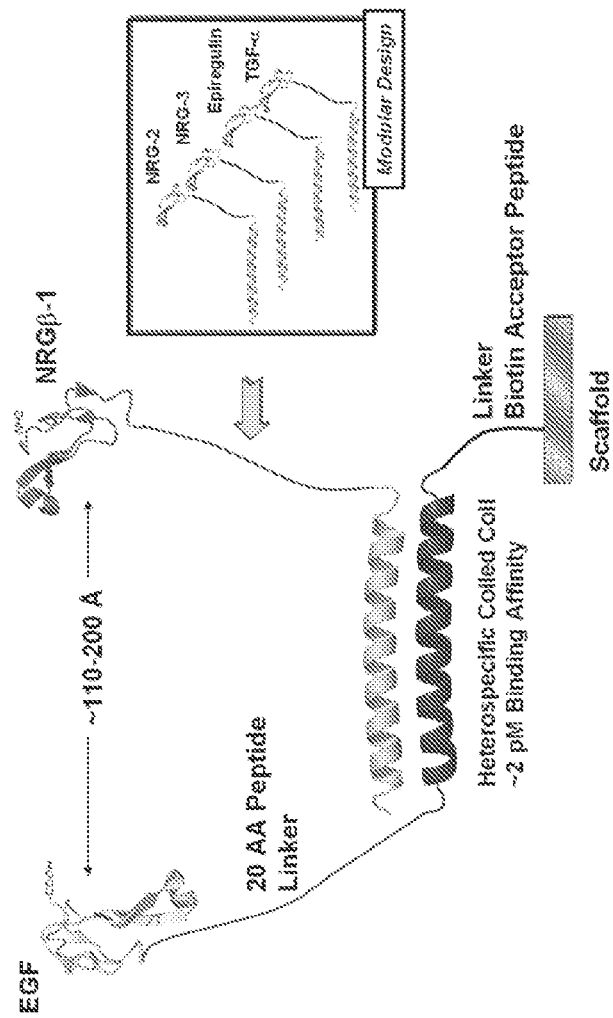

Described herein is the discovery of BTCP binding peptides or proteins. The approach taken to address this problem was to discover peptide sequences that exhibit tight binding to BTCP by using phage display (Whaley, S. R. et al., Nature 405, 665-668 (2000); Sanghvi, A. B. et al., Nature Materials 4, 496-502 (2005); Kenan, D J. et al. Chemistry & Biology 13, 695-700 (2006)). Also described herein is the use of sequences discovered through phage display as fusion partners to confer tight binding of protein ligands to BTCP substrates. Particular aspects of the invention are illustrated in FIG. 1 and include features from single ligand and multivalent (e.g., bivalent) ligand designs.

Compositions

Accordingly, in one aspect the invention is directed to a composition comprising all or a portion of a beta-tricalcium phosphate (β-TCP) bound to all or a portion of a β-TCP binding peptide. In other aspects, the invention is directed to a composition consisting essentially of, or consisting of, all or a portion of a beta-tricalcium phosphate (β-TCP) bound to all or a portion of a β-TCP binding peptide.

Sintering tricalcium phosphate, $Ca_3(PO_4)_2$, causes its structure to convert to β-TCP. As used herein, "β-TCP", or "BTCP", refers to a sintered tricalcium phosphate that functions as an osteoconductive material that supports bone mineralization by easily dissolving at low pH and serves as a rigid substrate for cell attachment (Muschler, G. P. et al., The Journal of Bone and Joint Surgery 86, 1541-1558 (2004); Fleming Jr, J. E., George, F., Muschler, C. B. & Isador, H. Intraoperative Harvest and Concentration of Human Bone Marrow Osteoprogenitors for Enhancement of Spinal Fusion. Orthopedic Tissue Engineering: Basic Science and Practice (2004)). Muschler and others have used this in conjunction with autologously harvested bone marrow to improve outcomes. In those kinds of procedures the BTCP is flushed with bone marrow aspirate to seed MSCs and further promote bone formation (Fleming Jr, J. E., George, F., Muschler, c. B. & Isador, H. Intraoperative Harvest and Concentration of Human Bone Marrow Osteoprogenitors for Enhancement of Spinal Fusion. Orthopedic Tissue Engineering: Basic Science and Practice (2004)).

As used herein an "osteoconductive material" includes a material that facilitates the formation of bone structure (e.g., bone grafts); has the ability to serve as a structure on which bone cells can attach, migrate, grow and divide; supports bone mineralization and the like.

As will be appreciated by those of skill in the art, the β-TCP can be used in a variety of forms. Examples of such forms include a granular form, a porous form, a powder, a putty (e.g., a moldable putty), a paste and/or a scaffold. In addition, the β-TCP can be used in a variety of shapes (e.g., a cross, a ladder, a circle, a square, a triangle, etc.) and sizes (e.g., about 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 7 cm, 8 cm, 9 cm, 10 cm, etc.). In particular embodiments, the β-TCP is porous (e.g., about 20%, 25%, 30%, 35%, 40%, 45%, 50%, 55%, 60%, 65%). In other embodiments, the β-TCP has a pore size of about 20 μm, 30 μm, 40 μm, 50 μm, 60 μm, 70 μm, 80 μm, 90 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 1 mm, 10 mm, 20 mm, 30 mm, 40 mm, 50 mm). In one aspect, the β-TCP is about 60% porous with a mean pore diameter of about 60 microns and a pore diameter range of about 5, 10, 20, 30, 40, 50, 60, 70, 80, 90, 100, 150, 200, 250, 300, 350, 400, 450, 500, 550, 600, 650, 700, 750, 800, 850, 900 microns. In addition and as will be appreciated by those of skill in the art, the BTCP can comprise additional elements such as progens. An example of a porogen is sucrose.

As used herein "β-TCP binding peptides" (or "TCPBPs") are peptides that specifically bind to β-TCP. In one aspect, the β-TCP binding peptide binds tightly to, or has a high affinity for, β-TCP. As used herein, a "high affinity" refers to a binding affinity of about 3 μm, 2.8 μm, 2.6 μm, 2.4 μm, 2.2 μm, 2.0 μm, 1.8 μm, 1.6 μm, 1.4 μm, 1.2 μm, 1.0 μm, 0.8 μm, 0.6 μm, 0.4 μm, 0.2 μm, 100 nanomoles, 80 nmol, 60 nmol, 40 nmol, 20 nmol, 10 nmol, 1 nmol, 800 picomol, 600 picomol, 400 picomol, 200 picomol, 100 picomol, 80 picomol, 60 picomol, 40 picomol, 20 picomol, 10 picomol or 1 picomol. In a particular aspect, the kD is 2.3 uM for (TCPBP)10.

As will be appreciated by those of skill in the art, higher affinities can be achieved by modifying a polypeptide to increase its affinity for its binding partner. For example, adding β-TCP binding peptides to the composition; directed mutagenesis of the β-TCP binding peptide(s) or the linker(s) between β-TCP binding peptide (e.g., using a low number of amino acids between each β-TCP binding peptide); and/or error prone polymerase chain reaction (PCR) (e.g., to introduce sequences that make the peptide more flexible) can be used to obtain higher affinities.

In one aspect, a β-TCP binding peptide binds to a β-TCP non covalently. In other aspects, the β-TCP binding protein is also capable of binding (e.g., fusing) to an (one or more) additional protein and/or peptide, e.g., thereby tethering an additional (one or more) protein and/or peptide to β-TCP.

In particular aspects, the β-TCP binding peptide comprises the amino acid sequence LLADTTHHRPWT (SEQ ID NO: 1), GQVLPTTTPSSP (SEQ ID NO: 2), VPQHPYPVPSHK (SEQ ID NO: 3), HNMAPATLHPLP (SEQ ID NO: 4), QSFASLTNPRVL (SEQ ID NO: 5), HTTPTTTYAAPP (SEQ ID NO: 6), QYGVVSHLTHTP (SEQ ID NO: 7), TMSNPITSLISV (SEQ ID NO: 8), IGRISTHAPLHP (SEQ ID NO: 9), MNDPSPWLRSPR (SEQ ID NO: 10), QSLGSMFQEGHR (SEQ ID NO: 11), KPLFTRYGDVAI (SEQ ID NO: 12), MPFGARILSLPN (SEQ ID NO: 13), QLQLSNSMSSLS (SEQ ID NO: 14), TMNMPAKIFAAM (SEQ ID NO: 15), EPTKEYTTSYHR (SEQ ID NO: 16), DLNELYLRSLRA (SEQ ID NO: 17), DYDSTHGAVFRL (SEQ ID NO: 18), SKHERYPQSPEM (SEQ ID NO: 19), HTHSSDGSLLGN (SEQ ID NO: 20), NYDSMSEPRSHG (SEQ ID NO: 21), or ANPIISVQTAMD (SEQ ID NO: 22).

In other aspects, the β-TCP binding peptide comprises an amino acid sequence that has about 70%, 75%, 80%, 85%, 90%, 95%, 96%, 97%, 98% or 99% identity with LLADTTHHRPWT (SEQ ID NO: 1), GQVLPTTTPSSP (SEQ ID NO: 2), VPQHPYPVPSHK (SEQ ID NO: 3), HNMAPATLHPLP (SEQ ID NO: 4), QSFASLTNPRVL (SEQ ID NO: 5), HTTPTTTYAAPP (SEQ ID NO: 6), QYGVVSHLTHTP (SEQ ID NO: 7), TMSNPITSLISV (SEQ ID NO: 8), IGRISTHAPLHP (SEQ ID NO: 9), MNDPSPWLRSPR (SEQ ID NO: 10), QSLGSMFQEGHR (SEQ ID NO: 11), KPLFTRYGDVAI (SEQ ID NO: 12), MPFGARILSLPN (SEQ ID NO: 13), QLQLSNSMSSLS (SEQ ID NO: 14), TMNMPAKIFAAM (SEQ ID NO: 15), EPTKEYTTSYHR (SEQ ID NO: 16), DLNELYLRSLRA (SEQ ID NO: 17), DYDSTHGAVFRL (SEQ ID NO: 18), SKHERYPQSPEM (SEQ ID NO: 19), HTHSSDGSLLGN (SEQ ID NO: 20), NYDSMSEPRSHG (SEQ ID NO: 21), or ANPIISVQTAMD (SEQ ID NO: 22).

Portions of β-TCP binding peptides that bind to all or a portion of β-TCP can also be used in the compositions and methods provided herein. Such portions include a portion of the β-TCP binding peptide that binds to all or a portion of a β-TCP. In particular embodiments, the portion of the β-TCP binding peptide is also capable of binding (e.g., fusing) to an (one or more) additional protein and/or peptide, e.g., thereby tethering an additional (one or more) protein and/or peptide to β-TCP. For example, as will be appreciated by those of skill in the art, a portion of a β-TCP binding peptide includes a peptide comprising one of the sequences provided herein (e.g., SEQ ID NOs: 1-22) wherein an (one or more) N terminal or a (one or more) C terminal amino acid has been removed.

As will be apparent to those of skill in the art, variants of the sequences of the β-TCP peptides can be used in the compositions and methods provided herein. Such variants can be naturally-occurring, such as in the case of allelic variation or single nucleotide polymorphisms, or non-naturally-occurring, such as those induced by various mutagens and mutagenic processes. Intended variations include, but are not limited to, addition, deletion, and substitution of one or more nucleotides or amino acids that can result in conservative or non-conservative amino acid changes, including additions and deletions. Preferably, the amino acid changes are silent or conserved; that is, they do not alter the characteristics or activity of the β-TCP binding peptide. For example, amino acid residues that are conservative substitutions for corresponding residues are those that are physically or functionally similar to the residue being substituted, e.g., that have similar size, shape, charge, chemical properties (i.e., the ability to form covalent or hydrogen bonds). Conservative substitutions typically include the substitution of one amino acid for another with similar characteristics, such as substitutions within the following groups: valine glycine; glycine, alanine; valine, isoleucine, leucine; aspartic acid, glutamic acid; aspargine, glutamine; serine, threonine; lysine, arginine; and phenylalanine, tyrosine.

Another aspect of the invention is directed to compositions comprising, consisting essentially of, or consisting of an (one or more) isolated β-TCP binding peptide, portions thereof and variants thereof as described herein. "Isolated" refers to a substantially isolated BTCPbp with respect to the complex (e.g., cellular) milieu in which it occurs such as isolated from an organ, body, tissue, blood, or culture medium. In some instances, the isolated material will form part of a composition (for example, a crude extract containing other substances), buffer system, culture system or reagent mix. In other circumstances, the material can be purified to essential homogeneity.

In particular aspects, the invention is directed to compositions comprising, consisting essentially of, or consisting of a β-TCP binding peptide comprising the amino acid sequence LLADTTHHRPWT (SEQ ID NO: 1), GQVLPTTTPSSP (SEQ ID NO: 2), VPQHPYPVPSHK (SEQ ID NO: 3), HNMAPATLHPLP (SEQ ID NO: 4), QSFASLTNPRVL (SEQ ID NO: 5), HTTPTTTYAAPP (SEQ ID NO: 6), QYGVVSHLTHTP (SEQ ID NO: 7), TMSNPITSLISV (SEQ ID NO: 8), IGRISTHAPLHP (SEQ ID NO: 9), MNDPSPWLRSPR (SEQ ID NO: 10), QSLGSMFQEGHR (SEQ ID NO: 11), KPLFTRYGDVAI (SEQ ID NO: 12), MPFGARILSLPN (SEQ ID NO: 13), QLQLSNSMSSLS (SEQ ID NO: 14), TMNMPAKIFAAM (SEQ ID NO: 15), EPTKEYTTSYHR (SEQ ID NO: 16), DLNELYLRSLRA (SEQ ID NO: 17), DYDSTHGAVFRL (SEQ ID NO: 18), SKHERYPQSPEM (SEQ ID NO: 19), HTHSSDGSLLGN (SEQ ID NO: 20), NYDSMSEPRSHG (SEQ ID NO: 21), or ANPIISVQTAMD (SEQ ID NO: 22), portions and variants thereof.

In other aspects, the invention is directed to isolated β-TCP binding peptides that comprise an amino acid sequence that has about 70%, 75%, 80%, 85%, 90%, 95%, 96%, 97%, 98% or 99% identity with LLADTTHHRPWT (SEQ ID NO: 1), GQVLPTTTPSSP (SEQ ID NO: 2), VPQHPYPVPSHK (SEQ ID NO: 3), HNMAPATLHPLP (SEQ ID NO: 4), QSFASLTNPRVL (SEQ ID NO: 5), HTTPTTTYAAPP (SEQ ID NO: 6), QYGVVSHLTHTP (SEQ ID NO: 7), TMSNPITSLISV (SEQ ID NO: 8), IGRISTHAPLHP (SEQ ID NO: 9), MNDPSPWLRSPR (SEQ ID NO: 10), QSLGSMFQEGHR (SEQ ID NO: 11), KPLFTRYGDVAI (SEQ ID NO: 12), MPFGARILSLPN (SEQ ID NO: 13), QLQLSNSMSSLS (SEQ ID NO: 14), TMNMPAKIFAAM (SEQ ID NO: 15), EPTKEYTTSYHR (SEQ ID NO: 16), DLNELYLRSLRA (SEQ ID NO: 17), DYDSTHGAVFRL (SEQ ID NO: 18), SKHERYPQSPEM (SEQ ID NO: 19), HTHSSDGSLLGN (SEQ ID NO: 20), NYDSMSEPRSHG (SEQ ID NO: 21), or ANPIISVQTAMD (SEQ ID NO: 22).

Such portions and variants of the β-TCP binding peptide can be made using the guidance provided herein and routine skills known to those of skill in the art. In addition, using the guidance provided herein and routine skills known to those of skill in the art such portions and variants of the β-TCP binding peptide can be assessed for binding to β-TCP (e.g., specific binding). Examples of assays to detect binding include antibody based assays, cell based assays (e.g., a proliferation assay), radioimmunoassay, and Kaiser protein assays.

As will be appreciated by those of skill in the art, one or more β-TCPs binding peptides can be bound to one or more β-TCPs. In some aspects, one or more β-TCP binding proteins are bound to a single β-TCP. In other aspects, one or more β-TCP binding proteins are bound to one or more β-TCPs. In particular aspects, the invention is directed to compositions of concatenated multimers or repeats comprising at least two repeats of a unit (repeating units), wherein each unit comprises a β-TCP binding peptide bound to a β-TCP (See FIG. 3). As will be appreciated by those of skill in the art, the same β-TCP binding peptide can be bound to the β-TCP in each repeating unit of a single concatenated multimer. Alternatively, each unit can comprise a different β-TCP binding peptide bound to the β-TCP in a single concatenated multimer, or some of the units can have the same β-TCP binding peptide bound to the β-TCP and other units can have a different β-TCP binding peptide bound to the p-TCP in a single concatenated multimer. In some aspects, the composition is a concatenated multimer comprising about two, three, four, five, six, seven, eight, nine, ten, eleven, twelve, thirteen, fourteen, fifteen, sixteen, seventeen, eighteen, nineteen, or twenty repeats (units) of a β-TCP binding peptide bound to a β-TCP. In a particular aspect the composition is a concatenated multimer comprising ten repeats of a β-TCP binding peptide bound to a β-TCP.

As shown herein, the compositions can further comprise one or more additional peptides or proteins fused to the β-TCP binding peptide. That is, in one aspect, the composition comprises all or a portion of a beta-tricalcium phosphate (β-TCP) bound to all or a portion of a β-TCP binding peptide, wherein the β-TCP binding peptide is fused to one or more additional peptides or proteins (resulting in a monovalent or multivalent (e.g., bivalent, trivalent) design. Thus, in particular aspects, a fusion protein is created between the β-TCP binding peptide, which is bound to β-TCP, and the one or more additional proteins or peptides, thereby tethering the additional one or more proteins or peptides to the β-TCP. In other aspects, the composition comprises all or a portion of a BTCPbp fused to one or more additional peptides or proteins.

As will be appreciated by those of skill in the art a variety of proteins and/or peptides can be fused to the β-TCP binding peptide. The additional protein and/or peptide can be fused at either the N terminal end of the β-TCP binding peptide, the C terminal end of the β-TCP binding peptide or within the β-TCP binding peptide. Examples of such proteins and portions thereof (e.g., peptides) include growth factors (e.g., epidermal growth factor, platelet-derived growth factor (PDGF), IGF, FGF, TGF (TGF-α; TGF-β)), cytokines (bone morphogenetic protein (BMP), hormones, insulin, and enzymes. Specific examples include heregulin, neuregulin (NRG, such as NRGβ1), morphogenic protein stimulatory factor (MPSF), osteogenic protein (OP, such as OP-1, OP-2, OP-3), BMP-2, BMP-3, BMP-4, BMP-5, BMP-6, BMP-7, BMP-9, BMP-10, BMP-11, BMP-13, BMP-15, DPP, Vg1, Vgr, GDF-1, GDF-3, GDF-5, GDF-6, GDF-7, matrix binding proteins such as hyaluronic binding protein, and collagen binding protein. In one aspect, the additional protein is epidermal growth factor (EGF). In a particular aspect, the composition is a concatenated multimer comprising ten repeats of a β-TCP binding peptide bound to a β-TCP wherein each β-TCP binding protein is bound to an EGF.

In particular aspects, the composition provides for bivalent ligand tethering. For example, in some aspects, the design allows for bivalent tethering of the same protein or peptide (e.g., bivalent EGF (two EGFs), bivalent NRG (two NRGs)), and/or bivalent tethering of different proteins or peptides (e.g., bivalent EGF-NRG)

The ability to expand a progenitor population without compromising differentiation potential is one of the key objectives of regenerative medicine and has significant clinical implications. Because many procedures rely on autologous MSC transplantation, increasing patient native progenitor populations to improve bone wound healing is an important objective.

Many studies have characterized the effects of EGF on tissues in vitro and in vivo. EGF is the canonical ligand for the epidermal growth factor receptor (EGFR), and induction of this pathway can produce proliferation (Pinkas-Kramarski, R. et al. EMBO J 15, 2452-2467 (1996); Tzahar, E. et al. Molecular and Cellular Biology 16, 5276-5287 (1996); Tamama, K., et al., Stem Cells 24, 686 (2006); Griffith, L. G. Annals of the New York Academy of Sciences 961, 83-95 (2002); Muschler, G. P. et al., The Journal of Bone and Joint Surgery 86, 15411558 (2004); Bublil, E. M. & Yarden, Y. Current Opinion in Cell Biology 19, 124-134 (2007); Citri, A. & Yarden, Y. Nat Rev Mol Cell Biol 7, 505-516 (2006)), migration (Miettinen, P J. et al. Nature Genetics 22, 69-73 (1999); Gibbs, S. et al. Wound Repair and Regeneration 8, 192-203 (2000); Tokumaru, S. et al. The Journal of Cell Biology 151, 209-220 (2000); Maheshwari, G. et al., Biophysical Journal 76, 2814-2823 (1999)), homeostasis (Tamama, K., et al., Stem Cells 24, 686 (2006)), and synergistic effects leading to differentiation when dosed with other ligands (Traverse, S. et al. Current Biology 4, 694-701 (1994); Freeman, M. Cell 87, 651-660 (1996); Miettinen, P J. Nature Genetics, Vol. 127 (1999)). The broad effects of this ligand result from the diversity of the downstream signaling network, thus making EGF an important stimulus in wound healing contexts. In MSCs, EGF has been shown to affect a number of cell behaviors in a context specific manner. EGF can promote proliferation (Tamama, K., et al., Stem Cells 24, 686 (2006)), osteogenic differentiation (Kratchmarova, I. et al., Vol. 308 1472-1477 (American Association for the Advancement of Science, 2005)), and survival (Fan, V. H. et al. Stem Cells 25, 1241 (2007)). In a wound healing context EGF can serve as an important cue leading to bone development and homeostasis following surgery (Wang, K. et al., Journal of Biological Chemistry 279,53848 (2004); Sibilia, M. et al. Development 130, 4515-4525 (2003); Qin, L. et al. Journal of Biological Chemistry 280, 3974 (2005); Chan, S. Y. & Wong, R. W. C. Journal of Biological Chemistry 275, 38693-38698 (2000)). EGF has also been shown to play a role as a regulator of MSC behavior (Kratchmarova, I. et al., Vol. 308 1472-1477 (American Association for the Advancement of Science, 2005); Kuznetsov, S. A. et al., British Journal of Haematology 97, 561-570 (1997); Kimura, A. et al., British Journal of Haematology 69, 9-12 (1988); Gronthos, S. & Simmons, P. J. Blood 85, 929-940 (1995); Owen, M. E., Clonal analysis in vitro of osteogenic differentiation of marrow CFU-F, Vol. 87 731-738 (1987); Satomura, K. et al. Journal of Cellular Physiology 177, 426-438 (1998)) and can give rise to expansion of MSCs without inducing differentiation (Tamama, K., et al., Stem Cells 24, 686 (2006)).

The clinical utility of these effects cannot be fully exploited without a viable method to deliver EGF to sites of injury in a spatially controlled manner, particularly on clinically important substrates. One such clinically important substrate is BTCP which is routinely used in orthopedic procedures (Erbe, E. M. et al., Eur Spine J 10, S141-146 (2001)).

Although the intrinsic properties of BTCP favor bone healing in many clinical applications, addition of osteogenic growth factors BMP-2 and OP-1 to BTCP scaffolds at the time of implant enhances healing in both experimental animal models and clinical applications (Friedlaender, G. E. et al., Vol. 83 151-158 (JBJS, 2001)). As shown herein, where a source of stem and/or progenitor cells (e.g. marrow aspirate) is added to overcome a local deficiency of osteogenic cells, presentation of a tethered growth factor, e.g., EGF, enhanced cell survival and stimulated proliferation of early progenitors to populate the site, e.g., upstream of BMP activity (Fan, V. H. et al. Stem Cells 25, 1241 (2007); Marcantonio, N. A. et al., Biomaterials, 30 (27), 4629-2638 (2009); Platt, M. O. et al. J Cell Physiol (2009)). Although physisorption of PDGF to BTCP has been shown to enhance proliferation of osteogenic cells on BTCP scaffolds in vitro, the in vivo loss of growth factor is much faster than that observed in vitro (Bateman, J. et al. Journal of Periodontology 76, 1833-1841 (2005)). As shown herein, the utility of BTCP as an existing substrate for orthopedic procedures is enhanced using surface treatments described herein which permit stable attachment of bioactive components such as EGF to β-TCP.

The BTCPbp can be fused to the one or more additional proteins or peptides directly or through the use of a linker. As will be appreciated by those of skill in the art a variety of linkers can be used (e.g., see Hermanson, G. T., Bioconjugate Techniques, Academic Press, San Diego, Calif. (1996). Examples of suitable linkers include a coiled coil linker (e.g., a leucine zipper coiled coil). As shown herein, specific examples of linkers for use in the compositions include Coil C1 or "RR" and Coil C2 or "EE". RR or C1 comprises the amino acid sequence KGGGLEI RAAFLRR RNTALRT RVAELRQ RVQRLRN IVSQYET RYGPL (SEQ ID NO: 32) and EE or C2 comprises the amino acid sequence LEIEAAFLEQENTALETEVAELEQEVQR-LENIVSQYETRYGPLGGGK (SEQ ID NO: 33). Coil C1 has binding affinity for C2 of 10-15 molar. The terminal lysines (k) in these sequences are not essential, and were added to allow for conjugation chemistry. See Steven M. et al., *J Biol Chem,* 286(31), 27729-27740 (Aug. 5, 2011) and Moll, J. R. et al., *Protein Science* 10, 649 (2001).

As further shown herein, the compositions can further comprise additional components or agents (e.g., bioactive agents). For example, the compositions can further comprise a spacer such as an amino acid sequence that provides rigidity or flexibility to the composition. As will be apparent to those of skill in the art a variety of spacers can be used in the compositions described herein. An example of a spacer as described herein is a flexible, protease-resistant linker comprising the amino acid sequence: ASGA GGSE GGGSE GGTS GATGA (SEQ ID NO: 34). It is a hydrophilic, protease resistant, non-rigid spacer that allows for maximum flexibility.

As described herein, in one aspect the invention is directed to a composition comprising all or a portion of a BTCPbp bound to BTCP wherein the BTCPbp can be fused (bound to) to one or more additional peptides (proteins). In other aspects, the invention is directed to a composition comprising all or a portion of a BTCPbp fused (bound to) to one or more additional peptides (proteins). As will be appreciated by those of skill in the art, the structure of the composition can take a variety of forms. For example, in one aspect, the various components of the composition can be linked in the following way or in the following order: (i) BTCP-(BTCPbP)n where n is the number (one or more) of BTCPBps; (ii) BTCP-(BTCPbP)n-(protein or peptide)n; (iii) BTCP-(BTCPbP)n-linker-(protein or peptide)n; (iv) BTCP-(BTCPbP)n-spacer-linker-(protein or peptide)n; (vi) BTCP-(BTCPbP)n-spacer-linker-spacer-(protein or peptide)n; (vii) (BTCPbP)n-(protein or peptide)n; (viii) (BTCPbP)n-linker-(protein or peptide)n; (ix) (BTCPbP)n-spacer-linker-(protein or peptide)n; (x) (BTCPbP)n-spacer-linker-spacer-(protein or peptide)n etc.

In particular aspects, the invention is directed to a composition comprising SEQ ID NO:29, a composition comprising SEQ ID NO: 30 and a composition comprising SEQ ID NO:31.

Additionally, the composition can further comprise one or more additional sequences (e.g., protease resistant sequences, restriction enzyme recognition sites; insertion sites, splicing regions and the like), cell types or tissues. The cells and/or tissue can be of mammalian origin (e.g., primate such as human), bacterial origin (e.g., beneficial bacteria) and the like. Examples of such cell types include progenitor cells (e.g., fat derived progenitor cells), stem cells (e.g., mesenchymal stem cells (MSCs)), bone marrow cells, chondrocytes, osteocytes, osteoblasts, osteoclasts, bone progenitor cells, epithelial cells, fibroblasts, and neuronal cell (e.g., neuronal stem cells). Examples of such tissue include bone marrow, connective tissue (e.g., tendons, cartilage, ligaments), autologous bone, skin, and periostium. In particular aspects, human cells and/or tissue are used, and in yet other aspects, autologous human cells and/or tissue are used.

As also shown herein the compositions of the present invention can be obtained with endotoxin levels that are less than about 1000 EU/mg, 900 EU/mg, 800 EU/mg, 700 EU/mg, 600 EU/mg, 500 EU/mg, 400 EU/mg, 300 EU/mg, 200 EU/mg, 100 EU/mg, 50 EU/mg, or 40 EU/mg. In one embodiment, the composition can be obtained with an endotoxin level of about 38.9 EU/mg.

Methods of Producing

Producing the composition comprising a beta-tricalcium phosphate (β-TCP) bound to a β-TCP binding peptide, and compositions further comprising one or more additional proteins or peptides fused to the β-TCP binding peptide can be performed using methods described herein and routine skills. For example, as described herein, to create β-TCP scaffolds, granulated β-TCP powder was sintered, sieved and fabricated in the shape of a cross. In particular aspects, the purity of the β-TCP is about 75%, 76%, 77%, 78%, 79%, 80%, 81%, 82%, 83%, 84%, 85%, 86%, 87%, 89%, 90%, 91%, 92%, 93%, 94%, 95%, 96%, 97%, 98%, 99% or 100% pure. In other aspects, the β-TCP is made using a similar method but as a composite with other agents such as polylactide-co-glycolide (PLGA).

As will be apparent to those of skill in the art, the composition can further comprise one or more pore forming agents, referred to herein as porogens. Examples of porogens include inorganic salts such as sodium chloride, saccharides (e.g., glucose), gelatin (e.g., gelatin spheres), or paraffin (e.g., paraffin spheres).

Methods for creating a fusion protein between a β-TCP binding peptide and an additional protein or peptide are also well known to those of skill in the art. For example, this can be accomplished by cloning nucleic acid (e.g., cDNA) encoding an (one or more) additional protein or peptide into an expression vector in frame with nucleic acid encoding a (one or more) β-TCP binding peptide.

As will be apparent to those of skill in the art a variety of linkers can also be used to fuse the β-TCP binding peptide to the additional protein and/or peptide (e.g., see Hermanson, G. T., Bioconjugate Techniques, Academic Press, San Diego, Calif. (1996). Examples of suitable linkers include a coiled coil linker (e.g., a leucine zipper coiled coil).

Tethering the fusion protein between a β-TCP binding peptide and an additional protein or peptide onto β-TCP can be accomplished, for example, by contacting (e.g., incubating) the β-TCP with the fusion protein to produce a combination, and maintaining the combination under conditions in which the β-TCP binding protein of the fusion protein binds to β-TCP.

Pharmaceutical Compositions

The present invention also pertains to pharmaceutical compositions. In one aspect, the pharmaceutical composition comprises a beta-tricalcium phosphate (β-TCP) bound to a β-TCP binding peptide. In another aspect, the pharmaceutical composition comprises a beta-tricalcium phosphate (β-TCP) bound to a β-TCP binding peptide wherein an additional protein or peptide is fused to the β-TCP binding peptide. In yet another embodiment, the pharmaceutical composition comprises a beta-tricalcium phosphate (β-TCP) bound to a β-TCP binding peptide wherein an additional protein or peptide is fused to the β-TCP binding peptide, and further comprising MSCs. Pharmaceutical compositions comprising a β-TCP binding peptide are also included. As will be appreciated by those of skill in the art, pharmaceutical compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose; polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compounds are administered in a therapeutically effective amount. The amount of compounds that will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of the condition being treated, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

Methods of Use

The compositions provided herein can also be used in a variety of methods. In one aspect, the invention is directed to a method of delivering a protein and/or peptide (e.g., EGF, BMP-2, OP-1) to an individual in need thereof comprising administering to the individual an effective amount of a composition comprising one or more β-TCP bound to one or more β-TCP binding peptides, wherein the one or more β-TCP binding peptides are fused to the protein and/or peptide that is to be delivered. In a particular aspect, the invention is directed to a method of delivering EGF to an individual in need thereof, comprising administering to the individual a composition comprising a β-TCP bound to a β-TCP binding peptide, wherein the β-TCP binding peptide is fused to an EGF. The composition can be administered, for example, to a wound site, such as a bone injury. This method can further comprise administering MSCs to the individual (e.g., administered at a cell seeding density of from about 100 to about 1,000,000 MSCs per composition). The MSCs can, for example, be delivered separately or seeded onto the composition comprising a β-TCP bound to a β-TCP binding peptide.

In another aspect, the invention is directed to a method of repairing bone in an individual in need thereof, comprising administering to the individual a composition comprising a beta-tricalcium phosphate (β-TCP) scaffold bound to one or more β-TCP binding peptides, wherein the one or more β-TCP binding peptides are fused to EGF. The method can further comprise administering MSCs to the individual (e.g., administering autologous MSCs to an individual undergoing an autologous bone graft). As used herein, repairing bone includes the formation of new bone and/or cartilage.

In yet another aspect, the invention is directed to a method of increasing MSC proliferation in an individual in need thereof, comprising administering to the individual MSCs and an effective amount of a composition comprising a β-TCP bound to one or more β-TCP binding peptides, wherein the one or more β-TCP binding peptides are fused to EGF.

As discussed herein, β-TCP has been used as an osteoconductive material in vivo and thus, methods of delivering the composition to an individual in need thereof will be apparent to those of skill in the art. For example, the composition can be surgically implanted or injected into the individual in need thereof. The composition is typically administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

As used herein an individual refers to an animal, and in particular aspects, a mammal. Examples of mammals include a primate (e.g., human), canine (e.g., domestic dog) feline (e.g., domestic dog), rodents (e.g., mouse, rat), equine (e.g., horse), bovine, orvine and the like.

In another aspect, the invention is directed to a method of culturing MSCs, comprising contacting the MSCs with a composition comprising a β-TCP scaffold bound to one or more β-TCP binding peptides, wherein the one or more β-TCP binding peptides are fused to EGF, thereby producing a cell culture. A variety of seeding densities for the MSCs can be used in the method. Examples of seeding densities for use in the method include a seeding density of about 1000; 5000; 10,000; 15,000; 20,000; 25,000; 30,000; 35,000; 40,000; 45,000; 50,000; 55,000; 60,000; 65,000; 70,000; 75,000; 80,000; 85,000; 90,000; 95,000; or 100,000 cells.

The cell culture is maintained under conditions in which the MSCs proliferate, thereby culturing the MSCs. In a particular aspect the MSCs undergo differentiation. Thus, the method can further comprise assaying for differentiation of the MSCs. In particular aspects, the MSCs undergo increased proliferation of from about 20% to about 65% compared to proliferation of a control culture of MSCs. In particular aspects, the MSCs undergo increased proliferation of about 10%, 20%, 30%, 40%, 50%, 60%, or 70% compared to proliferation of a control culture of MSCs. A variety of methods for maintaining the cell culture under conditions in which the MSCs proliferate can be used and are known to those of skill in the art. Such methods include maintaining the cell culture under serum starved conditions, in an expansion medium, in an osteogenic medium or a combination thereof.

EXEMPLIFICATION

Example 1

Discovery and Application of BTCP Binding Peptides

Fabrication of BTCP and BTCP-polymer Composite Scaffolds

Figure 2A:
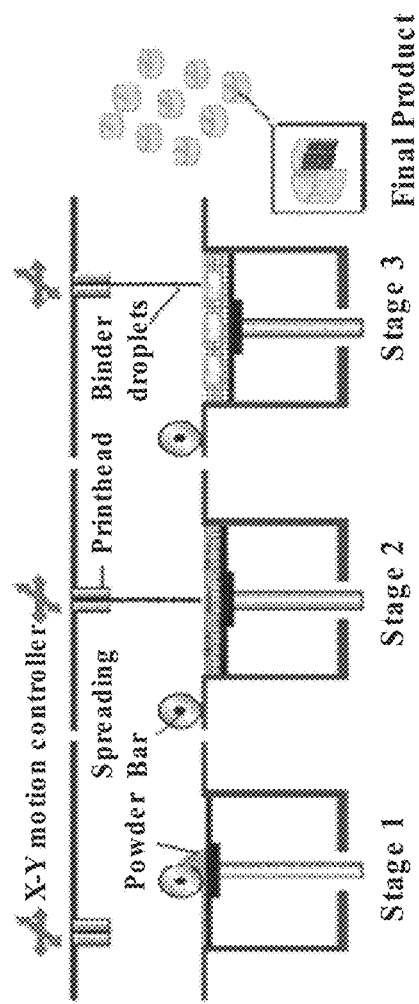
FIG. 2A shows the TheriForm™ 3DP platform; the schematic shows a thin layer of biomaterial being spread (Stage 1) onto a build platform (Stage 2). Binder is deposited to the biomaterial in a programmed sequence in the shape of interest.
Figure 2B:
FIG. 2B shows photograph and scanning electron micrographs of a Therics Therilok™ β-TCP scaffold (cross shaped implant). High magnification shows the detailed pore structure of these scaffolds. Using the 3DP platform, cross shaped TCP bone void fillers were produced. The implants are ~5×5×3 mm. The cross shape helps the graft units to interlock and provide for stable graft packing. SEM micrograph shows open spongy pore structure to facilitate bone ingrowth, wicking of blood components and nutrient transfer. Implants are approximately 60% porous and have a pore range of about 5 to about 900 microns.

Scaffolds were fabricated at Therics (Akron, Oreg.) from either BTCP or a composite of BTCP and polylactide-coglycolide (PLGA) using the TheriForm™ 3D rapid prototyping platform (Zeltinger, J. et al., Tissue engineering 7,557-572 (2001)). Briefly, to create BTCP scaffolds, granulated BTCP powder was sintered and sieved. Scaffolds were fabricated in the shape of a cross by depositing binder in a programmed sequence onto a BTCP powder bed containing a mixture of calcium phosphate and sucrose as a porogen. The scaffolds were then sintered for 20 h, dried for 1 day, leached for 2 days to remove porogen, and dried one day to yield crosses measuring 5×5×3 mm (FIG. 2B). Each implant was approximately 60% porous with a mean pore diameter of 60 microns and a pore diameter range of 5-900 microns.

The internal structure showed an open spongy type structure (FIG. 2B). When multiple crosses are packed, the packing porosity is approximately 83%. Chemically, the scaffolds were >95% BTCP with the remaining portion being other resorbable forms of calcium phosphate. Composite BTPC-PLGA scaffolds were fabricated in a similar fashion by mixing PLGA and BTCP powders with a porogen.

Phage Display Against BTCP Scaffolds

BTCP scaffolds were crushed into powder, autoclaved for 35 minutes at 121° C. and stored under dry sterile conditions prior to all experiments. The resulting sterile BTCP powder was blocked for 24 hours at 4° C. under moderate agitation with either sterile filtered salmon protein buffer (Licor) or 5% bovine serum albumin in phosphate buffered saline (BSA, Sigma). Blocked BTCP powder was pelleted at 2000 RPM for 2 minutes, washed 3× with PBS then subjected to three rounds of phage display using the New England Biolabs linear 12-mer Ph.D. kit (Andover, Mass.). Orthogonally blocked BTCP (i.e. blocked with BSA vs salmon protein) provided a control against panning against components of the blocking buffers. Additional controls included a β-TCP/PLGA composite scaffold, crushed into powder, similarly blocked with bovine serum albumin (BSA) or salmon protein buffer as well as a mock tube to control against panning against tube components. After three rounds of panning, ten plaques from each condition were picked, amplified, then sequenced (the mock condition and the BTCP/PLGA blocked with BSA did not produce plaques after the second and third round, respectively). Sequences were analyzed for consensus using JalView Multiple Sequence Alignment Editor (Schuler, G. D., Altschul, S. F. & Lipman, D J. A workbench for multiple alignment construction and analysis. Proteins: Structure, Function, and Genetics 9 (1991); Clamp, M. et al., GJ., Vol. 20426-427 (Oxford Univ Press, 2004)). FIG. 3 shows the aligned sequences.

Mutagenesis

The highest ranked sequence from third round phage display panning, LLADTTHHRPWT (SEQ ID NO:1), was serially cloned into a pMAL expression cassette using PCR mutagenesis and a short primer to generate a library of multimer insertions fused to epidermal growth factor (FIG. 3). PCR mutagenesis was performed with a Quickchange® Ligthtning II kit from Stratagene (Eugene, Oreg.). A pMAL-c2X vector (New England Biolabs) expressing human epidermal growth factor in fusion with various epitopes was constructed. See FIGS. 14A-14F. PCR primers were designed to prime wholly within the BTCP binding peptide coding region thus allowing multiple insertions during a single PCR mutagenesis round. Multimer clones were sequenced to confirm DNA identity with target sequence, transformed into BL21(DE3)pLysS E. coli and plated on ampicillin LB agar. The library evaluated included $(TCPBP)_{n=1,2,3,5,8, and 10}$ clones.

Protein Expression

Clones of 1-, 2-, 3-, 5-, 8, and 10-mers of the TCPBP sequence (LLADTTHHRPWT) were expressed in 1 L LB cultures grown at 37° C. until OD 0.6, then induced with IPTG and incubated at 22° C. for 4 hours. Proteins were harvested by pelleting cultures at 3700 RPM on an Allegra G3.8 rotor at 4° C. for 30 minutes then freezing the pellet at −80° C. overnight followed by cell lysis using Bugbuster Reagent (EMD Chemicals) supplemented with PMSF and protease inhibitor cocktail (Sigma). Lysed cells were centrifuged at 3700 RPM on an Allegra G3.8 rotor at 4° C. for 1 hour. The supernatant was then diluted 1:4 in tris buffered saline and subjected to maltose binding protein affinity chromatography in accordance with the manufacturer's instructions (New England Biolabs). Pooled fractions were subjected to ultrafiltration through a 50,000 molecular weight cutoff (MWCO) membrane V-tube concentrator (Novagen) and twice exchanged into phosphate buffered saline (PBS). Concentrated protein was sterile filtered through a 0.2 micron filter. Purity was confirmed by SDS-PAGE commassie staining. Protein quantification was performed on a Nanodrop A280 spectrophotometer. Concentrated proteins were stored at minus 80° C. until use. Based on preliminary results with 1- and 2-mers which showed modest binding affinity, the 3-, 5-, and 10-mers were selected for further evaluation.

Tethering TCPBP-EGF on BTCP Scaffolds and Binding Characterization

Figure 4:
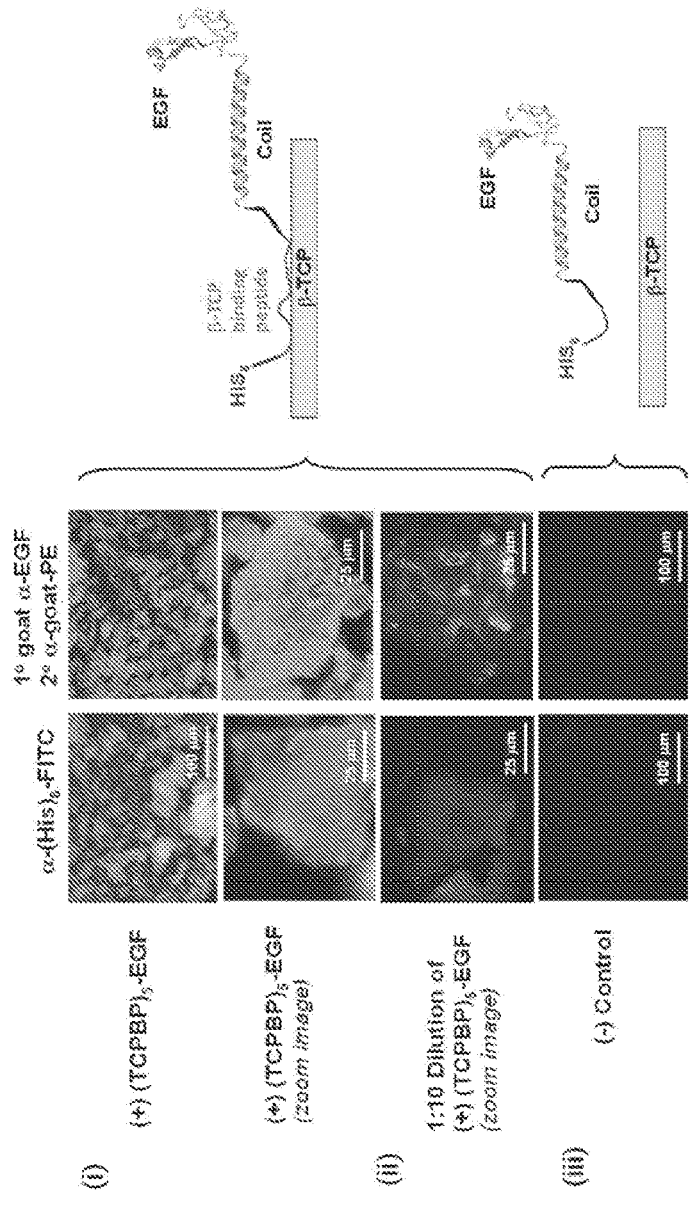
FIG. 4 shows the TCPBP binding characterization. On the left are immunofluorescence micrographs of TCPBP-EGF binding to sieved TCP powder treated with (TCPBP)$_5$-EGF or a control protein lacking the TCPBP region. All images are 3 second exposures. Incubations performed at (i) 10 μM and (ii) 1 μM (TCPBP)$_5$-EGF, and (iii) 10 μM control EGF.

BTCP scaffolds or sieved pure BTCP powder was blocked for 1 hour with salmon serum buffer then incubated at room temperature for two hours in purified TCPBP protein diluted in salmon serum buffer. After incubation, scaffolds or powder were washed three times in three volumes of 20 mM tris buffered saline at pH 7.4 followed by a final wash and storage in PBS. Qualitative assessment of binding was performed by fluorescence microscopy using a FITC-anti-HIS tag antibody and a goat-anti-hEGF (R&D) primary and a TMR-anti-goat secondary as shown in FIG. 4. Control protein incorporating all elements of the TCPBP sequence except the TCPBP region $(LLADTTHHRPWT)_n$ was used as a negative control for non-specific binding in all experiments (FIG. 4, bottom right). Characterizing the binding of each of the concatenated multimers of TCPBP is required in order to determine if increases in multimer insertion increase binding affinity and to determine if the effect reaches a limiting value. Serial dilutions of TCPBP of 3-, 5-, and 10-multimers were incubated with BTCP as described above. Scaffolds were then washed in PBS and bound protein was eluted by incubating the scaffolds in pH 2.2 glycine buffer for one hour and quantifying the amount of TCPBP in the eluate with IRdye immunofluorescence using a western blot format read with a Licor Odyssey IR flatbed scanner. The results of this analysis are shown in FIGS. 5A-5D.

TCPBP binding affinity exhibits a strong dependence on multimer number, as expected. The relative change in affinity is illustrated in FIGS. 5C and 5D. The slope of the response signal as a function of $(TCPBP)_n$ incubation concentration gives a relative indication of the retained protein which reflects the affinity at a given concentration. FIG. 5D shows the strong dependence of repeat number on relative affinity. Based on multimer binding screen shown in FIGS. 5A-5C the 10-mer TCPBP was selected for further experiments.

Quantitative analysis of binding was performed by incubating a serial dilution of (TCPBP)$_{10}$ with 35 mg intact TCP scaffolds treated as described above and analyzed using a quantitative spot blot format read with a Licor Odyssey IR flatbed scanner. The results of this analysis are shown in FIGS. 6A-6C and 7A-7C.

Figures 6A, 6B, 6C:
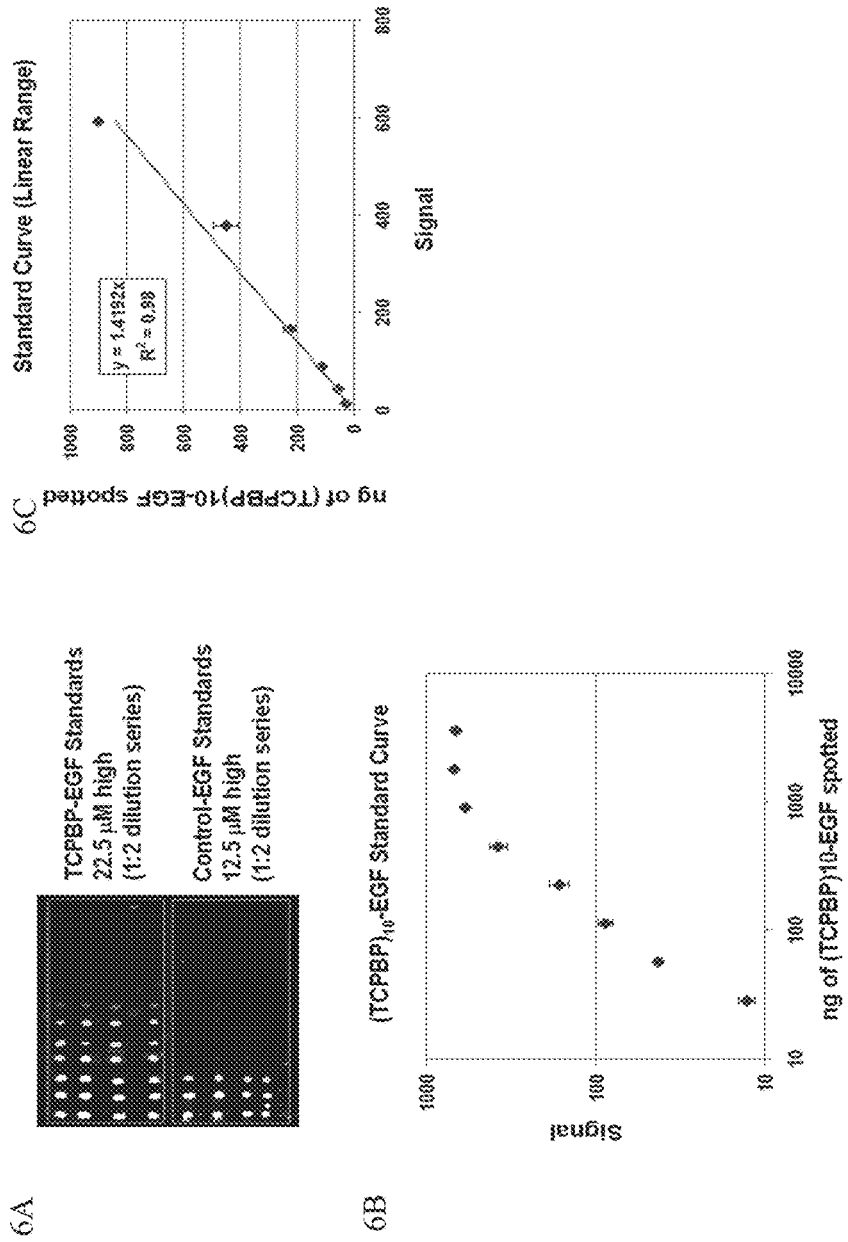
FIGS. 6A-6C show quantification of (TCPBP)10•EGF affinity for BTCP.

Quantifying the amount of bound protein required the creation of a standard curve for both the sample and control protein. FIGS. 6A-6C illustrate the results for the standard curve. To make each curve a known amount of (TCPBP)10 or control (C1 protein as shown in FIG. 4, bottom right) was blotted in quadruplicate onto a nitrocellulose membrane and probed using the methods described above. The resulting signal produced a monotonically increasing signal that began to saturate at the higher end of the curve (FIG. 6B). The first six points of this curve were in the linear range and were used to construct the standard curve. Because the epitope probed in both constructs was identical it was not surprising that both the control and sample protein produced a standard curve with the same slope. The range of protein that can be accurately quantified using this standard was 0 to 900 ng per μL spot.

The analysis of (TCPBP)10 binding to BTCP is shown in FIGS. 7A-7C. The standard curve permitted direct quantification of bound protein and the construction of a binding curve (FIG. 7B). This analysis produced an estimate for the binding constant kD of 3.5 μM. The binding curve also exhibited avidity with a Hill coefficient of 2.3. This was consistent with multimeric protein interactions. Brunauer, Emmet, Teller (BET) analysis of BTCP scaffolds using a 5 point pressure analysis revealed an $N_2$-accessible surface area of 0.8 $m^2/g$. This permitted the estimation of minimum surface number density as shown in (FIG. 7C). The surface area accessible to EGF-(TCPB)10 have been less than the full $N_2$ accessible surface area if the pore size distribution occluded EGF-(TCPB)10 from accessing certain regions of the scaffold. For the purposes of this analysis the discrepancy arising from this effect was assumed to be negligible.

The data in FIGS. 7A-7C, taken together with characteristic EGFR expression levels indicate that the surface density of tethered EGF-(TCPB)10 was more than adequate to stimulate MSCs at a maximal level. For example, at a tethering solution concentration of 1 μM the tethered surface number density was 200 EGF(TCPBP)10 per μm$^2$. A spread cell will have ~500 microns$^2$ of surface area in contact with its substrate which would expose it to ~100,000 EGF molecules. By comparison, the typical MSC expresses 10,000 EGFRs. A significant fraction of these would encounter a tethered EGF over the course of several minutes. In this system the EGFs are constrained at the substrate surface and not as free to diffuse as with soluble EGF and so the kinetics of receptor ligand interaction are not immediately analogous to the soluble case.

With a preliminary characterization of EGF(TCPBP)$_{10}$ surface binding it was possible to analyze cellular effects on a cell type that is clinically relevant. The culture of a low passage (P3) primary human mesenchymal stem cells on BTCP scaffolds treated with EGF(TCPBP)10 was next examined.

Cell Culture

Passage two primary human mesenchymal stem cells (from the Texas A&M Health Science Center College of Medicine's Institute for Regenerative Medicine) were culture expanded to provide sufficient numbers of passage three MSCs prior to all cell culture experiments. Expansion medium consisted of αMEM with 2 mM L-glutamine, 16.5% fetal bovine serum, and penicillin/streptomycin (final concentration 100 units/ml and 100 μg/ml streptomycin). Osteogenic medium consisted of 192 ml expansion medium, 10 nM Dexamethasone (20 μl of a 1:10 dilution of a 1 mM stock in MQ water), 20 mM β-glycerolphosphate (8 ml of 0.5 M stock in expansion medium), and 50 μM L-Ascorbic acid 2-phosphate (200 μl of 50 mM stock solution in MQ water).

Sterile BTCP scaffolds were blocked with salmon serum buffer treated with EGF(TCPBP)10 or left untreated and individually placed into the wells of a 96 well plate. 1,000 to 50,000 cells (as described) were seeded in 200/μL of serum-containing medium (hTMSC) or expansion medium (primary MSC) per well directly onto the scaffolds. Seeded cells were allowed to incubate for 24 hours then were moved into adjacent wells with fresh medium to eliminate the effect of cells which did not seed onto the scaffolds. Seeding efficiency with this method was consistently 40% as determined by counting cells both on the scaffold and in the remnant well (described in the next section).

Proliferation Assays

Cellular proliferation was determined using the AlamarBlue® assay (Biosource Europe, Nivelle Belgium) at various time points post seeding. At each time point AlamarBlue® dye reagent was mixed with either osteogenic or expansion media according to the manufacturer's instructions. Six biological replicates were seeded for each measurement. The tethered BTCP scaffolds were then moved into a ultraviolet (UV) sterilized Falcon™ 96 well plate (Becton Dickinson and Co., NJ USA) attached to a MDV series filter plate adapter (Millipore, Bedford, Mass.). AlamarBlue® dye reagent was then added to each well containing a tethered BTCP scaffold and then incubated at 37° C., 5% $CO_2$ for four hours with gentle mixing by hand every 20 minutes. The filter plate unit was then centrifuged at 1000 RPM for two minutes. This method allowed for complete recovery of dye-media mixture. 100 uL of the resulting dye-media mixture was transferred from the collector plate unit to a new flat-bottom 96-well plate to be read by a SpectraMax® M2e multi-well fluorescent plate reader (Molecular Devices Corp. CA, USA) at a 570 nm excitation wavelength and 585 nm emission wavelength. A standard curve was obtained by performing the same assay on known numbers of cells plated in a 12 well plate and cultured for 1, 4, or 7 days to correspond to the respective time point. Because the AlamarBlue® assay is non-destructive it was possible to directly count the cells with a ViCell™ hemacytometer (Coulter) in order to calibrate the AlamarBlue® signal response to actual cell number.

Figure 8:
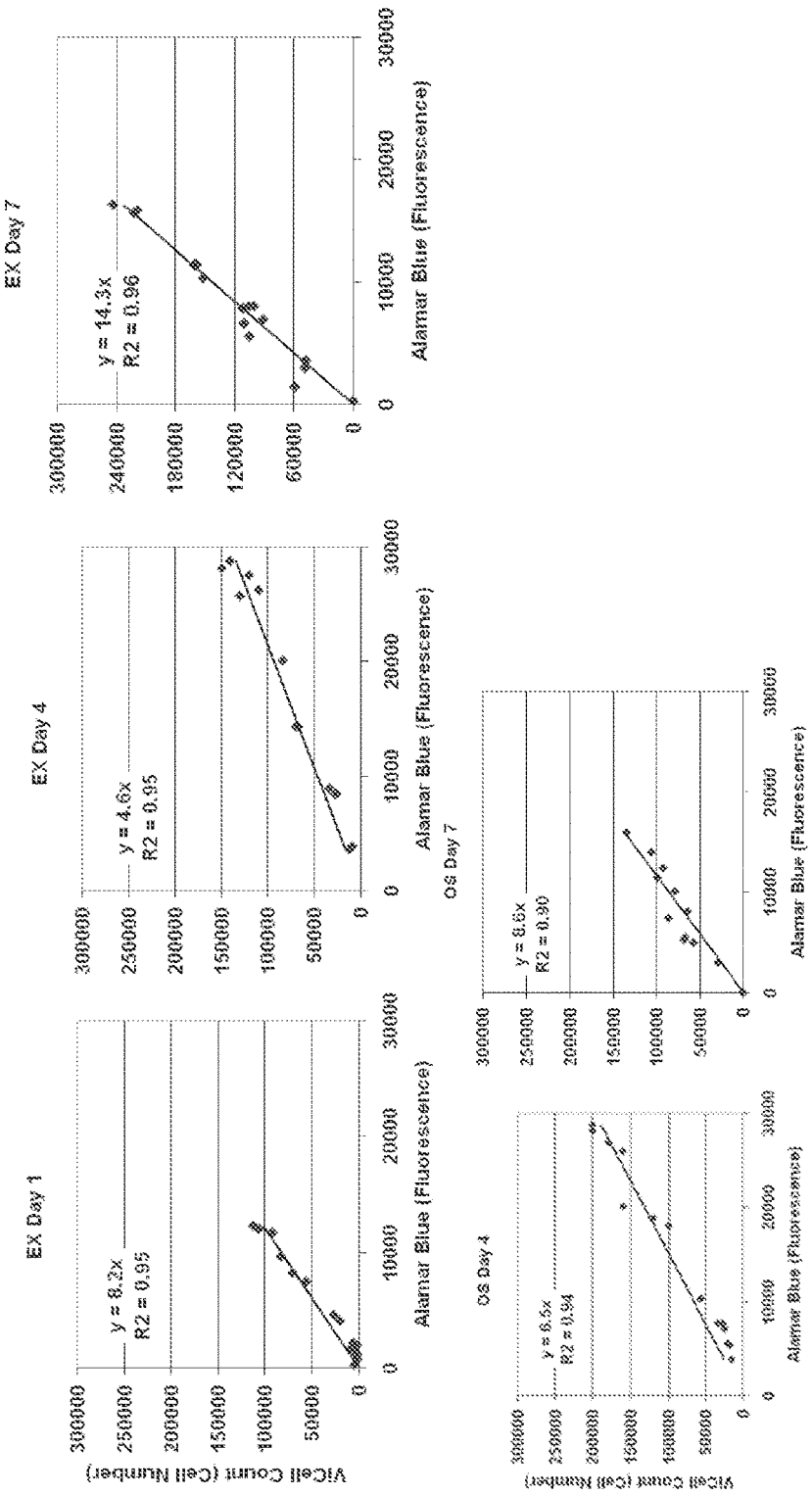
FIG. 8 shows standard curves for the AlamarBlue® based cell proliferation assay. Correlations between cell number and AlamarBlue® fluorescence under each culture condition were used to calibrate results for 3D cultures at each day time point up to 7 days. Cell cultured in osteogenic medium exhibited smaller changes in slope over time.

Hence, a standard curve for each culture condition (expansion medium 'EX' and osteogenic medium 'OS') and each day time point up to 7 days was constructed to assess the magnitude of variation. Metabolic rates under various conditions can vary. As shown in FIG. 8 the slope of each standard curve was an indication of the metabolic activity of the cells in that condition. Variations in the slope of the EX series at different days indicated that cells undergo a shift in metabolism following seeding that can last several days. Under OS medium the slope did not change significantly compared to the day 1 EX (seeding condition). The respective slope for each culture condition and time point was used to convert AlamarBlue® data from the corresponding 3D scaffold conditions into cell number. Day 14 and 21 cultures used the respective day 7 slopes. Standard curves for days 14 and 21 were not reliable due to high confluence and cell death at those time points.

Influence of Cell Seeding Density and Tegf Dose on Msc Proliferation

The survival and proliferation of most mammalian cells exhibit a strong dependence on local cell density. Cells secrete various autocrine factors that enhance survival and proliferation at low cell densities and inhibit proliferation at high cell densities. When the concentration of autocrine factors builds up at high cell densities it was expected that tEGF would enhance cell proliferation, but whether it can protect cells at very low plating density, or overcome inhibition at high densities was unclear. Therefore the proliferation response of MSCs to tEGF was assessed using a range of cell seeding densities and surface tethering densities of tEGF.

By screening the effect of seeding density on proliferation profiles over a typical time course it was possible to select a suitable density to use for future experiments. In addition, it was expected that the surface density of EGF on BTCP affected the proliferation response of cells. EGF has been observed to exert a biphasic effect on cell proliferation in 2D with concentrations near the EC50 (1 nM). In the system described herein, the EGF was tethered on the surface and the equivalent EC50 could only be determined empirically. For the purposes of this experiment cell proliferation was used as a proxy for dose response as shown in FIG. 9.

Cell seeding densities of 1,000; 25,000, and 50,000 cells per 200 ul (volume used to seed each scaffold) were evaluated in expansion medium. The effect of seeding density on proliferation was clearly evident at the 50,000 cell level in FIG. 9 (rightmost plot). A significant drop in cell number is seen at day 4 with recovery by day 7. This effect was much less pronounced at the 25,000 cell seeding level (center plot) and not evident at the 1,000 cell seeding level. Based on these results a seeding density of 30,000 cells per scaffold was selected. This level of seeding was a good compromise between unwanted biphasic effects in proliferation and the amount of time required to obtain sufficient cell material for other analyses (such as RNA for qRTPCR or protein for alkaline phosphatase activity).

By day 7 cell proliferation exhibited a biphasic relationship with respect to surface EGF(TCPBP)10 tethering density at all cell seeding densities, with an apparent maximum at the 1.8 µM tethering concentration. This corresponded to 400 EGF molecules/µm$^2$. Based on these results a concentration of 1 µM EGF(TCPBP)10 for tethering was selected. A detailed examination of the effects of tethered EGF on proliferation and osteogenic differentiation was carried out and is described in the following section.

Effect of tEGF on Primary MSC Proliferation in 3D BTCP Scaffolds

Figure 10:
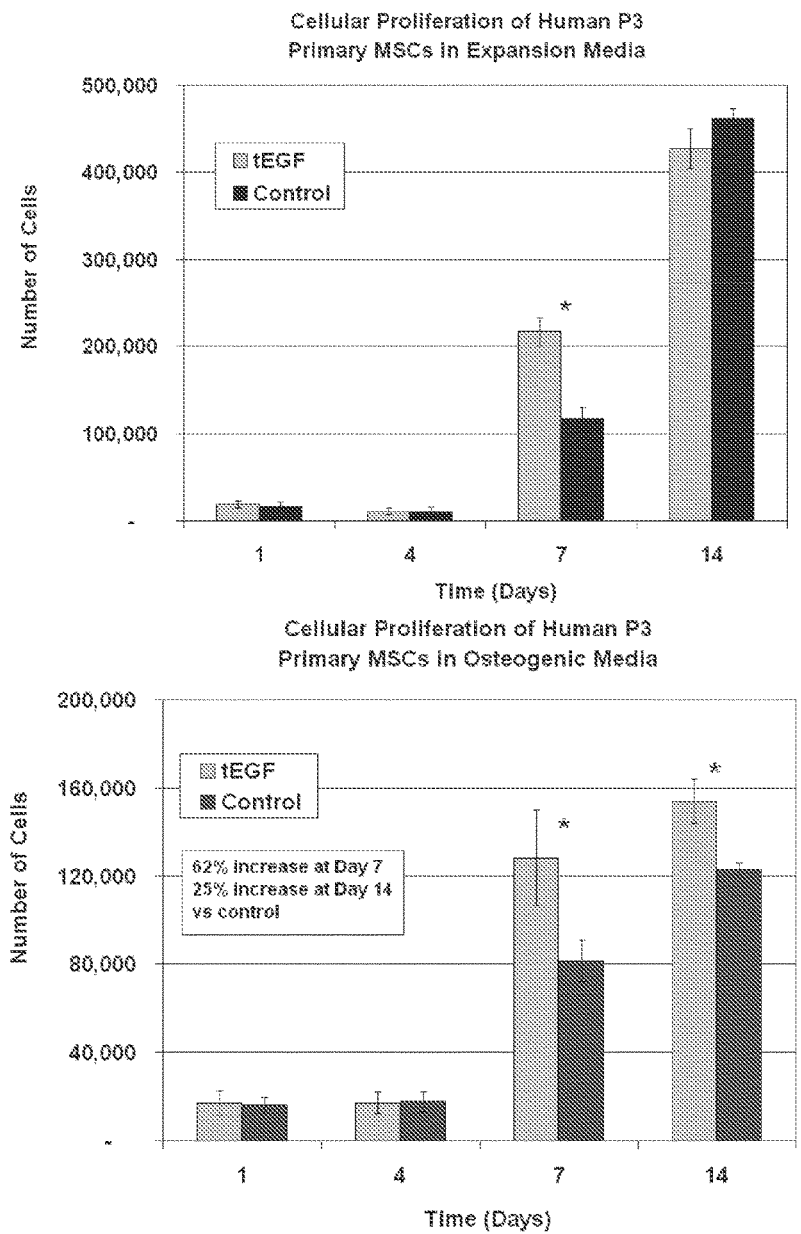
FIG. 10 shows proliferation of MSCs on 3D TCP scaffolds. tEGF promotes MSC proliferation in both EX and OS medium. Under OS conditions increases of 62% and 25% at days 7 and 14, respectively, were observed for MSCs cultured on scaffolds treated with tEGF. n=6, +/−s.d. *p=O.05 vs respective control.
Figure 14A:
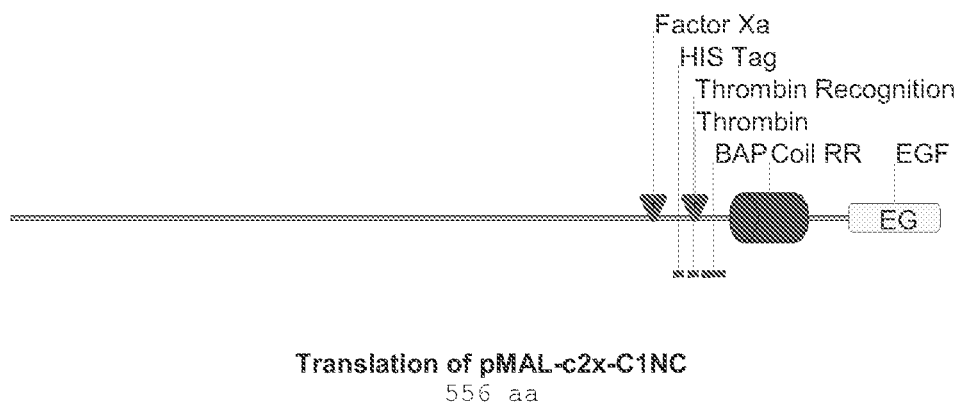

The results of a detailed study of the effect of tEGF on MSC proliferation in both EX and as media are shown in FIG. 10. A cell seeding density of 30,000 per scaffold and tethering concentration of 1 µM EGF(TCPBP)10 were used. In EX medium MSCs exhibited approximately 50% increased proliferation vs the control at day 7. By day 14 this effect was no longer evident, with no significant difference between tEGF and control. The parity at 14 days is likely imposed by the carrying capacity of the scaffold at high cell densities. With over 400,000 cells per scaffold there is likely diffusive transport limitations which impose constraints on EGF stimulated proliferation. In OS medium the effect of tEGF was more pronounced. At day 7 and 14 tEGF resulted in increases of 62% and 25% over controls, respectively. The increase in available MSCs in 3D scaffolds is of particular interest in a clinical setting where scarcity of MSCs limits the scope of procedures where autologous MSCs would be used.

An increase of 20-60% in the number MSCs at a wound site significantly improves outcomes and increases the size of defects which could be treated by taking advantage of sparser seeding densities to achieve the same number as with current methods.

Differentiation Assays

The ability of MSCs to undergo osteogenic differentiation is a useful metric to assess the potency of these cells. Early osteogenic differentiation is typically measured by comparing the alkaline phosphatase activity of induced cells with that of uninduced cells. Later markers include panels of osteogenic transcripts as measured by qRTPCR which give quantitative results. Even later (21 days) mineralization assays, such as Alizarin red staining which stain deposited calcium, can be used. Given the limitation imposed by 3D culture on calcium containing scaffolds, the focus was on alkaline phosphatase assays and qRTPCR to assess osteogenic induction.

Alkaline phosphatase activity was measured using a p-nitrophenol colorimetric assay. Scaffolds were rinsed with PBS twice followed by two freeze-thaw cycles (20 min at −70° C. followed by 10 min at 25° C.). Two scaffolds from the same condition were added to an epindorf tube, and then manually crushed with a pipet tip. Cells were lysed by adding 200 µl of 0.2% NP-40 in 1 mmol/L $MgCl_2$ to each tube. The tubes were incubated with medium shaking for 15 minutes at 4° C. After 5 min of sonication in a water bath samples were centrifuged at 13,000 RPM for 5 minutes. The supernatant was diluted 10-fold and 100-fold with lysis buffer. Diluted sample lysate and lysis buffer were placed in 96-well plates with an all lysis buffer sample used as a background control. A 1:1 solution of 2-Amino-2-methyl-1-propanol, 1.5 mol/L, pH 10.3 at 258C (Sigma, Q17) and stock substrate solution of p-nitrophenyl phosphate disodium (Sigma) was added to the samples and incubated for 30 min at 37° C.; sodium hydroxide was added to stop the reaction. Absorbance at 405 nm was read using SpectraMax® M2e multi-well fluorescent plate reader (Molecular Devices Corp. CA, USA). Background signal from the blank control was subtracted from all readings. A serial dilution of p-nitrophenol in sodium hydroxide was used to generate a standard curve in U/mL: a unit is defined as the amount of enzyme which catalyses the liberation of 1 mmol p-nitrophenol per minute at 37° C. The results are normalized by total protein using the BCA assay (Pierce).

The day 7 alkaline phosphatase activity (ALP) of MSCs grown in EX and OS medium with and without soluble EGF and/or tethered EGF were compared as shown in FIG. 11. OS (positive control) and OS+tEGF produced comparable levels as expected which were the highest among the various conditions. Addition of soluble EGF at 1 ng/mL abrogated the effect of osteogenic medium and resulted in activity which was comparable to EX (negative control). Interestingly the addition of soluble EGF to the Os+tEGF condition reduced overall ALP activity by almost 40%. This result confirmed prior observations that surface tethered EGF provides advantages over sEGF by preserving osteogenic induction potential.

Quantitative Real Time Polymerase Chain Reaction (q-RTPCR)

A set of osteogenic markers suitable for q-RTPCR was selected based on the published literature in the field of osteogenesis and on previous work (Platt, M. O. et al. J Cell Physiol (2009); Ziros, P. G. et al. Journal of Biological Chemistry 277, 23934-23941 (2002); Termine, J. D. et al. Cell 26, 99-105 (1981); Gao, Y. et al., Gene 341, 101-110 (2004); Bradshaw, A. D. et al., Proceedings of the National Academy of Sciences 100, 6045-6050 (2003)). Four markers of particular relevance in osteogenesis are discussed below.

RUNX2 is a transcription factor that is up-regulated in mechanically stressed preosteoblasts and is a reliable indicator of bone forming activity. In osteoblasts there is both a stretch dependent and stretch independent activation of RUNX2 which results in activation of the mitogen activated protein kinase (MAPK) cascade. Interactions between RUNX2 and pERK2 result in potentiation of RUNX2 activity (Ziros, P. G. et al. Journal of Biological Chemistry 277, 23934-23941 (2002)). The stimulation of pERK1/2 via HER1 by tEGF may result in amplification of RUNX2 activity through a stretch-independent mechanism simply by virtue of pERK2 up-regulation. Thus observation of up-regulation in RUNX2 activity in MSCs cultured on tEGF treated scaffolds would have at least one mechanistic explanation given the common ERK signaling node.

Osteocalcin (bone gamma-carboxyglutamic acid protein) is a small protein associated with mineralized bone matrix. Hoang found that osteocalcin contains a negatively charged surface that coordinates five calcium ions in an orientation that complements calcium ions in the hydroxyapatite crystal lattice of natural bone (Hoang, Q. Q. et al., Nature 425, 977-980 (2003)). Osteocalcin is downstream of RUNX2 and has been shown to become up-regulated following up-regulation of RUNX2 (Mikami, Y. et al., Biochemical and Biophysical Research Communications 362, 368-373 (2007)).

Osterix (SP7) is a zinc finger transcription factor and a regulator of bone cell differentiation that is reported to operate downstream of RUNX2 (Gao, Y. et al., Gene 341, 101-110 (2004); Matsubara, T. et al. Journal of Biological Chemistry 283, 29119 (2008)). Evidence of this may be seen in FIG. 12 (bottom plots). Here the re-expression of osterix at day 14 following early RUNX2 upregulation under the tEGF condition at day 4 is likely a manifestation of this effect.

Osteonectin is a matrix protein that inhibits cell cycle progression and elicits changes in cell morphology. It also exerts influence over the synthesis of extracellular matrix in an osteogenic setting (Bradshaw, A. D. et al., Proceedings of the National Academy of Sciences 100, 6045-6050 (2003)) and binds to hydroxyapatite and collagen fibers at distal sites accounting for the ability of bone collagen to undergo calcification (Termine, J. D. et al. Cell 26, 99-105 (1981)).

3D BTCP scaffolds were treated with 1 µM EGF (TCPBP)$_{10}$ as described above and seeded at 30,000 cells per scaffold. At the indicated time points RNA was harvested from nine biological replicates per condition using a Qiagen RNEasy Plus II kit (scaffolds were pooled into three biological replicates). The resulting RNA was quantified, normalized to equal concentration then subjected to a two step q-RTPCR reaction using a Qiagen Sybrgreen Quick kit and run on a Chromoph04 thermal cycler with an optical sensor top. Each biological replicate was split into three technical replicates. Melting curves were analyzed at the end of each run to confirm the absence of contamination products. Primers for each gene were obtained from the Qiagen Quantitect primer bank.

As shown in FIG. 12 all four gene products showed statistically significant upregulation at day 14 in the tEGF condition. Early up-regulation of RUNX2 of 5-fold may have served as an early up-regulator of downstream factors such as osteocalcin and osterix. A six-fold upregulation of osteonectin at day 14 is indicative of increased matrix deposition as would be expected at later time points. The biphasic expression of osteocalcin, osterix, and RUNX2 with a minimum at day 7 may be indicative of changes in cell cycle progression toward proliferation as seen in the proliferation data (FIG. 10). The effect of tEGF on the expression of key osteogenic factors during 3D cell culture is a promising result, particularly when taking into consideration effects on proliferation. Taken together these results give a strong indication that tEGF significantly increases proliferation of MSCs without compromising early osteogenic differentiation.

Long Term Survival Assay Using htMSCs

The impact of tEGF on the survival on MSCs has already been described here and in the literature. Confirming these results in 3D tissue culture would permit extension of these results into clinically relevant settings. The following section describes a long term hTMSC survival assay designed to evaluate the effect of tEGF.

Human telomerase reverse transcriptase immortalized human mesenchymal stem cells (htMSCs or htertMSCs) were routinely cultured in Dulbecco's Modified Eagle Medium supplemented with 10% fetal bovine serum for the htertMSCs and 16.5% for the primary human MSCs, 2 mM L-glutamate, Na-pyruvate, non-essential amino acid supplement, and penicillin/streptomycin (final concentration 100 units/ml and 100 µg/ml streptomycin). In certain experiments where indicated, serum was omitted from this medium. Both nuclear staining and histological analysis of the tEGF treated scaffolds showed marked differences in the amount of cellular invasion into the 3D BTCP scaffold and of the relative survival effect at 23 days.

The striking differences observed in FIGS. 13A-13B likely added relevance in surgical settings where extensive wound sizes can present very harsh conditions for cell survival. The rescue of already sparse MSCs in a harsh wound environment is of great clinical benefit.

Conclusions

This work described herein demonstrates that MSCs cultured on BTCP scaffolds tethered with EGF proliferate at a greater rate than those cultured on untreated scaffolds and that this increase in proliferation does not compromise the early differentiation potential of MSCs. Significantly, it has been shown that soluble EGF does not confer the same advantage thus implicating a modulation of EGF bioactivity when presented as a matrix bound ligand. It is also clear that tethered EGF confers a strong survival advantage to htMSC when cultured under extreme conditions such as serum starvation.

The ability to stably tether bioactive components to the surface of BTCP scaffolds using the methods described herein permits a wide range of basic studies in tissue regeneration and may lead to clinically useful approaches. One particular area is that of spatially guided tissue regeneration such as the vascularization of regenerated bone and the regeneration of osteochondral interfaces.

Example 2

Characterization and Modification of BTCP Binding Peptides

Figure 28:
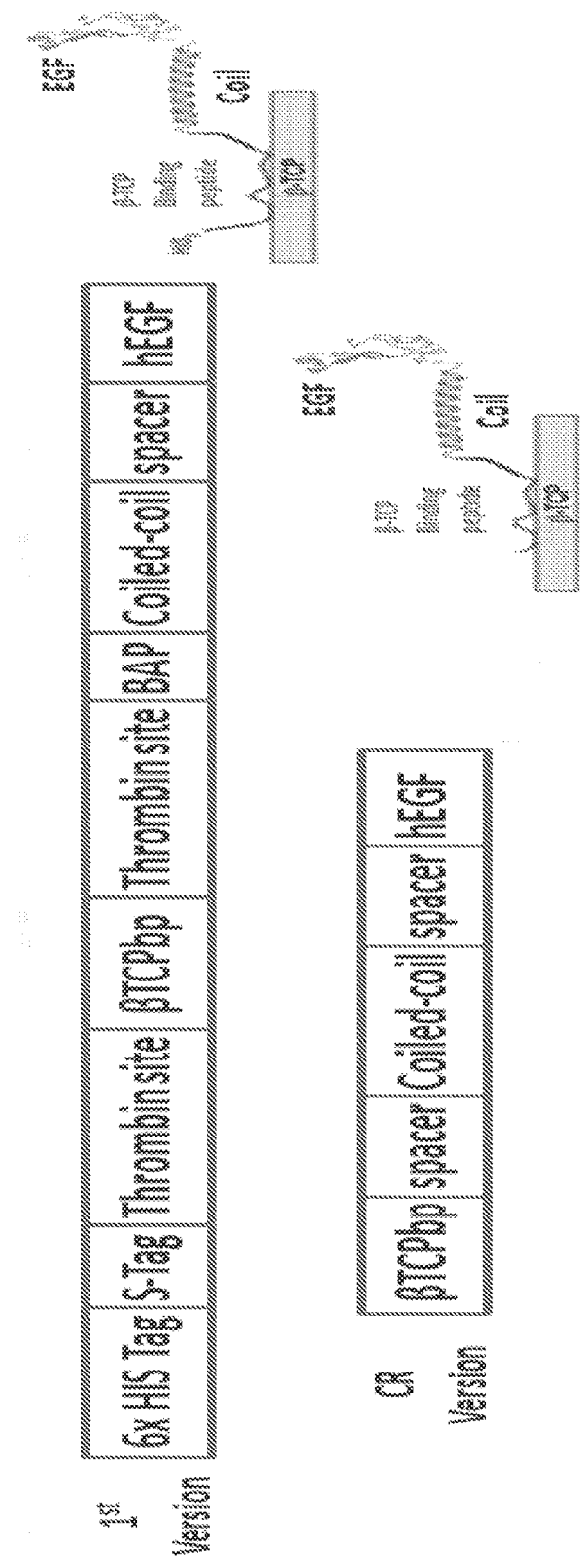
FIG. 28 is a graphic showing the design of clinically-relevant (CR) versions of the BTCPbp-EGF fusions.

To address clinical translation, where EGF is bound to scaffolds containing BTCP, protein engineering approaches including phage display were used to create a fusion protein of EGF with a peptide that exhibits high affinity binding to BTCP; these two moieties were separated by a protease-resistant spacer to enhance accessibility of the EGF (See FIGS. 28 and 29). Successive iterations of the specific protein sequence employed in efforts to improve the yield and properties of the protein were examined; modifications included the nature of the purification moiety and the composition of the spacer. Also, several purification strategies were investigated. A sequence and purification strategy was defined wherein one key facet of the strategy was including a step to remove endotoxin to produce a final product with endotoxin levels of 38.9 EU/mg, which is 10-fold below commercial standards set at <1000 EU/mg (the Table). This product, BTCP binding peptide in fusion with EGF ((BTCPbP)$_{10}$-C1-EGF), was made and purified reproducibly to provide a low-endotoxin product.

Figure 15:
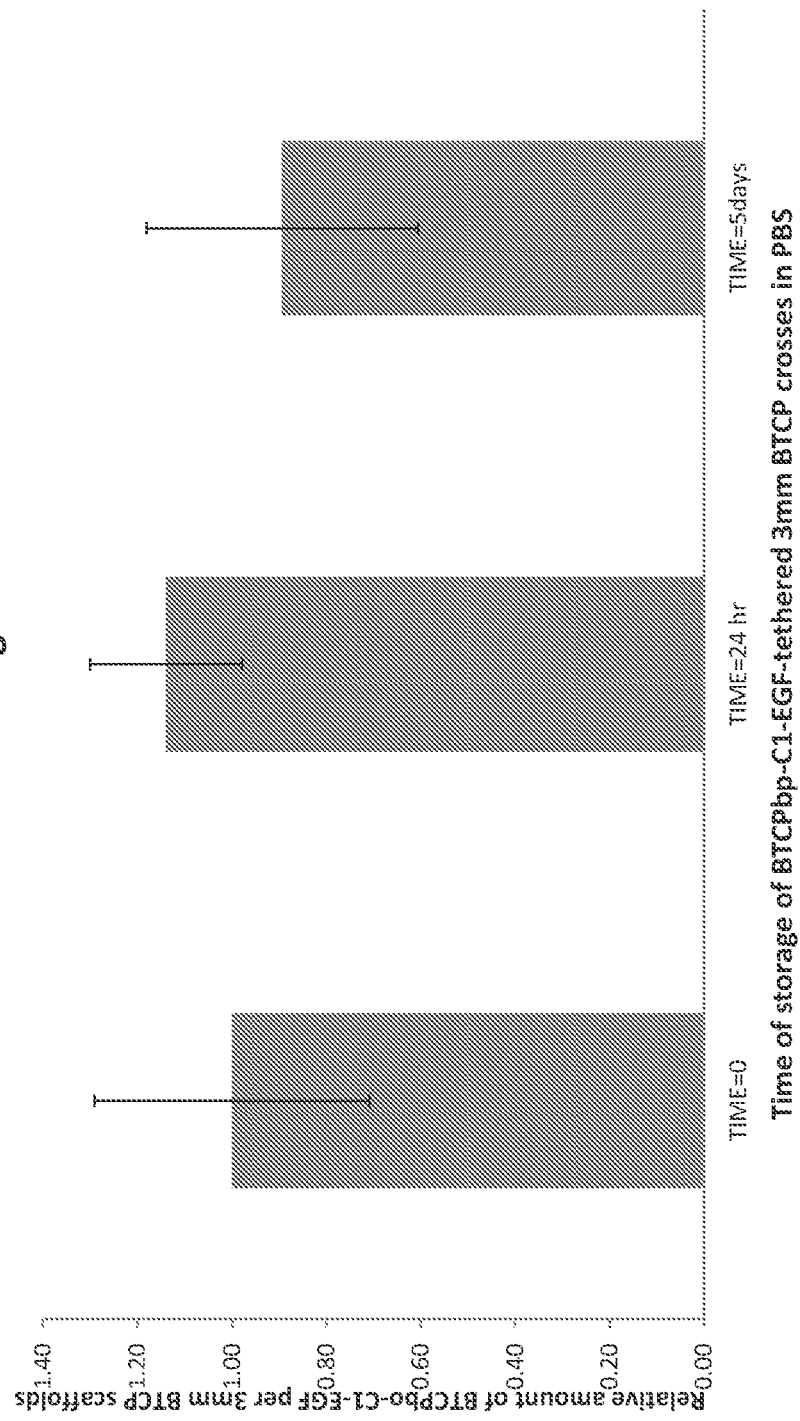
FIG. 15 shows quantification of BTCPbp-C1-EGF tethered (tethering concentration=2.7 uM) to 3-mm BTCP scaffolds after timed storage in PBS. (See method section for details of the dot blot quantification.) There was no statistically significant difference in the amount of BTCPbp-C1-EGF remaining on the scaffold after different storage times in PBS (p-value>0.05, N=4) indicating that there was no significant release of tethered BTCPbp-C1-EGF after 5 days of storage in PBS. At time=0 the average amount of mass tethered per 3-mm BTCP scaffold was 922 nanograms of BTCPbp-C1-EGF.
Figure 16:
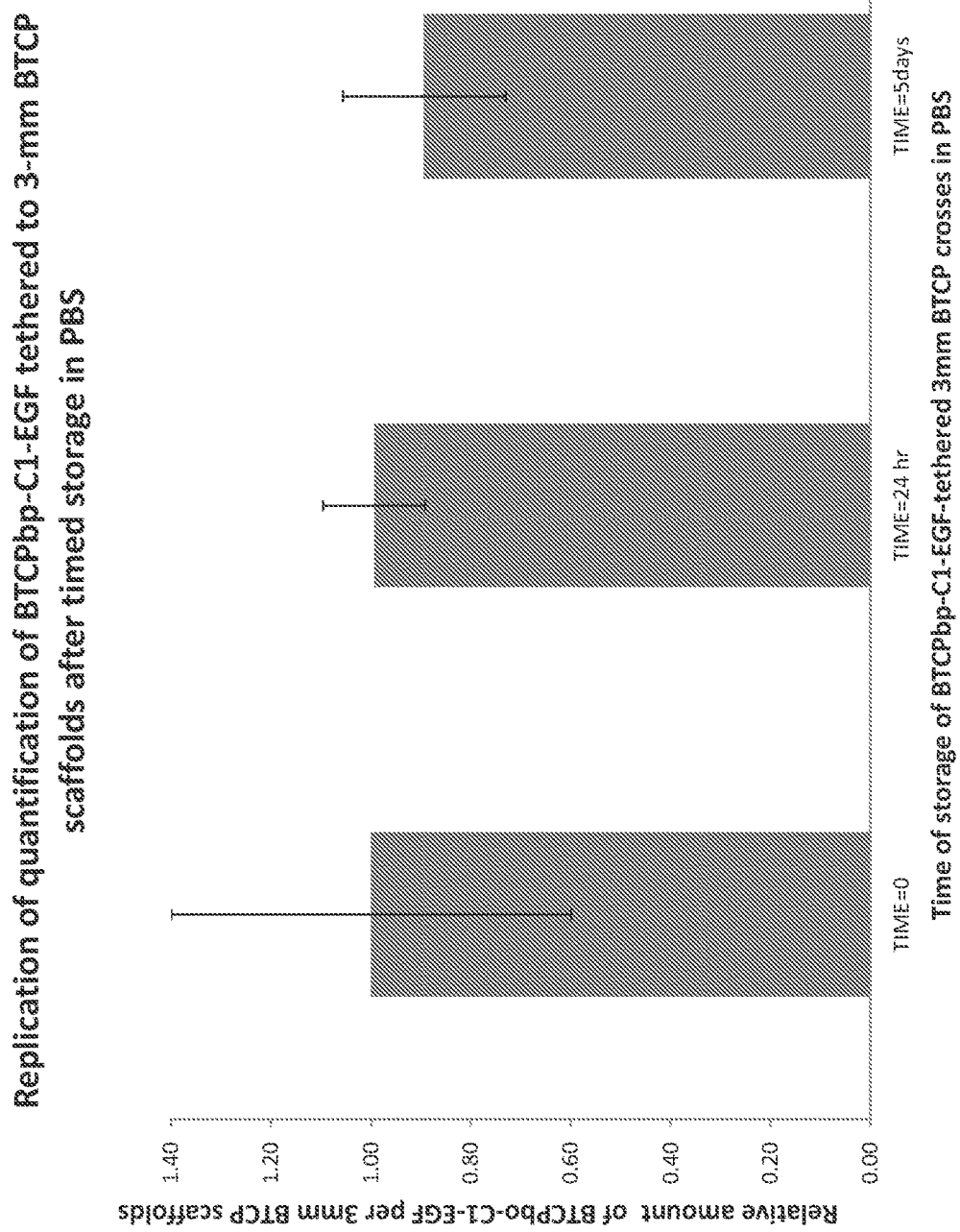
FIG. 16 shows quantification of BTCPbp-C1-EGF tethered (tethering concentration=3.8 uM) to 3-mm BTCP scaffolds after timed storage in PBS. (See method section for details of the dot blot quantification.) There was no statistically significant difference in the amount of BTCPbp-C1-EGF remaining on the scaffold after different storage times in PBS (p-value>0.05) indicating that there was no significant release of tethered BTCPbp-C1-EGF after 5 days of storage in PBS. At time=0 the average amount of mass tethered per 3-mm BTCP scaffold was 852 nanograms of BTCPbp-C1-EGF.
Figure 22:
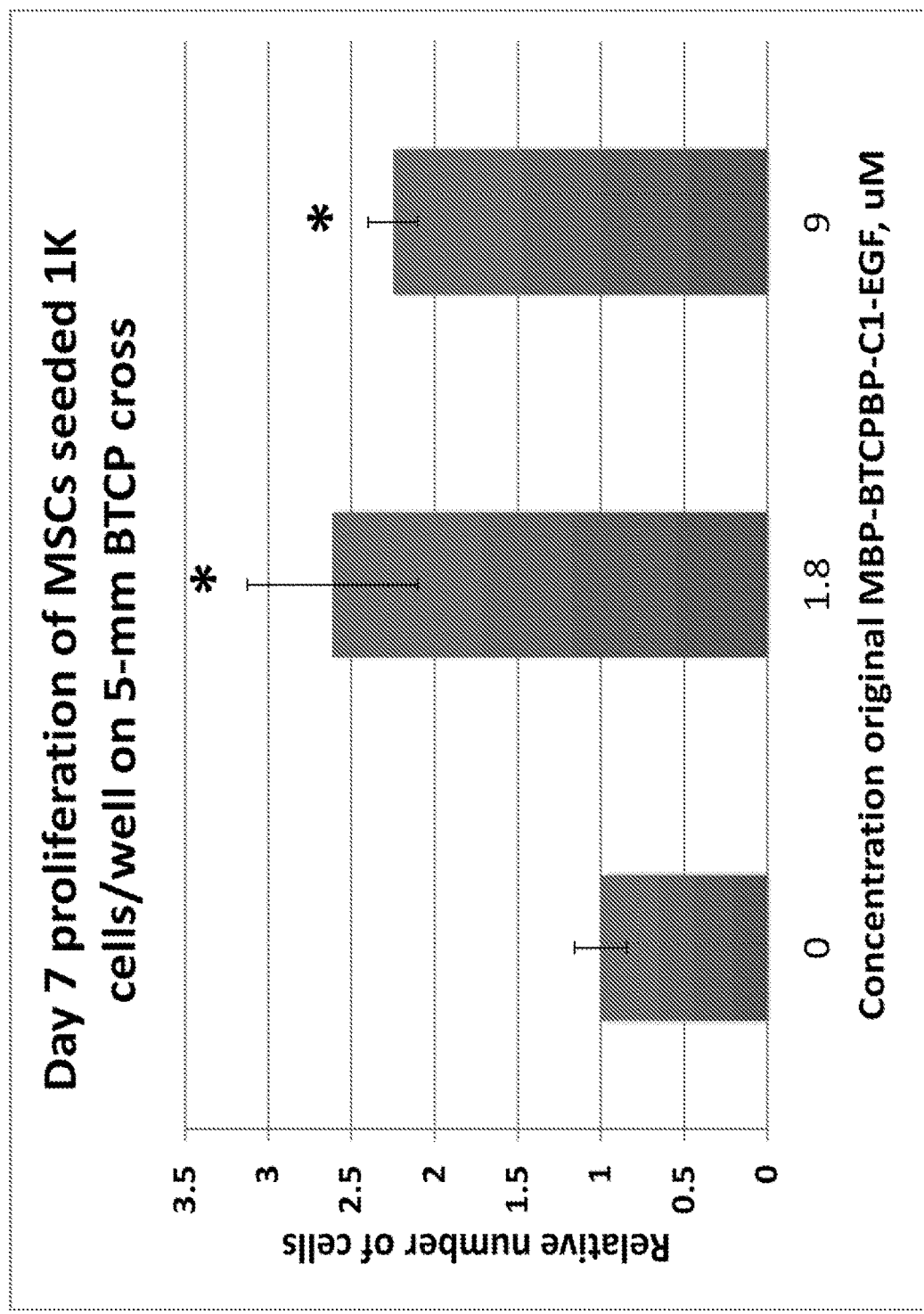
FIG. 22 shows MSC proliferation is enhanced between 1.8 and 9 uM inferring that tethering above 9 uM does not further enhance proliferation. MSCs were seeded on BTCP scaffolds tethered with BTCPbp-C1-EGF at various concentrations. All scaffolds were incubated in EX medium and proliferation was measured at terminal endpoints using the using the Alamar Blue based cell proliferation assay. *p=0.05 vs 0 uM, n=6, +/−s.d.
Figure 23:
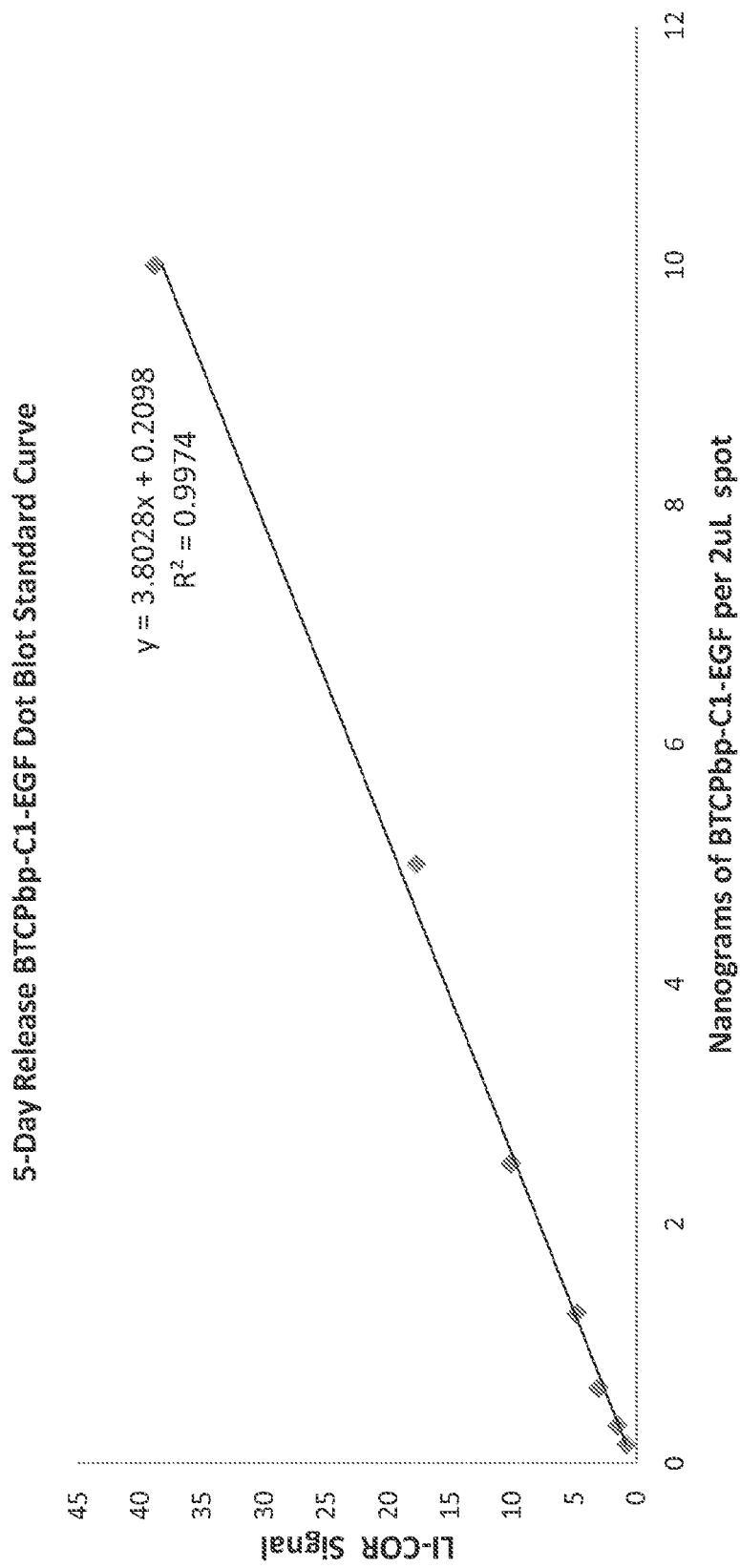
FIG. 23 is a graph of a 5-day release of BTCPbp-C1-EGF Dot Blot standard curve.
Figure 24:
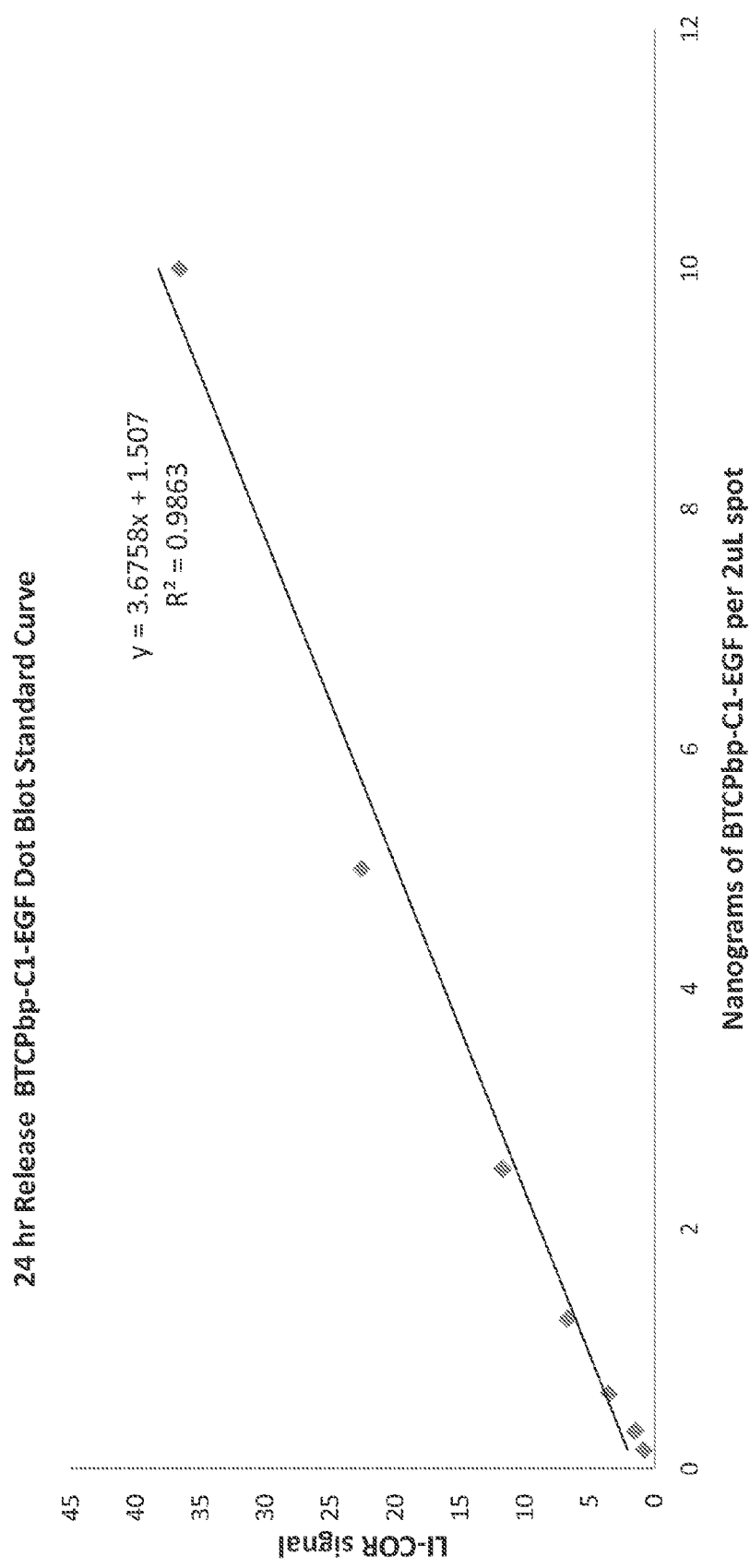
FIG. 24 is a graph of a 24 hour release BTCPbp-C1-EGF Dot Blot standard curve.

Also addressed were concerns about the stability of the association of the BTCP-C1-EGF fusion protein with BTCP bone scaffolds. The stability of this association for BTCP-C1-EGF bound to a commercial BTCP bone void filler scaffold (Integra Life Sciences), using protein adsorbed at saturation concentrations and following the release of protein into a PBS supernate over 5 days, was measured. Saturation concentrations (2-4 uM) were determined (FIGS. 22, 23, 24). The experiment was conducted with n>3 scaffolds per time point. Further, to provide evidence for reproducibility, the experiment using protein from the same batch was repeated. The replicate experiments yielded statistically indistinguishable results, and showed that >90% of the purified EGF fusion protein is retained on the scaffolds over the 5-day period (FIGS. 15 and 16, Tables 2 and 3). These data were consistent with the biological effects of this protein in over ten different experiments (4, 6, 10), where increased MSC growth or colony formation during culture periods of 5+ days was found. Table 3 summarizes the data on protein release after 5 days. These data show that approximately 1-2% of the tethered protein is released over the course of 5 days. As a point of reference, each 3 mm TCP scaffolds binds, on-average, about 0.9-1 microgram of protein at these tethering concentrations, whereas over the course of 5 days less than 15 nanograms (0.015 micrograms) of protein is released into solution. This indicates exceptionally tight binding. This fusion protein has significant biological effects relevant for regeneration of tissues in vivo by transplantation of bone marrow-derived stromal cells when it is in a purified form relevant for in vivo implantation.

Figure 30:
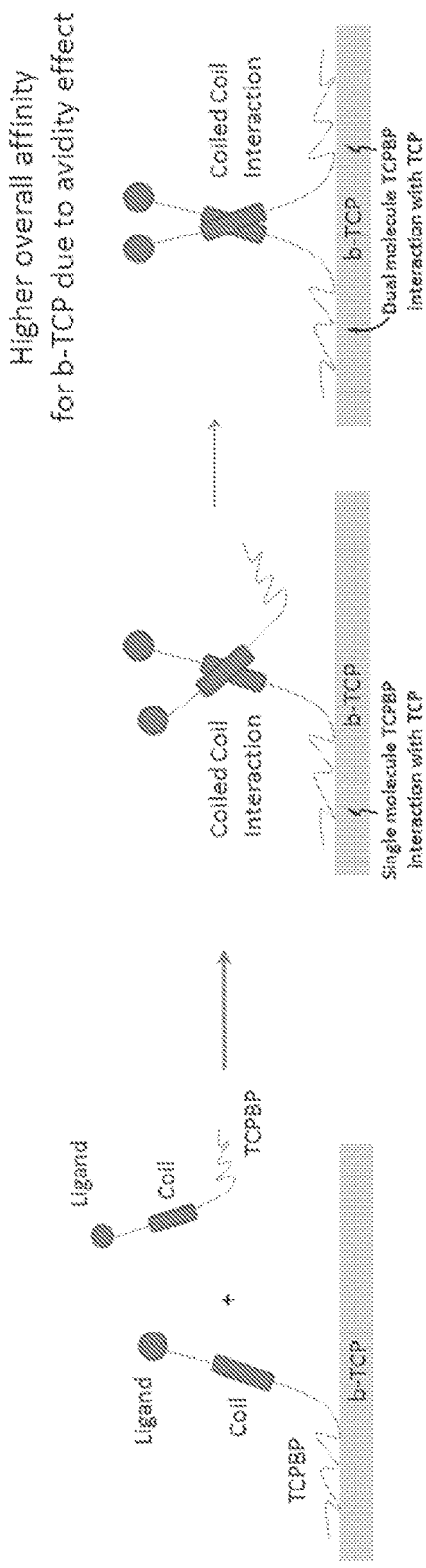
FIG. 30 is a graphic illustrating increased residence time of TCBPbp due to interaction through coiled coil linkers of the BTCPbps.

In addition to the binding between the TCP binding peptide and the b-TCP substrate material there is another interaction that is important to increase overall affinity of the described proteins for their TCP substrates. This is accomplished through an avidity interaction. The coil regions (either C1 or C2 coils) are homodimerizing. The C1-C1 homodimerization affinity is 2.5 E-7 molar and C2-C2 homodimerization affinity is 4.4E-5 molar. This homodimerization can complement the binding of TCP binding peptide containing proteins for TCP by binding a neighboring protein via the coiled coil interaction. This interaction increases the residence time (and local effective concentration) of the neighboring protein's TCP binding peptide relative to the TCP surface, thus resulting in an avidity interaction. This is depicted in FIG. 30.

Figure 25:
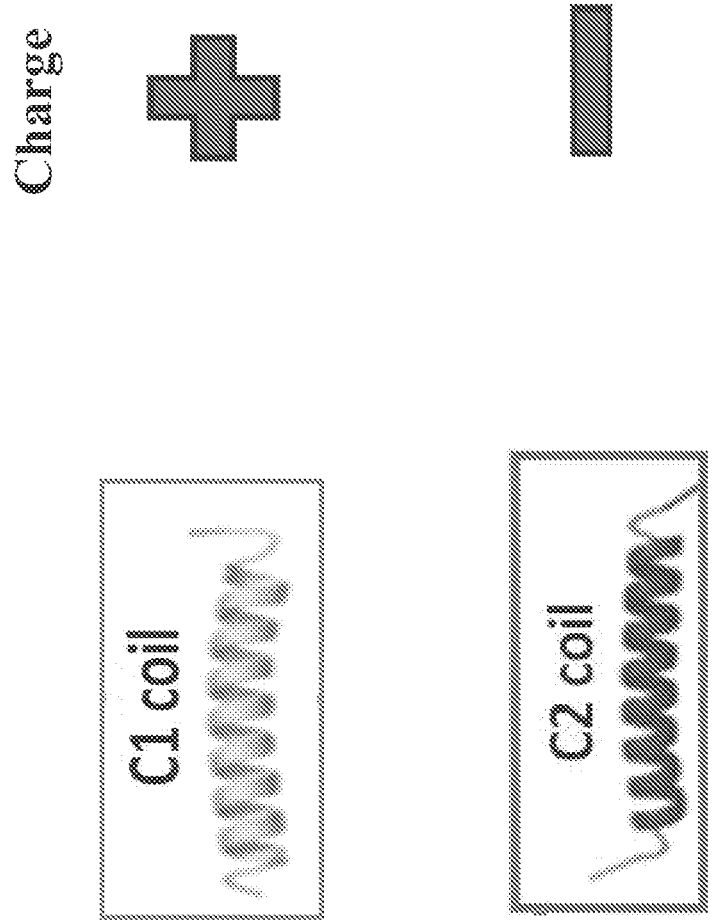
FIG. 25 is an illustration of the C1 coil and the C2 coil and their respective charges.
Figure 26:
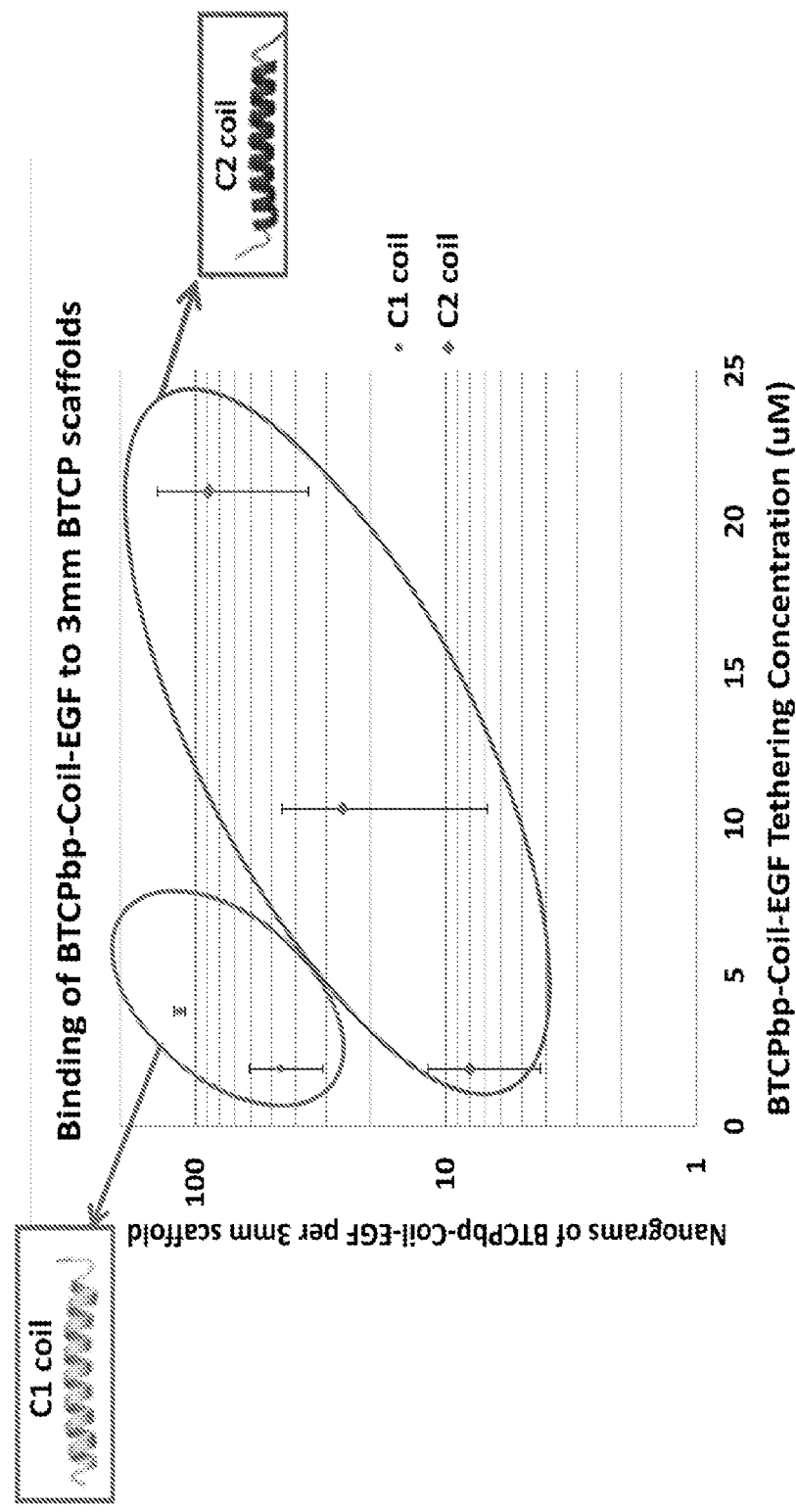
FIG. 26 is a graph showing the BTCPbp-C1coil-EGF binds better than BTCPbp-C2coil-EGF to 3 mm BTCP scaffolds.

FIGS. 25-27 describe the differences in binding resulting from use of each kind of coil (C1 or C2). As shown the protein construct with the C1 coil exhibits higher binding affinity for b-TCP due to the avidity effect.

Methods
Production of BTCPbp-C1-EGF Protein and Endotoxin Removal

Figure 18:
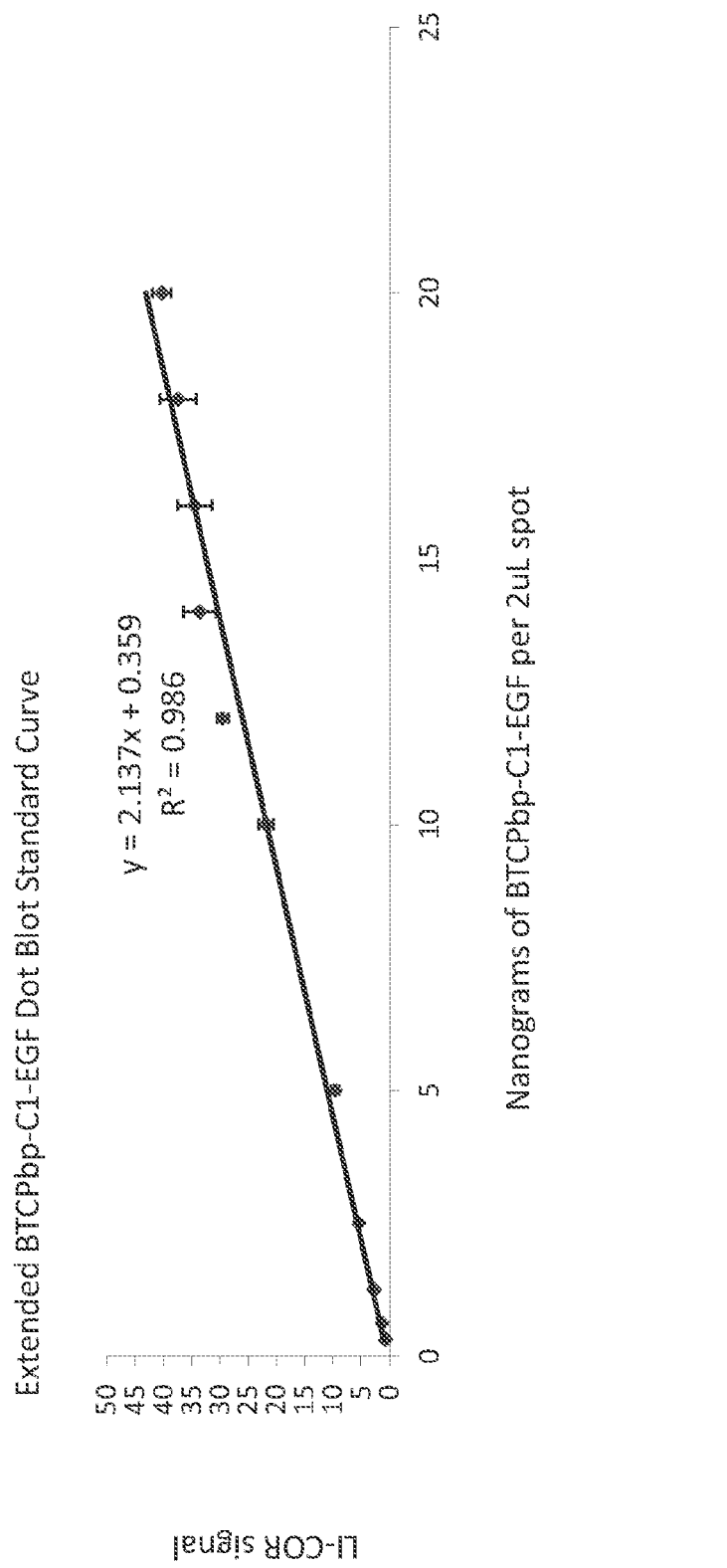
FIG. 18 shows extended standard curve for the BTCPbp-C1-EGF Dot Blot. Specific amounts of BTCPbp-C1-EGF were spotted on a nitrocellulose membrane ranging from 0.312 ng to 20 ng and a standard curve was constructed for analysis of BTCPbp-C1-EGF tethered onto 3-mm BTCP scaffolds.
Figure 20:
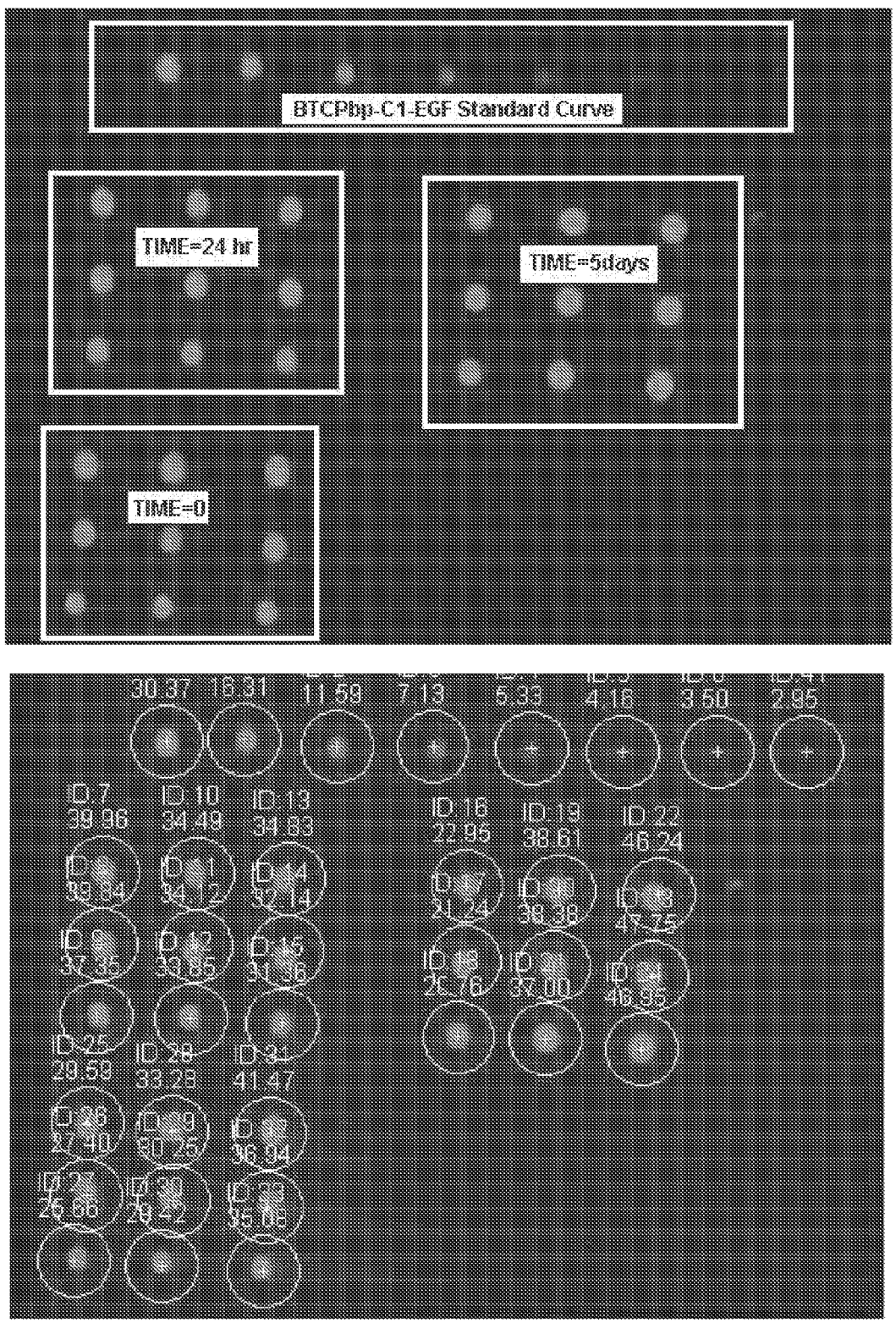
FIG. 20 shows Dot Blots for the replicate experiment to quantify tethered BTCPbp-C1-EGF at different time points. The top image shows the dot blot without the infrared LI-COR intensity values for each spot and the bottom image is the same as the top image but with the infrared LI-COR intensity values shown for each spot. The background intensity is taken from a region without any spots and the intensity value for this blot was 2.95.

A BTCP-binding peptide was discovered through phage display and the BTCP-binding peptide in fusion with EGF was produced in E. coli and purified. For planned in vivo studies, additional purification to remove endotoxin was employed. An on-column (amylose column) method for endotoxin removal was designed based on a previously published protocol (Cheng, H T, et al., Protein Expr Purif, 61(1):65-72 (2008)). Briefly, the method involved extensive washes of the amylose resin-bound BTCPbp-C1-EGF with column buffer containing detergent Triton X-114 and then washing with column buffer to remove excess Triton X-114. Endotoxin levels in the final product were determined by LAL assay by the Media Preparation Lab in Central Cell Services in Research Core Services of the Lerner Research Institute at the Cleveland Clinic. This facility has a stringent QC program and is responsible for measuring endotoxin and mycoplasm in all media, solutions, broths, buffers and samples provided by Lerner Research Institute investigators.
BTCPbp-C1-EGF Adsorption To and Release from BTCP Scaffolds A stock solution of purified, endotoxin-free BTCPbp-C1-EGF was diluted in PBS to saturation concentrations of 2-4 uM (see data for exact values in each experiment). BTCP scaffolds in the form of 3-mm crosses were obtained from Integra Life Sciences and were placed in a well of a 96-well plate and incubated with BTCPbp-C1-EGF solution for 36 hours at 4° C. while shaking at 150 rpm. After tethering, the scaffolds were rinsed twice with PBS and placed in fresh PBS solution, and stored at 4° C. for 0, 24 hours or 5 days. To measure stability, four replicate crosses for each of the three time points (0, 1 day, 5 days) were removed from the PBS at the stated time and was rinsed twice with PBS. The amount of EGF associated with each cross was assessed by releasing bound protein using a denaturing 0.2 M glycine buffer, pH=2.2, following a standard protocol (NEB, Ph.D.™-12 Phage Display Peptide Library; www.neb.com/nebecomm/manualfiles/manuale8101.pdf) that was first employed for stripping bound phage from BTCP. This protocol completely stripped protein from the surface of the BTCP. The 3-mm BTCP crosses received from Integra vary in mass by 16% (11.9±1.9 mg per cross, N=10). The variation in cross mass and the loss of mass due to partial disintegration in solution contributed to ~20% error in the final determination of tethered BTCPbp-C1-EGF. This error was independent of the quantification assay and was due to changes in the surface area of the BTCP cross available for tethering due to mass loss.
Quantification of Tethered BTCPbp-C1-EGF Released from BTCP Scaffolds by Dot Blot Assay Rather than infer amounts of active protein from a relatively insensitive and non-specific total protein assay such as BCA (sensitivity=5 ng total protein/uL), a highly sensitive Dot Blot immunoassay protocol (sensitivity=0.078 ng of EGF/uL) was employed to measure EGF directly, as the major question was how much EGF remains associated with the scaffolds. Briefly, the tethered BTCPbp-C1-EGF, which was released from the BTCP scaffolds by the glycine buffer, was spotted along with BTCPbp-C1-EGF standards on a nitrocellulose membrane (2 uL/spot). BTCPbp-C1-EGF standards ranging from 0.156 ng to 10 ng per spot were spotted on the same blot. A separate blot was made for BTCPbp-C1-EGF standards ranging from 0.156 ng to 20 ng per spot because some scaffolds had more than 10 ng of tethered BTCPbp-C1-EGF per spot. The standard curves were linear to 20 ng of BTCPbp-C1-EGF per spot. The dot blots were analyzed with a LI-COR Odyssey Infrared Imaging System using a primary antibody against hEGF and an IR dye tagged secondary antibody (LI-COR Biosciences, www.licor.com/bio/PDF/IRquant.pdf) (9,10). The standard curves were used to quantify the amount of tethered BTCPbp-C1-EGF removed from the 3-mm BTCP scaffolds by the glycine buffer. The amount of tethered BTCPbp-C1-EGF removed by the glycine buffer after storage in PBS for 0 hours, 24 hours or 5 days is shown in FIGS. 15 and 16. The standard curves are shown in FIGS. 17 and 18. The dot blots with and without the infrared LI-COR intensity are shown in FIGS. 19, 20, and 21. Statistical significant difference between time points was assessed by the t-test.

TABLE 1

Endotoxin levels in BTCPbp-C1-EGF were reduced more than 100-fold over untreated BTCPbp-C1-EGF and are now more than 10-fold below commercial standards. The endotoxin results were obtained by LAL assay. See Methods for details.

| Protein | EU/mg of protein |
| --- | --- |
| BTCPbp-C1-EGF with endotoxin removal | 38.9 |
| BTCPbp-C1-EGF w/o endotoxin removal | 6344.6 |
| Commercial human EGF (Peprotech) | Guaranteed as less than 1000 |
| Commercial human EGF (R&D Systems) | Guaranteed as less than 1000 |

** This table shows that before endotoxin removal out protein had 6344.6 Endotoxin units per mg (EU/mg). After endotoxin removal, there were 38.9 EU/mg. This is more han 100-fold lower than without endotoxin removal.

TABLE 2

| BTCPbp-C1-EGF Tethering concentration used | Cross # | L1-Cor signal for 2 uL spot | Nanograms of BTCPbp-C1-EGF released per 3 mm BTCP scaffold | Average nanograms of BTCPbp-C1-EGF released per 3 mm BTCP scaffold |
| --- | --- | --- | --- | --- |
| 3.8 uM | 1 | 0.41* | <9.8 | <12.0 |
|  | 2 | 1.21 | 16.4 |  |
|  | 3 | 0.77* | <9.8 |  |
| 2.7 uM | 1 | 0.29* | <9.8 | <13.1 |
|  | 2 | 0.48* | <9.8 |  |
|  | 3 | 0.28* | <9.8 |  |
|  | 4 | 1.62 | 23.18 |  |

*Signal below sensitivity of 0.156 ng per 2 uL spot. (Sensitivity = 9.8 ng released per 3 mm BTCP scaffold).
The total volume of PBS solution per well was 125 uL.

TABLE 3

| BTCPbp-C1-EGF Tethering concentration used | Cross # | LI-Cor signal for 2 uL spot | Nanograms of BTCPbp-C1-EGF released per 3 mm BTCP scaffold | Average nanograms of BTCPbp-C1-EGF released per 3 mm BTCP scaffold |
| --- | --- | --- | --- | --- |
| 3.8 uM | 1 | 0.83* | <12.8 | <12.8 |
|  | 2 | 0.72* | <12.8 |  |
|  | 3 | 0.61* | <12.8 |  |
| 2.7 uM | 1 | 0.34* | <12.8 | <12.8 |
|  | 2 | 0.34* | <12.8 |  |
|  | 3 | 0.52* | <12.8 |  |
|  | 4 | 0.70* | <12.8 |  |

*Signal below sensitivity of 0.205 ng per 2 uL spot. (Sensitivity = 12.8 ng released per 3 mm BTCP scaffold).
The total volume of PBS solution per well was 125 uL.

SUMMARY

At saturation tethering concentrations (2-4 uM) on average 900 ng of BTCPbp-C1-EGF per 3-mm BTCP scaffold can be tethered. This demonstrated that the tethering strategy is reproducible even on a 3D scaffold surface.

There is no significant release of tethered BTCPbp-C1-EGF after 5 days of storage in PBS, independent of tethering concentration. This data demonstrated desirable release characteristics and was evidence for the high affinity interaction between the BTCPbp-C1-EGF and the BTCP scaffold surface.

BTCPbp-C1-EGF adsorption to and release from BTCP scaffolds was linear between 0.156 ng to 20 ng per 2 uL spot.

Endotoxin removal from BTCPbp-C1-EGF was successful and is now 10-fold below commercial standards of protein production. FDA limits on endotoxin for in vivo studies are listed as 0.5 EU/cm3 and are not based on a specific ratio of EU/mg of protein. In order to be within FDA limits for in vivo experiments we just have to limit the mass of BTCPbp-C1-EGF put in each site can be adjusted without exceeding 0.5 EU/cm3.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A composition comprising a beta-tricalcium phosphate (β-TCP) non-covalently bound to a concatenated multimer of two or more β-TCP binding peptides, wherein at least one of the β-TCP binding peptides comprises LLADTTHHRPWT (SEQ ID NO: 1), and binds to β-TCP with a Kd of 3.5 µM or lower.

2. The composition of claim 1 wherein the β-TCP is a β-TCP scaffold.

3. The composition of claim 2 wherein the scaffold further comprises polylactide-co-glycolide.

4. The composition of claim 2 wherein the scaffold further comprises one or more porogens.

5. The composition of claim 4 wherein the porogen is sucrose.

6. The composition of claim 1 wherein the composition is a concatenated multimer comprising two, three, four, five, six, seven, eight, nine, ten, eleven, twelve, thirteen, fourteen, fifteen, sixteen, seventeen, eighteen, nineteen, or twenty repeats of a β-TCP binding peptide bound to the β-TCP.

7. The composition of claim 1 wherein at least one of the β-TCP binding peptides comprises the amino acid sequence: GQVLPTTTPSSP (SEQ ID NO: 2), VPQHPYPVPSHK (SEQ ID NO: 3), HNMAPATLHPLP (SEQ ID NO: 4), QSFASLTNPRVL (SEQ ID NO: 5), HTTPTTTYAAPP (SEQ ID NO: 6), QYGVVSHLTHTP (SEQ ID NO: 7), TMSNPITSLISV (SEQ ID NO: 8), IGRISTHAPLHP (SEQ ID NO: 9), MNDPSPWLRSPR (SEQ ID NO: 10), QSLGSMFQEGHR (SEQ ID NO: 11), KPLFTRYGDVAI (SEQ ID NO: 12), MPFGARILSLPN (SEQ ID NO: 13), QLQLSNSMSSLS (SEQ ID NO: 14), TMNMPAKIFAAM (SEQ ID NO: 15), EPTKEYTTSYHR (SEQ ID NO: 16), DLNELYLRSLRA (SEQ ID NO: 17), DYDSTHGAVFRL (SEQ ID NO: 18), SKHERYPQSPEM (SEQ ID NO: 19), HTHSSDGSLLGN (SEQ ID NO: 20), NYDSMSEPRSHG (SEQ ID NO: 21), ANPIISVQTAMD (SEQ ID NO: 22) or a combination thereof.

8. The composition of claim 1 wherein one or more of the β-TCP binding peptides is fused to one or more additional peptides or proteins.

9. The composition of claim 8 wherein each β-TCP binding peptide is fused to each additional peptide or protein via a linker.

10. The composition of claim 8 wherein one or more of the β-TCP binding peptides is fused to all or a portion of a growth factor or a cytokine.

11. The composition of claim 8 wherein the one or more additional peptides or proteins is an epidermal growth factor (EGF), a platelet-derived growth factor (PDGF), a bone morphogenic protein 2 (BMP-2), BMP-4, BMP-7, osteogenic protein (OP-1), collagen binding protein or a combination thereof.

12. The composition of claim 9 wherein the linker is a coiled coil linker.

13. The composition of claim 12 wherein the coiled coil linker is a leucine zipper.

14. The composition of claim 1 wherein the composition further comprises mesenchymal stem cells.

15. A pharmaceutical composition comprising the composition of claim 1.

16. The composition of claim 2, wherein the (β-TCP scaffold is in the shape of a cross having at least one dimension that is 3 mm in size.

17. The composition of claim 16, wherein the cross has the dimensions 5 mm×5 mm×3 mm.

18. The composition of claim 2, wherein the (β-TCP scaffold comprises granulated β-TCP powder that is at least 95% β-TCP.

19. The composition of claim 1, wherein each β-TCP binding peptide comprises LLADTTHHRPWT (SEQ ID NO: 1), and binds to (β-TCP with a Kd of 3.5 µM or lower.

* * * * *

UNITED STATES PATENT AND TRADEMARK OFFICE
CERTIFICATE OF CORRECTION

PATENT NO. : 10,329,327 B2
APPLICATION NO. : 13/991842
DATED : June 25, 2019
INVENTOR(S) : Alvarez et al.

Page 1 of 1

It is certified that error appears in the above-identified patent and that said Letters Patent is hereby corrected as shown below:

In the Specification

In the Government Support paragraph, Column 1, Line 19:
"No. W81XH-08-2-0034" should be --No. W81XWH-08-2-0034--.

Signed and Sealed this
Seventeenth Day of September, 2019

Andrei Iancu
*Director of the United States Patent and Trademark Office*

UNITED STATES PATENT AND TRADEMARK OFFICE
CERTIFICATE OF CORRECTION

PATENT NO. : 10,329,327 B2  
APPLICATION NO. : 13/991842  
DATED : June 25, 2019  
INVENTOR(S) : Luis Alvarez et al.

Page 1 of 1

It is certified that error appears in the above-identified patent and that said Letters Patent is hereby corrected as shown below:

In the Specification

In the Government Support paragraph, Column 1, Line 17: "Grant No. R10 EB003805" should be --Grant No. R01 EB003805--.

Signed and Sealed this  
Twenty-eighth Day of July, 2020

Andrei Iancu  
*Director of the United States Patent and Trademark Office*

SEQUENCE LISTING

<160> NUMBER OF SEQ ID NOS: 34

<210> SEQ ID NO 1
<211> LENGTH: 12
<212> TYPE: PRT
<213> ORGANISM: unknown
<220> FEATURE:
<223> OTHER INFORMATION: Beta-TCP binding peptide

<400> SEQUENCE: 1

Leu Leu Ala Asp Thr Thr His His Arg Pro Trp Thr
1               5                   10

<210> SEQ ID NO 2
<211> LENGTH: 12

```
<212> TYPE: PRT
<213> ORGANISM: unknown
<220> FEATURE:
<223> OTHER INFORMATION: Beta-TCP binding peptide

<400> SEQUENCE: 2

Gly Gln Val Leu Pro Thr Thr Thr Pro Ser Ser Pro
1               5                   10

<210> SEQ ID NO 3
<211> LENGTH: 12
<212> TYPE: PRT
<213> ORGANISM: unknown
<220> FEATURE:
<223> OTHER INFORMATION: Beta-TCP binding peptide

<400> SEQUENCE: 3

Val Pro Gln His Pro Tyr Pro Val Pro Ser His Lys
1               5                   10

<210> SEQ ID NO 4
<211> LENGTH: 12
<212> TYPE: PRT
<213> ORGANISM: unknown
<220> FEATURE:
<223> OTHER INFORMATION: Beta-TCP binding peptide

<400> SEQUENCE: 4

His Asn Met Ala Pro Ala Thr Leu His Pro Leu Pro
1               5                   10

<210> SEQ ID NO 5
<211> LENGTH: 12
<212> TYPE: PRT
<213> ORGANISM: unknown
<220> FEATURE:
<223> OTHER INFORMATION: Beta-TCP binding peptide

<400> SEQUENCE: 5

Gln Ser Phe Ala Ser Leu Thr Asn Pro Arg Val Leu
1               5                   10

<210> SEQ ID NO 6
<211> LENGTH: 12
<212> TYPE: PRT
<213> ORGANISM: unknown
<220> FEATURE:
<223> OTHER INFORMATION: Beta-TCP binding peptide

<400> SEQUENCE: 6

His Thr Thr Pro Thr Thr Thr Tyr Ala Ala Pro Pro
1               5                   10

<210> SEQ ID NO 7
<211> LENGTH: 12
<212> TYPE: PRT
<213> ORGANISM: unknown
<220> FEATURE:
<223> OTHER INFORMATION: Beta-TCP binding peptide

<400> SEQUENCE: 7

Gln Tyr Gly Val Val Ser His Leu Thr His Thr Pro
1               5                   10

<210> SEQ ID NO 8
<211> LENGTH: 12
<212> TYPE: PRT
```

```
<213> ORGANISM: unknown
<220> FEATURE:
<223> OTHER INFORMATION: Beta-TCP binding peptide

<400> SEQUENCE: 8

Thr Met Ser Asn Pro Ile Thr Ser Leu Ile Ser Val
1               5                   10

<210> SEQ ID NO 9
<211> LENGTH: 12
<212> TYPE: PRT
<213> ORGANISM: unknown
<220> FEATURE:
<223> OTHER INFORMATION: Beta-TCP binding peptide

<400> SEQUENCE: 9

Ile Gly Arg Ile Ser Thr His Ala Pro Leu His Pro
1               5                   10

<210> SEQ ID NO 10
<211> LENGTH: 12
<212> TYPE: PRT
<213> ORGANISM: unknown
<220> FEATURE:
<223> OTHER INFORMATION: Beta-TCP binding peptide

<400> SEQUENCE: 10

Met Asn Asp Pro Ser Pro Trp Leu Arg Ser Pro Arg
1               5                   10

<210> SEQ ID NO 11
<211> LENGTH: 12
<212> TYPE: PRT
<213> ORGANISM: unknown
<220> FEATURE:
<223> OTHER INFORMATION: Beta-TCP binding peptide

<400> SEQUENCE: 11

Gln Ser Leu Gly Ser Met Phe Gln Glu Gly His Arg
1               5                   10

<210> SEQ ID NO 12
<211> LENGTH: 12
<212> TYPE: PRT
<213> ORGANISM: unknown
<220> FEATURE:
<223> OTHER INFORMATION: Beta-TCP binding peptide

<400> SEQUENCE: 12

Lys Pro Leu Phe Thr Arg Tyr Gly Asp Val Ala Ile
1               5                   10

<210> SEQ ID NO 13
<211> LENGTH: 12
<212> TYPE: PRT
<213> ORGANISM: unknown
<220> FEATURE:
<223> OTHER INFORMATION: Beta-TCP binding peptide

<400> SEQUENCE: 13

Met Pro Phe Gly Ala Arg Ile Leu Ser Leu Pro Asn
1               5                   10

<210> SEQ ID NO 14
<211> LENGTH: 12
<212> TYPE: PRT
<213> ORGANISM: unknown
```

<220> FEATURE:
<223> OTHER INFORMATION: Beta-TCP binding peptide

<400> SEQUENCE: 14

Gln Leu Gln Leu Ser Asn Ser Met Ser Ser Leu Ser
1               5                   10

<210> SEQ ID NO 15
<211> LENGTH: 12
<212> TYPE: PRT
<213> ORGANISM: unknown
<220> FEATURE:
<223> OTHER INFORMATION: Beta-TCP binding peptide

<400> SEQUENCE: 15

Thr Met Asn Met Pro Ala Lys Ile Phe Ala Ala Met
1               5                   10

<210> SEQ ID NO 16
<211> LENGTH: 12
<212> TYPE: PRT
<213> ORGANISM: unknown
<220> FEATURE:
<223> OTHER INFORMATION: Beta-TCP binding peptide

<400> SEQUENCE: 16

Glu Pro Thr Lys Glu Tyr Thr Thr Ser Tyr His Arg
1               5                   10

<210> SEQ ID NO 17
<211> LENGTH: 12
<212> TYPE: PRT
<213> ORGANISM: unknown
<220> FEATURE:
<223> OTHER INFORMATION: Beta-TCP binding peptide

<400> SEQUENCE: 17

Asp Leu Asn Glu Leu Tyr Leu Arg Ser Leu Arg Ala
1               5                   10

<210> SEQ ID NO 18
<211> LENGTH: 12
<212> TYPE: PRT
<213> ORGANISM: unknown
<220> FEATURE:
<223> OTHER INFORMATION: Beta-TCP binding peptide

<400> SEQUENCE: 18

Asp Tyr Asp Ser Thr His Gly Ala Val Phe Arg Leu
1               5                   10

<210> SEQ ID NO 19
<211> LENGTH: 12
<212> TYPE: PRT
<213> ORGANISM: unknown
<220> FEATURE:
<223> OTHER INFORMATION: Beta-TCP binding peptide

<400> SEQUENCE: 19

Ser Lys His Glu Arg Tyr Pro Gln Ser Pro Glu Met
1               5                   10

<210> SEQ ID NO 20
<211> LENGTH: 12
<212> TYPE: PRT
<213> ORGANISM: unknown
<220> FEATURE:

<223> OTHER INFORMATION: Beta-TCP binding peptide

<400> SEQUENCE: 20

His Thr His Ser Ser Asp Gly Ser Leu Leu Gly Asn
1               5                   10

<210> SEQ ID NO 21
<211> LENGTH: 12
<212> TYPE: PRT
<213> ORGANISM: unknown
<220> FEATURE:
<223> OTHER INFORMATION: Beta-TCP binding peptide

<400> SEQUENCE: 21

Asn Tyr Asp Ser Met Ser Glu Pro Arg Ser His Gly
1               5                   10

<210> SEQ ID NO 22
<211> LENGTH: 12
<212> TYPE: PRT
<213> ORGANISM: unknown
<220> FEATURE:
<223> OTHER INFORMATION: Beta-TCP binding peptide

<400> SEQUENCE: 22

Ala Asn Pro Ile Ile Ser Val Gln Thr Ala Met Asp
1               5                   10

<210> SEQ ID NO 23
<211> LENGTH: 13
<212> TYPE: PRT
<213> ORGANISM: unknown
<220> FEATURE:
<223> OTHER INFORMATION: Beta-TCP binding peptideconsensus sequence

<400> SEQUENCE: 23

Thr Leu Leu Ala Asp Thr Thr His His Arg Pro Trp Thr
1               5                   10

<210> SEQ ID NO 24
<211> LENGTH: 556
<212> TYPE: PRT
<213> ORGANISM: unknown
<220> FEATURE:
<223> OTHER INFORMATION: pMal-c2x-C1NC construct

<400> SEQUENCE: 24

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

```
Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                    165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                    245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Gly Ser Ser His His His His
385                 390                 395                 400

His His Ser Ser Gly Leu Val Pro Arg Gly Ser His Met Gly Leu Asn
                    405                 410                 415

Asp Ile Phe Glu Ala Gln Lys Ile Glu Trp His Trp Thr Ser Lys Gly
                420                 425                 430

Gly Gly Leu Glu Ile Arg Ala Ala Phe Leu Arg Arg Asn Thr Ala
            435                 440                 445

Leu Arg Thr Arg Val Ala Glu Leu Arg Gln Arg Val Gln Arg Leu Arg
450                 455                 460

Asn Ile Val Ser Gln Tyr Glu Thr Arg Tyr Gly Pro Leu Thr Gly Ala
465                 470                 475                 480

Ser Gly Ala Gly Gly Ser Glu Gly Gly Ser Glu Gly Gly Thr Ser
                    485                 490                 495

Gly Ala Thr Gly Ala Asn Ser Asp Ser Glu Cys Pro Leu Ser His Asp
                500                 505                 510

Gly Tyr Cys Leu His Asp Gly Val Cys Met Tyr Ile Glu Ala Leu Asp
            515                 520                 525

Lys Tyr Ala Cys Asn Cys Val Val Gly Tyr Ile Gly Glu Arg Cys Gln
530                 535                 540
```

Tyr Arg Asp Leu Lys Trp Trp Glu Leu Arg Leu Glu
545                 550                 555

<210> SEQ ID NO 25
<211> LENGTH: 540
<212> TYPE: PRT
<213> ORGANISM: unknown
<220> FEATURE:
<223> OTHER INFORMATION: pMal-c2x-c2NC construct

<400> SEQUENCE: 25

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
    355                 360                 365

Ser Ser Ser Asn Asn Asn Asn Asn Asn Asn Asn Leu Gly Ile
370                 375                 380

Glu Gly Arg Ile Ser Glu Phe Gly Ser Asn Ser Asp Ser Glu Cys Pro
385                 390                 395                 400

Leu Ser His Asp Gly Tyr Cys Leu His Asp Gly Val Cys Met Tyr Ile
            405                 410                 415

Glu Ala Leu Asp Lys Tyr Ala Cys Asn Cys Val Val Gly Tyr Ile Gly
            420                 425                 430

Glu Arg Cys Gln Tyr Arg Asp Leu Lys Trp Trp Glu Leu Arg Ile Asn
            435                 440                 445

Ala Ser Gly Ala Gly Gly Ser Glu Gly Gly Gly Ser Glu Gly Gly Thr
450                 455                 460

Ser Gly Ala Thr Thr Gly Leu Glu Ile Glu Ala Ala Phe Leu Glu Gln
465                 470                 475                 480

Glu Asn Thr Ala Leu Glu Thr Glu Val Ala Glu Leu Glu Gln Glu Val
            485                 490                 495

Gln Arg Leu Glu Asn Ile Val Ser Gln Tyr Glu Thr Arg Tyr Gly Pro
            500                 505                 510

Leu Gly Gly Gly Lys Leu Glu Glu Gln Lys Leu Ile Ser Glu Glu Asp
            515                 520                 525

Leu Lys Leu Gly Thr Gly Arg Arg Phe Thr Thr Ser
530                 535                 540

<210> SEQ ID NO 26
<211> LENGTH: 247
<212> TYPE: PRT
<213> ORGANISM: unknown
<220> FEATURE:
<223> OTHER INFORMATION: pMal-c2x-EE single construct

<400> SEQUENCE: 26

Arg Ile Ser Glu Phe Asn Ser Asp Ser Glu Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Asn Cys Val Val Gly Tyr Ile Gly Glu Arg Cys Gln
        35                  40                  45

Tyr Arg Asp Leu Lys Trp Trp Glu Leu Arg Ile Asn Ala Ser Gly Ala
50                  55                  60

Gly Gly Ser Glu Gly Gly Gly Ser Glu Gly Gly Thr Ser Gly Ala Thr
65                  70                  75                  80

Thr Gly Ser Gly Ser Ser His His His His His Ser Ser Gly
            85                  90                  95

Leu Val Pro Arg Gly Ser His Met Gly Leu Asn Asp Ile Phe Glu Ala
            100                 105                 110

Gln Lys Ile Glu Trp His Trp Thr Ser Lys Gly Gly Leu Glu Ile
        115                 120                 125

Arg Ala Ala Phe Leu Arg Arg Arg Asn Thr Ala Leu Arg Thr Arg Val
130                 135                 140

Ala Glu Leu Arg Gln Arg Val Gln Arg Leu Arg Asn Ile Val Ser Gln
145                 150                 155                 160

Tyr Glu Thr Arg Tyr Gly Pro Leu Thr Gly Ala Ser Gly Ala Gly Gly
            165                 170                 175

```
Ser Glu Gly Gly Gly Ser Glu Gly Gly Thr Ser Gly Ala Thr Gly Ala
            180                 185                 190

Asn Ser Asp Ser Glu Cys Pro Leu Ser His Asp Gly Tyr Cys Leu His
        195                 200                 205

Asp Gly Val Cys Met Tyr Ile Glu Ala Leu Asp Lys Tyr Ala Cys Asn
    210                 215                 220

Cys Val Val Gly Tyr Ile Gly Glu Arg Cys Gln Tyr Arg Asp Leu Lys
225                 230                 235                 240

Trp Trp Glu Leu Arg Leu Glu
                245
```

<210> SEQ ID NO 27
<211> LENGTH: 266
<212> TYPE: PRT
<213> ORGANISM: unknown
<220> FEATURE:
<223> OTHER INFORMATION: pMal-EN EGF-NRG single construct

<400> SEQUENCE: 27

```
Arg Ile Ser Glu Phe Gly Thr Ser His Leu Val Lys Cys Ala Glu Lys
1               5                   10                  15

Glu Lys Thr Phe Cys Val Asn Gly Gly Glu Cys Phe Met Val Lys Asp
            20                  25                  30

Leu Ser Asn Pro Ser Arg Tyr Leu Cys Lys Cys Pro Asn Glu Phe Thr
        35                  40                  45

Gly Asp Arg Cys Gln Asn Tyr Val Met Ala Ser Phe Tyr Lys His Leu
    50                  55                  60

Gly Ile Glu Phe Met Glu Ala Glu Leu Tyr Gln Lys Ile Asn Ala
65                  70                  75                  80

Ser Gly Ala Gly Gly Ser Glu Gly Gly Ser Glu Gly Gly Thr Ser
            85                  90                  95

Gly Ala Thr Thr Gly Gly Ser Gly Ser Ser His His His His His His
            100                 105                 110

Ser Ser Gly Leu Val Pro Arg Gly Ser His Met Gly Leu Asn Asp Ile
        115                 120                 125

Phe Glu Ala Gln Lys Ile Glu Trp His Trp Thr Ser Lys Gly Gly Gly
    130                 135                 140

Leu Glu Ile Arg Ala Ala Phe Leu Arg Arg Arg Asn Thr Ala Leu Arg
145                 150                 155                 160

Thr Arg Val Ala Glu Leu Arg Gln Arg Val Gln Arg Leu Arg Asn Ile
            165                 170                 175

Val Ser Gln Tyr Glu Thr Arg Tyr Gly Pro Leu Thr Gly Ala Ser Gly
        180                 185                 190

Ala Gly Gly Ser Glu Gly Gly Ser Glu Gly Gly Thr Ser Gly Ala
    195                 200                 205

Thr Gly Ala Asn Ser Asp Ser Glu Cys Pro Leu Ser His Asp Gly Tyr
210                 215                 220

Cys Leu His Asp Gly Val Cys Met Tyr Ile Glu Ala Leu Asp Lys Tyr
225                 230                 235                 240

Ala Cys Asn Cys Val Val Gly Tyr Ile Gly Glu Arg Cys Gln Tyr Arg
            245                 250                 255

Asp Leu Lys Trp Trp Glu Leu Arg Leu Glu
        260                 265
```

<210> SEQ ID NO 28
<211> LENGTH: 285

```
<212> TYPE: PRT
<213> ORGANISM: unknown
<220> FEATURE:
<223> OTHER INFORMATION: protein NRG-NRG single construct

<400> SEQUENCE: 28

Arg Ile Ser Glu Phe Gly Thr Ser His Leu Val Lys Cys Ala Glu Lys
1               5                   10                  15

Glu Lys Thr Phe Cys Val Asn Gly Gly Glu Cys Phe Met Val Lys Asp
            20                  25                  30

Leu Ser Asn Pro Ser Arg Tyr Leu Cys Lys Cys Pro Asn Glu Phe Thr
        35                  40                  45

Gly Asp Arg Cys Gln Asn Tyr Val Met Ala Ser Phe Tyr Lys His Leu
50                  55                  60

Gly Ile Glu Phe Met Glu Ala Glu Leu Tyr Gln Lys Ile Asn Ala
65                  70                  75                  80

Ser Gly Ala Gly Gly Ser Glu Gly Gly Ser Glu Gly Gly Thr Ser
                85                  90                  95

Gly Ala Thr Thr Gly Gly Ser Gly Ser Ser His His His His His
                100                 105                 110

Ser Ser Gly Leu Val Pro Arg Gly Ser His Met Gly Leu Asn Asp Ile
        115                 120                 125

Phe Glu Ala Gln Lys Ile Glu Trp His Trp Thr Ser Lys Gly Gly
130                 135                 140

Leu Glu Ile Arg Ala Ala Phe Leu Arg Arg Arg Asn Thr Ala Leu Arg
145                 150                 155                 160

Thr Arg Val Ala Glu Leu Arg Gln Arg Val Gln Arg Leu Arg Asn Ile
                165                 170                 175

Val Ser Gln Tyr Glu Thr Arg Tyr Gly Pro Leu Thr Gly Ala Ser Gly
        180                 185                 190

Ala Gly Gly Ser Glu Gly Gly Ser Glu Gly Gly Thr Ser Gly Ala
        195                 200                 205

Thr Gly Ala Gly Thr Ser His Leu Val Lys Cys Ala Glu Lys Glu Lys
210                 215                 220

Thr Phe Cys Val Asn Gly Gly Glu Cys Phe Met Val Lys Asp Leu Ser
225                 230                 235                 240

Asn Pro Ser Arg Tyr Leu Cys Lys Cys Pro Asn Glu Phe Thr Gly Asp
                245                 250                 255

Arg Cys Gln Asn Tyr Val Met Ala Ser Phe Tyr Lys His Leu Gly Ile
        260                 265                 270

Glu Phe Met Glu Ala Glu Leu Tyr Gln Lys Leu Glu
        275                 280                 285

<210> SEQ ID NO 29
<211> LENGTH: 314
<212> TYPE: PRT
<213> ORGANISM: unknown
<220> FEATURE:
<223> OTHER INFORMATION: pMalc2x-EGF-LLAD10 construct

<400> SEQUENCE: 29

Met His His His His His His Ser Ser Gly Met Lys Glu Thr Ala Ala
1               5                   10                  15

Ala Lys Phe Glu Arg Gln His Met Asp Ser Pro Gly Ser Leu Val Pro
            20                  25                  30

Arg Gly Ser Leu Leu Ala Asp Thr His His Arg Pro Trp Thr Leu
        35                  40                  45
```

```
Leu Ala Asp Thr Thr His His Arg Pro Trp Thr Leu Leu Ala Asp Thr
     50                  55                  60

Thr His His Arg Pro Trp Thr Leu Leu Ala Asp Thr Thr His His Arg
 65                  70                  75                  80

Pro Trp Thr Leu Leu Ala Asp Thr Thr His His Arg Pro Trp Thr Leu
                 85                  90                  95

Leu Ala Asp Thr Thr His His Arg Pro Trp Thr Leu Leu Ala Asp Thr
            100                 105                 110

Thr His His Arg Pro Trp Thr Leu Leu Ala Asp Thr Thr His His Arg
        115                 120                 125

Pro Trp Thr Leu Leu Ala Asp Thr Thr His His Arg Pro Trp Thr Leu
130                 135                 140

Leu Ala Asp Thr Thr His His Arg Pro Trp Thr Glu Phe His His His
145                 150                 155                 160

Ser Ser Gly Leu Val Pro Arg Gly Ser His Met Gly Leu Asn Asp Ile
                165                 170                 175

Phe Glu Ala Gln Lys Ile Glu Trp His Trp Thr Ser Lys Gly Gly Gly
            180                 185                 190

Leu Glu Ile Arg Ala Ala Phe Leu Arg Arg Arg Asn Thr Ala Leu Arg
        195                 200                 205

Thr Arg Val Ala Glu Leu Arg Gln Arg Val Gln Arg Leu Arg Asn Ile
    210                 215                 220

Val Ser Gln Tyr Glu Thr Arg Tyr Gly Pro Leu Thr Gly Ala Ser Gly
225                 230                 235                 240

Ala Gly Gly Ser Glu Gly Gly Ser Glu Ser Gly Thr Ser Gly Ala
                245                 250                 255

Thr Gly Ala Asn Ser Asp Ser Glu Cys Pro Leu Ser His Asp Gly Tyr
            260                 265                 270

Cys Leu His Asp Gly Val Cys Met Tyr Ile Glu Ala Leu Asp Lys Tyr
        275                 280                 285

Ala Cys Asn Cys Val Val Gly Tyr Ile Gly Glu Arg Cys Gln Tyr Arg
    290                 295                 300

Asp Leu Lys Trp Trp Glu Leu Arg Leu Glu
305                 310

<210> SEQ ID NO 30
<211> LENGTH: 281
<212> TYPE: PRT
<213> ORGANISM: unknown
<220> FEATURE:
<223> OTHER INFORMATION: pMalc5x-EGF-cRR-LLAD10 ver 2 construct

<400> SEQUENCE: 30

Gly Ser Leu Leu Ala Asp Thr Thr His His Arg Pro Trp Thr Leu Leu
 1               5                  10                  15

Ala Asp Thr Thr His His Arg Pro Trp Thr Leu Leu Ala Asp Thr Thr
             20                  25                  30

His His Arg Pro Trp Thr Leu Leu Ala Asp Thr Thr His His Arg Pro
         35                  40                  45

Trp Thr Leu Leu Ala Asp Thr Thr His His Arg Pro Trp Thr Leu Leu
     50                  55                  60

Ala Asp Thr Thr His His Arg Pro Trp Thr Leu Leu Ala Asp Thr Thr
 65                  70                  75                  80

His His Arg Pro Trp Thr Leu Leu Ala Asp Thr Thr His His Arg Pro
                 85                  90                  95
```

Trp Thr Leu Leu Ala Asp Thr Thr His His Arg Pro Trp Thr Leu Leu
            100                 105                 110

Ala Asp Thr Thr His His Arg Pro Trp Thr Ala Ser Gly Ala Gly Gly
            115                 120                 125

Ser Glu Gly Gly Gly Ser Glu Gly Gly Thr Ser Gly Ala Thr Gly Ala
        130                 135                 140

Gly Thr Ser Thr Ser Gly Gly Gly Ala Ser Thr Gly Gly Gly Leu Glu
145                 150                 155                 160

Ile Arg Ala Ala Phe Leu Arg Arg Arg Asn Thr Ala Leu Arg Thr Arg
                165                 170                 175

Val Ala Glu Leu Arg Gln Arg Val Gln Arg Leu Arg Asn Ile Val Ser
            180                 185                 190

Gln Tyr Glu Thr Arg Tyr Gly Pro Leu Thr Gly Ala Ser Gly Ala Gly
        195                 200                 205

Gly Ser Glu Gly Gly Gly Ser Glu Gly Gly Thr Ser Gly Ala Thr Gly
    210                 215                 220

Ala Gly Thr Ser Asn Ser Asp Ser Glu Cys Pro Leu Ser His Asp Gly
225                 230                 235                 240

Tyr Cys Leu His Asp Gly Val Cys Met Tyr Ile Glu Ala Leu Asp Lys
                245                 250                 255

Tyr Ala Cys Asn Cys Val Val Gly Tyr Ile Gly Glu Arg Cys Gln Tyr
            260                 265                 270

Arg Asp Leu Lys Trp Trp Glu Leu Arg
        275                 280

<210> SEQ ID NO 31
<211> LENGTH: 281
<212> TYPE: PRT
<213> ORGANISM: unknown
<220> FEATURE:
<223> OTHER INFORMATION: pMalc5x-EGF-cEE-LLAD10 ver 2 construct

<400> SEQUENCE: 31

Gly Ser Leu Leu Ala Asp Thr Thr His His Arg Pro Trp Thr Leu Leu
1               5                   10                  15

Ala Asp Thr Thr His His Arg Pro Trp Thr Leu Leu Ala Asp Thr Thr
            20                  25                  30

His His Arg Pro Trp Thr Leu Leu Ala Asp Thr Thr His His Arg Pro
        35                  40                  45

Trp Thr Leu Leu Ala Asp Thr Thr His His Arg Pro Trp Thr Leu Leu
    50                  55                  60

Ala Asp Thr Thr His His Arg Pro Trp Thr Leu Leu Ala Asp Thr Thr
65                  70                  75                  80

His His Arg Pro Trp Thr Leu Leu Ala Asp Thr Thr His His Arg Pro
                85                  90                  95

Trp Thr Leu Leu Ala Asp Thr Thr His His Arg Pro Trp Thr Leu Leu
            100                 105                 110

Ala Asp Thr Thr His His Arg Pro Trp Thr Ala Ser Gly Ala Gly Gly
        115                 120                 125

Ser Glu Gly Gly Gly Ser Glu Gly Gly Thr Ser Gly Ala Thr Gly Ala
    130                 135                 140

Gly Thr Ser Thr Ser Gly Gly Gly Thr Ser Leu Glu Ile Glu Ala Ala
145                 150                 155                 160

Phe Leu Glu Gln Glu Asn Thr Ala Leu Glu Thr Glu Val Ala Glu Leu
                165                 170                 175

```
Glu Gln Glu Val Gln Arg Leu Glu Asn Ile Val Ser Gln Tyr Glu Thr
            180                 185                 190

Arg Tyr Gly Pro Leu Gly Gly Lys Thr Gly Ala Ser Gly Ala Gly
        195                 200                 205

Gly Ser Glu Gly Gly Ser Glu Gly Gly Thr Ser Gly Ala Thr Gly
210                 215                 220

Ala Gly Thr Ser Asn Ser Asp Ser Glu Cys Pro Leu Ser His Asp Gly
225                 230                 235                 240

Tyr Cys Leu His Asp Gly Val Cys Met Tyr Ile Glu Ala Leu Asp Lys
                245                 250                 255

Tyr Ala Cys Asn Cys Val Val Gly Tyr Ile Gly Glu Arg Cys Gln Tyr
                260                 265                 270

Arg Asp Leu Lys Trp Trp Glu Leu Arg
            275                 280

<210> SEQ ID NO 32
<211> LENGTH: 47
<212> TYPE: PRT
<213> ORGANISM: unknown
<220> FEATURE:
<223> OTHER INFORMATION: RR or C1 linker

<400> SEQUENCE: 32

Lys Gly Gly Gly Leu Glu Ile Arg Ala Ala Phe Leu Arg Arg Arg Asn
1               5                   10                  15

Thr Ala Leu Arg Thr Arg Val Ala Glu Leu Arg Gln Arg Val Gln Arg
            20                  25                  30

Leu Arg Asn Ile Val Ser Gln Tyr Glu Thr Arg Tyr Gly Pro Leu
        35                  40                  45

<210> SEQ ID NO 33
<211> LENGTH: 47
<212> TYPE: PRT
<213> ORGANISM: unknown
<220> FEATURE:
<223> OTHER INFORMATION: E2 or C2 linker

<400> SEQUENCE: 33

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu Gly Gly Lys
        35                  40                  45

<210> SEQ ID NO 34
<211> LENGTH: 22
<212> TYPE: PRT
<213> ORGANISM: unknown
<220> FEATURE:
<223> OTHER INFORMATION: spacer

<400> SEQUENCE: 34

Ala Ser Gly Ala Gly Gly Ser Glu Gly Gly Ser Glu Gly Gly Thr
1               5                   10                  15

Ser Gly Ala Thr Gly Ala
            20
```